United States Patent
Fujita et al.

(10) Patent No.: US 9,456,770 B2
(45) Date of Patent: Oct. 4, 2016

(54) DEVICE FOR DETERMINING BIOLOGICAL STATE DURING DRIVING AND COMPUTER PROGRAM

(71) Applicant: DELTA TOOLING CO., LTD., Hiroshima-shi (JP)

(72) Inventors: Etsunori Fujita, Higashihiroshima (JP); Yumi Ogura, Higashihiroshima (JP); Shinichiro Maeda, Hatsukaichi (JP); Ryuichi Uchikawa, Hiroshima (JP); Yoshika Nobuhiro, Hiroshima (JP)

(73) Assignee: DELTA TOOLING CO., LTD., Hiroshima-shi (JP)

( * ) Notice: Subject to any disclaimer, the term of this patent is extended or adjusted under 35 U.S.C. 154(b) by 0 days.

(21) Appl. No.: 14/651,874

(22) PCT Filed: Nov. 26, 2013

(86) PCT No.: PCT/JP2013/081693
§ 371 (c)(1),
(2) Date: Jun. 12, 2015

(87) PCT Pub. No.: WO2014/091916
PCT Pub. Date: Jun. 19, 2014

(65) Prior Publication Data
US 2015/0327803 A1  Nov. 19, 2015

(30) Foreign Application Priority Data
Dec. 14, 2012 (JP) ................................ 2012-274104

(51) Int. Cl.
*G08B 23/00* (2006.01)
*A61B 5/11* (2006.01)
(Continued)

(52) U.S. Cl.
CPC . *A61B 5/11* (2013.01); *A61B 5/18* (2013.01); *A61B 5/4809* (2013.01); *B60W 40/08* (2013.01); *B60W 2040/0827* (2013.01)

(58) Field of Classification Search
CPC ........ A61B 5/11; A61B 5/4809; A61B 5/18; B60W 40/08; B60W 2040/0827
USPC .................. 340/439, 575, 576, 309.5, 573.1; 180/272; 701/36, 49; 600/300, 485, 600/500, 504, 529
See application file for complete search history.

(56) References Cited

U.S. PATENT DOCUMENTS

| | | | |
|---|---|---|---|
| 7,532,964 B2 * | 5/2009 | Fujita ..................... | G08B 21/06 340/575 |
| 8,400,313 B2 * | 3/2013 | Noguchi .............. | A61B 5/7267 340/532 |

(Continued)

FOREIGN PATENT DOCUMENTS

| | | |
|---|---|---|
| JP | 2002-331603 A | 11/2002 |
| JP | 2003-182427 A | 7/2003 |

(Continued)

OTHER PUBLICATIONS

International Search Report issued Mar. 4, 2014 in PCT/JP2013/081693 filed Nov. 26, 2013.

*Primary Examiner* — Anh V La
(74) *Attorney, Agent, or Firm* — Oblon, McClelland, Maier & Neustadt, L.L.P.

(57) ABSTRACT

A device determining a biological state of a driver more accurately, including a hypnagogic symptom phenomenon detecting mechanism, an imminent sleep phenomenon detecting mechanism, a subjective sleepiness/low consciousness traveling state detecting mechanism, and a homeostasis function level determining mechanism, which are configured to function in parallel. Therefore, detection of a hypnagogic symptom phenomenon or an imminent sleep phenomenon, or detection of a period resisting a light sleepiness mild sleepiness or a strong sleepiness which occurs consciously, or the case where a low consciousness traveling state due to a decrease in consciousness level momentarily occurs or the case where it occurs longer continuously, or the like, can be determined/detected, and the driver's biological state can be accurately determined.

21 Claims, 32 Drawing Sheets

(51) Int. Cl.
  *A61B 5/00*   (2006.01)
  *B60W 40/08*  (2012.01)
  *A61B 5/18*   (2006.01)

(56) References Cited

U.S. PATENT DOCUMENTS

| | | | |
|---|---|---|---|
| 2003/0073886 A1* | 4/2003 | Yanagidaira | A61B 5/18 |
| | | | 600/300 |
| 2003/0116999 A1 | 6/2003 | Fujita et al. | |
| 2007/0299636 A1 | 12/2007 | Fujita et al. | |
| 2012/0212353 A1* | 8/2012 | Fung | B60K 28/06 |
| | | | 340/905 |
| 2012/0259181 A1 | 10/2012 | Fujita et al. | |
| 2013/0030256 A1 | 1/2013 | Fujita et al. | |
| 2013/0225940 A1 | 8/2013 | Fujita et al. | |

FOREIGN PATENT DOCUMENTS

| | | |
|---|---|---|
| JP | 2011-167362 A | 9/2011 |
| JP | 2012-95779 A | 5/2012 |
| JP | 2012-239480 A | 12/2012 |
| WO | 2005/092193 A1 | 10/2005 |
| WO | 2011/046178 A1 | 4/2011 |

* cited by examiner

FIG. 15A

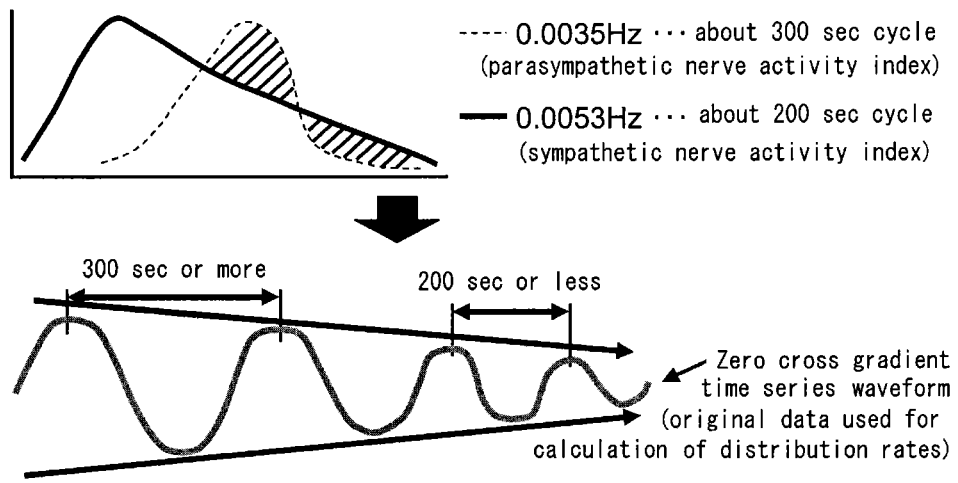

---- 0.0035Hz ⋯ about 300 sec cycle
(parasympathetic nerve activity index)

— 0.0053Hz ⋯ about 200 sec cycle
(sympathetic nerve activity index)

300 sec or more    200 sec or less

Zero cross gradient
time series waveform
(original data used for
calculation of distribution rates)

FIG. 15B $\chi$-squared test

|  |  | APW determination ||
|---|---|---|---|
|  |  | − (Wakeful) | + (Sleepiness appears) |
| Subjectivity | − (Wakeful) | 92 | 14 |
|  | + (Sleepiness appears) | 23 | 32 |

Correct answer rate : 77%    $p = 2.09 \times 10^{-9}$

FIG. 15C

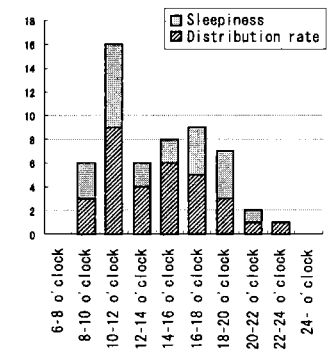

Subjective sleepiness number and
distribution rate determination number
Non-detection: 23 cases

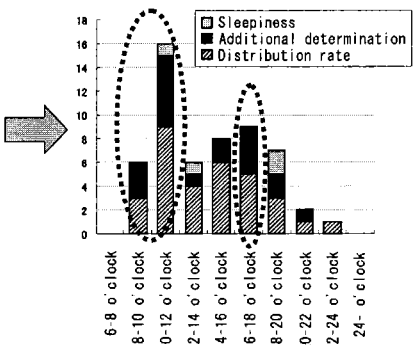

Subjective sleepiness number and distribution
rate/convergence determination number
Non-detection: 4 cases

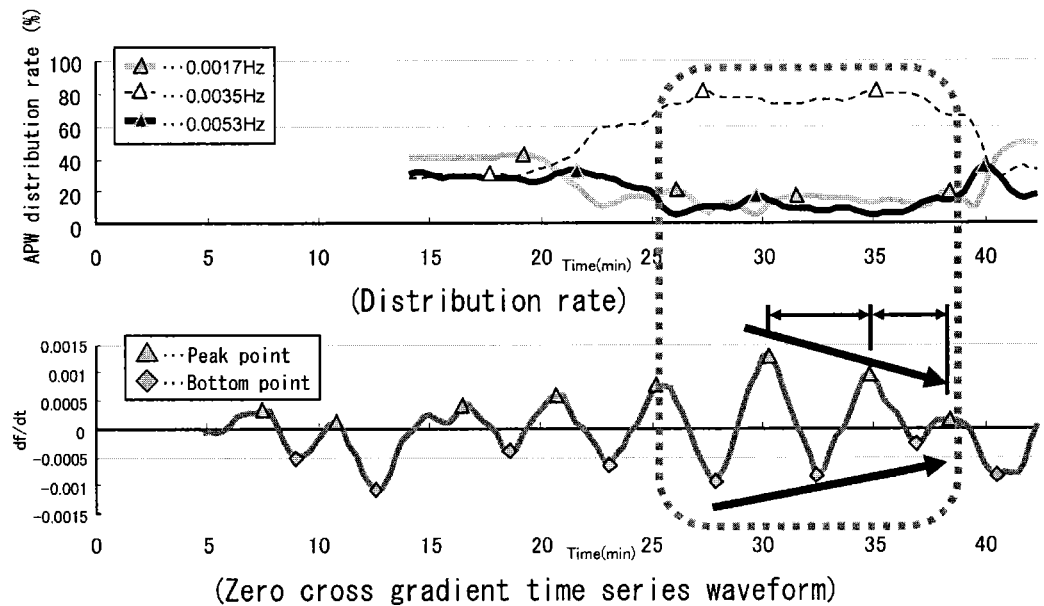

Gradient of APW

Gradient of fingertip

Gradient of APW

Gradient of fingertip

FIG. 29
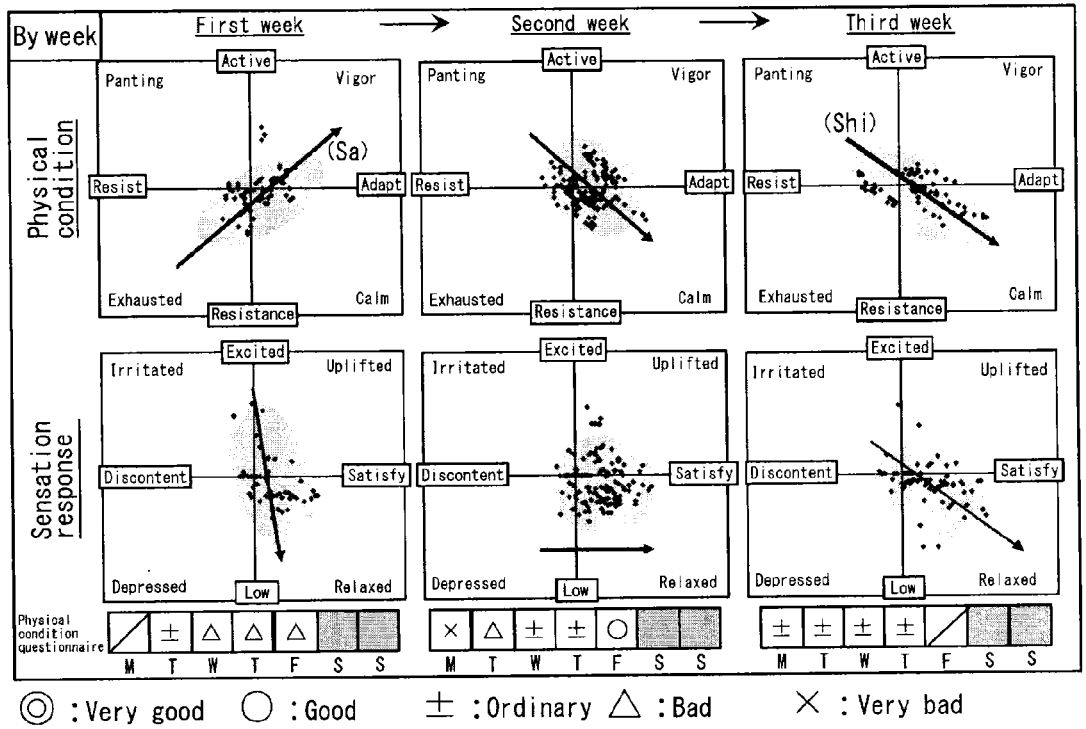
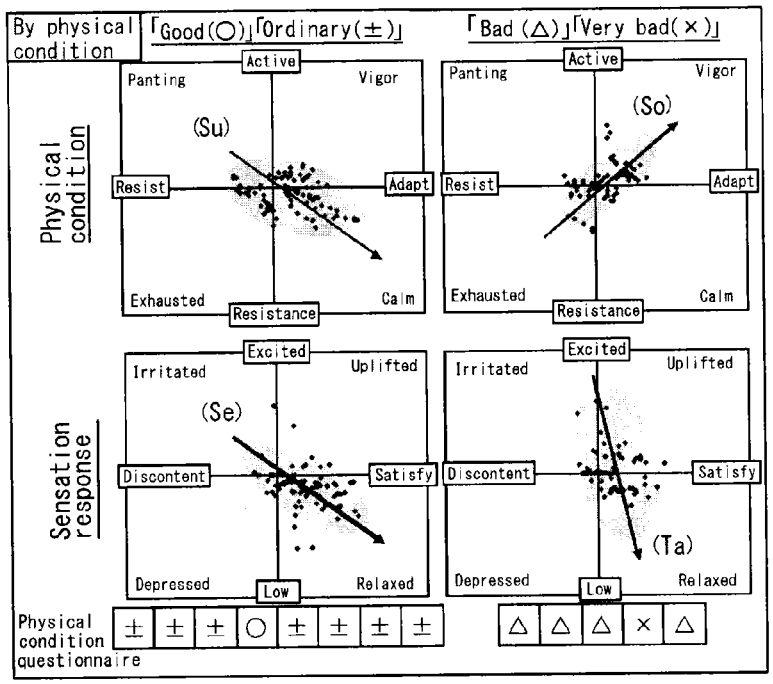

|  |  | Degree of separation between peak point and zero cross point | |
|---|---|---|---|
|  |  | Decrease | Increase or no change |
| Spectrum near 0.6 Hz | Decrease | 10 | 3 |
| Spectrum near 0.6 Hz | Increase or no change | 3 | 6 |

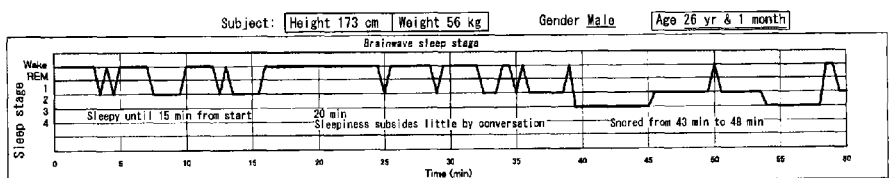
FIG. 32A
FIG. 32B
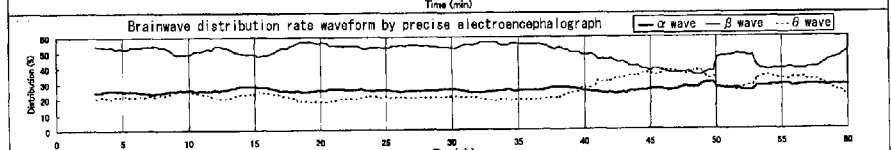
FIG. 32C
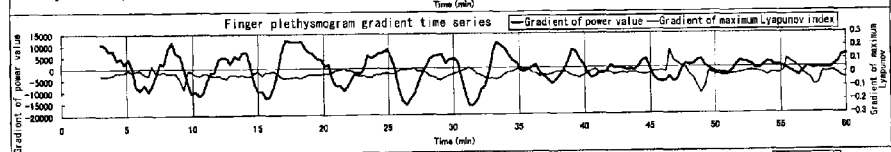
FIG. 32D
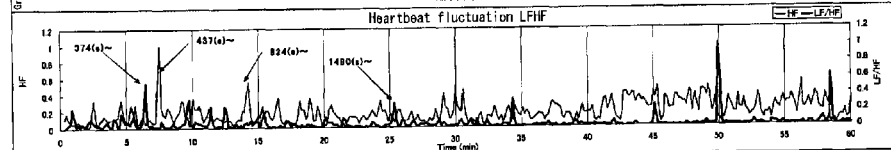
FIG. 32E
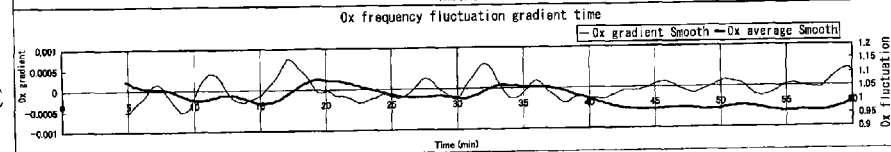
FIG. 32F
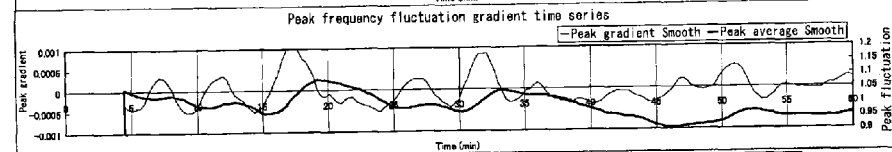
FIG. 32G
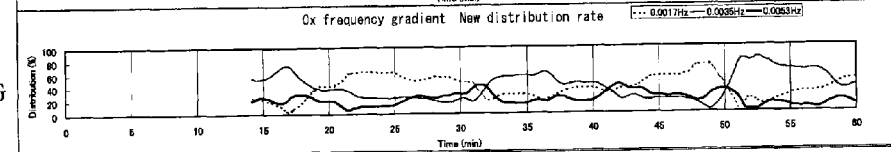
FIG. 32H
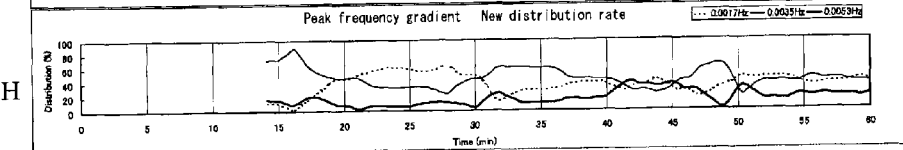

(374 - 399 sec sleep experiment: sympathetic nervous system increase)

(378 - 392 sec sleep experiment: sympathetic nervous system increase)

(378 - 392 sec vs 392 - 406 sec sleep experiment: frequency analysis)

DEVICE FOR DETERMINING BIOLOGICAL STATE DURING DRIVING AND COMPUTER PROGRAM

TECHNICAL FIELD

The present invention relates to a technology using a time series waveform of a biosignal obtained from the back of a person (driver) who performs driving or operation (which will be generically referred to as "driving" in this description) of a transportation apparatus, such as a vehicle, a train, an airplane, a ship, or the like, so as to determine what state the driver is in.

BACKGROUND ART

Monitoring a biological state of a driver during driving is gaining attention in recent is years as an accident prevention measure or the like. The present applicant has hitherto proposed various such techniques. Patent Document 1 discloses an apparatus having a procedure to obtain a time series waveform of a frequency mainly from a time series waveform of a biosignal which is cardiocirculatory pulsation sampled from an upper body of a person, further obtain a time series waveform of a frequency gradient and a time series waveform of a frequency fluctuation, and frequency-analyze them. When performing a frequency analysis, power spectra of respective frequencies corresponding to a function adjusting signal, a fatigue reception signal and an activity adjusting signal belonging in a ULF band (ultra low frequency band) to a VLF band (very low frequency band), which are predefined, are obtained. Then, the state of the person is determined from time series changes of the respective power spectra. The fatigue reception signal indicates the degree of progress of fatigue in a normal active state, and thus by comparing, together with this, the degrees of predominance of the power spectra of the function adjusting signal and the activity adjusting signal, the state of the person (relaxed state, fatigue state, sympathetic nerve predominant state, parasympathetic nerve predominant state, or the like) can be determined.

Patent Document 2 uses, similarly to Patent Document 1, the function adjusting signal, the fatigue reception signal and the activity adjusting signal belonging in the ULF band (ultra low frequency band) to the VLF band (very low frequency band), but Patent Document 2 is of a method obtaining, in time series, distribution rates of respective frequency components when a total of values of power spectra of the frequency components corresponding to the three signals is 100, and determining the state of a person by using time series changes in the distribution rates.

The techniques of Patent Documents 1 and 2 are both based on knowledge as follows. Specifically, human homeostasis is retained by fluctuation, and its frequency band is regarded to be in the ULF band and the VLF band. On the other hand, in atrial fibrillation as one of heat diseases, it is said that the point where a characteristic of fluctuation of the heart-circulatory system switches is 0.0033 Hz, and by grasping a change in fluctuation in the vicinity of 0.0033 Hz, information related to homeostasis can be obtained. Further, it is said that frequency bands in the vicinity of 0.0033 Hz or lower and in the vicinity of 0.0053 Hz are mainly related to body temperature adjustment, and the frequency band of 0.01 to 0.04 Hz is said to be related to control of autonomic nervous system. Then, when a frequency gradient time series waveform for calculating these fluctuations of low frequencies which are inherent in the biosignal was actually obtained and subjected to frequency analysis, it was confirmed that there were fluctuations of frequency band around 0.0017 Hz which is a lower frequency than 0.0033 Hz and 0.0035 Hz in the vicinity of 0.0033 Hz, and a fluctuation of frequency band around 0.0053 Hz besides these two.

The signal of 0.0035 Hz (fatigue reception signal) is a fluctuation for maintaining homeostasis by adapting to externally inputted stress, and this is a signal indicating the degree of progress of fatigue in a normal active state, the signal of 0.0053 Hz (activity adjusting signal) is a signal in which the degree of influence by control of endocrine hormones in an active time appears, the signal of 0.0017 Hz (function adjusting signal) which is a lower frequency than 0.0033 Hz is a signal controlling modulation and/or functional decrease of a body, and the signals of these three frequency bands are correlated one another to function as a body temperature adjusting function. Then, time series changes of power spectra and distribution rates of these signals are used for determining the state of a person.

PRIOR ART DOCUMENT

Patent Document

Patent document 1: Japanese Patent Application Laid-open No. 2011-167362
Patent document 1: Japanese Patent Application Laid-open No. 2012-95779

DISCLOSURE OF THE INVENTION

Problems to be Solved by the Invention

Those described in Patent Documents 1 and 2 are capable of widely grasping phenomena related to sleepiness such as a light sleepiness (mild sleepiness), a hypnagogic symptom phenomenon, a momentary sleep, and an imminent sleep, and among others, an ability to grasp the hypnagogic symptom phenomenon is emphasized. Although it is quite effective to determine the state of a person by using the above-described three frequency components belonging in the ULF band and the VLF band, further improvement in determination accuracy is constantly desired. For example, when it is applied to a warning system aiming at prevention of dozing, the hypnagogic symptom phenomenon, the imminent sleep phenomenon, or the like often occurs without the driver himself/herself being aware of it, but when, for example, the driver is in an overfatigue state from the beginning, the driver shifts to a state of tension because a rise in sympathetic function or control of various hormones (endocrine system) influences strongly in order to resist the overfatigue state, and a state that the driver is not aware (conscious) of sleepiness becomes mostly predominant. In other words, even when changes inside the body occur accompanying sleepiness, they are cancelled out by the state of tension and a warning is issued from the beginning of driving in a state of not being able to perceive sleepiness, and thus the driver may construe it as an erroneous determination. Conversely, about a sleepiness which can be recognized by (subjective for) the driver, if all kinds of sleepiness which come and go like ripples are warned, the warning itself may be considered bothersome and disliked. Thus, biological determination during driving is to be used for giving some kind of warning by using its determination result and hence demanded to issue a predetermined warning as reliably as possible at timing when the driver should be led to a wakeful state or the like, and it is desired that unnecessary warnings are as few as possible.

The present invention is made in view of the above situation, and it is an object thereof to provide a device for determining biological state during driving and a computer program which are capable of performing determination of a biological state of a driver during driving with higher accuracy, and capable of giving a warning at necessary timing as reliably as possible.

Means for Solving the Problems

In order to achieve the above-described object, the present inventors focused on the facts that a frequency gradient time series waveform of a biological signal sampled from the back of a driver, namely, aortic pulse wave (APW) is highly correlated with a frequency gradient time series waveform of a finger photoplethysmogram grasping a state of control of body temperature by a change in blood stream, and the state of body temperature control can be grasped from characteristics (amplitude, cycle) related to the frequency of the time series waveform of the APW, and that the balance of autonomic function can be grasped by subjecting the frequency gradient time series waveform of the APW to absolute value processing, and movement of control thereof can further be grasped from a change characteristic of fluctuation obtained by distribution rates, and the like. Accordingly, a determination criterion for each of them is set corresponding to various physical condition changes by using analytical calculation results by an analyzing and calculating means of them, so as to determine in parallel a hypnagogic symptom phenomenon or an imminent sleep phenomenon which mainly occurs unconsciously, light sleepiness which occurs consciously or strong sleepiness accompanying strong resistance to sleep, or a low consciousness traveling state in which the driver keeps traveling in a state of being unable to read or judge information even though the driver is not aware of sleepiness and opening eyes due to a significant decrease in consciousness level, or the like. The present inventors considered that the biological state of the driver can thus be grasped from multiple aspects and determination of the biological state can be performed with high accuracy, and thereby completed the present invention.

Specifically, a device for determining biological state during driving of the present invention is a device for determining biological state during driving, the device determining a biological state of a driver in a driving environment by using a biosignal sampled from a back of the driver by a biosignal measuring device provided in a driver's seat, the device having an analyzing and calculating means performing a predetermined calculation by using a time series waveform of the biosignal, and a determining and detecting means determining or detecting the biological state by using a calculation result of the analyzing and calculating means, wherein the determining and detecting means has a hypnagogic symptom phenomenon detecting means detecting a hypnagogic symptom phenomenon which is a physical condition change phenomenon before falling asleep, an imminent sleep phenomenon detecting means detecting an imminent sleep phenomenon which is a physical condition change phenomenon before falling asleep occurring after the hypnagogic symptom phenomenon occurs, a subjective sleepiness/low consciousness traveling state detecting means detecting a subjective sleepiness which is being conscious of a sleepiness by oneself or a low consciousness traveling state due to a decrease in consciousness level, and a homeostasis function level determining means determining a level of adaptation ability of a homeostasis function, wherein the hypnagogic symptom phenomenon detecting means, the imminent sleep phenomenon detecting means, the subjective sleepiness/low consciousness traveling state detecting means and the homeostasis function level determining means are configured to function in parallel.

Preferably, the analyzing and calculating means is structured to have a frequency calculating means obtaining a time series waveform of a frequency from the time series waveform of the biosignal, a frequency gradient calculating means performing a movement calculation to obtain a gradient of the frequency in every predetermined time window by using the time series waveform of the frequency obtained by the frequency calculating means, and outputting a time series change of the gradient of the frequency obtained in every time window as a frequency gradient time series waveform, a frequency fluctuation calculating means performing a movement calculation to obtain an average value of the frequency in every predetermined time window by using the time series waveform of the frequency obtained by the frequency calculating means, and outputting a time series change of the average value of the frequency obtained in every time window as a frequency fluctuation time series waveform, and a means extracting frequency components corresponding to a function adjusting signal, a fatigue reception signal and an activity adjusting signal which are predefined from the frequency gradient time series waveform obtained by the frequency gradient calculating means and obtaining a fluctuation of each of the frequency components.

Preferably, the means obtaining a fluctuation of frequency components corresponding to the function adjusting signal, the fatigue reception signal and the activity adjusting signal is structured to have a distribution calculating means obtaining, after the frequency components of less than 0.01 Hz belonging in a ULF band to a VLF band corresponding to the function adjusting signal, the fatigue reception signal and the activity adjusting signal are extracted, distribution rates of the respective frequency components in time series when a total of values of power spectra of the three frequency components is 100, and a degree of change calculating means applying smoothing differentiation to the time series distribution rates obtained by the distribution rate calculating means, and obtaining a degree of change of a distribution rate with respect to at least one frequency component from among the three frequency components between arbitrary time points on a time axis.

Preferably, the hypnagogic symptom phenomenon detecting means has a means determining that it is a hypnagogic symptom phenomenon when an increase tendency of amplitude is detected with respect to a predetermined criterion in the frequency gradient time series waveform obtained by the frequency gradient calculating means. Preferably, the imminent sleep phenomenon detecting means has a means determining that it is an imminent sleep phenomenon when a convergence tendency of amplitude is detected with respect to a predetermined criterion in the frequency gradient time series waveform obtained by the frequency gradient calculating means and a cycle thereof becomes a long cycle. Preferably, the subjective sleepiness/low consciousness traveling state detecting means has a means detecting a light sleepiness or a momentary low consciousness traveling state on a condition that the distribution rate of the frequency component corresponding to the function adjusting signal among the three frequency components obtained by the distribution rate calculating means is equal to or higher than the distribution rate of the frequency component corresponding to the activity adjusting signal. Preferably, the subjective sleepiness/low consciousness traveling state detecting means has a means detecting a light sleepiness or a momentary low consciousness traveling state on a condition that a degree of change of the frequency component corresponding to the function adjusting signal as well as a degree of change of the frequency component corresponding to the activity adjusting signal, among the three frequency components obtained by the degree of change calculating means, are equal to or larger than a predetermined value by absolute value.

Preferably, the subjective sleepiness/low consciousness traveling state detecting means has a means determining whether a basic state of the driver is a relaxed state or a state of tension, and selecting a determination criterion for whether or not to correspond to the light sleepiness or the momentary low consciousness traveling state depending on whether the determined basic state is a relaxed state or a state of tension. Preferably, the subjective sleepiness/low consciousness traveling state detecting means further has a means detecting a strong sleepiness or a continuous low consciousness traveling state when respective peak values of the time series waveforms of distribution rates of the three frequency components obtained by the distribution rate calculating means are values which appear in a predetermined order within a range of difference in predetermined appearance time, and satisfy a predetermined distribution rate condition.

Preferably, the means determining a driving unqualified period in the subjective sleepiness/low consciousness traveling state detecting means determines a strong sleepiness or a continuous low consciousness traveling state when appearance times of peak values satisfying the predetermined distribution rate condition of the three frequency components obtained by the distribution rate calculating means satisfy a following relation: activity adjusting signal≤function adjusting signal≤fatigue reception signal (where a difference in appearance times of the peak values of the activity adjusting signal and the fatigue reception signal is within a predetermined time). Preferably, the subjective sleepiness/ low consciousness traveling state detecting means has a means determining a subjective sleepiness or a low consciousness traveling state when a convergence tendency of amplitude is detected with respect to a predetermined criterion in the frequency gradient time series waveform obtained by the frequency gradient calculating means.

Preferably, the determining and detecting means further has an initial fatigue determining means determining presence of an initial fatigue at a start of driving, and the initial fatigue determining means determines that the driver has an initial fatigue when a same homeostasis function level continues for a predetermined time or more in the homeostasis function level determining means. Preferably, the determining and detecting means further has a feeling determining means determining a biological state in an early period of driving until a predetermined time passes after the driving is started. Preferably, the device further has a biological state determining means using history determining a biological state of a driver by using history information of determination results obtained by the hypnagogic symptom phenomenon detecting means, the imminent sleep phenomenon detecting means, the subjective sleepiness/low consciousness traveling state detecting means and the homeostasis function level determining means.

Preferably, the frequency calculating means is a means obtaining a zero cross point of switching from positive to negative in the time series waveform of the biosignal obtained by the biosignal measuring device, and obtaining a time series waveform of a frequency of a biosignal by using this zero cross point. Preferably, the frequency calculating means is a means obtaining a maximum value by performing smoothing differentiation of the time series waveform of the biosignal obtained by the biosignal measuring device, and obtaining a time series waveform of a frequency of a biosignal by using this maximum value. Preferably, a frequency of the function adjusting signal used in the distribution rate calculating means is 0.0027 Hz or less, a frequency of the fatigue reception signal is in a range of 0.002 to 0.052 Hz, and a frequency of the activity adjusting signal is 0.004 to 0.007 Hz.

Further, a computer program of the present invention causes a computer as a device for determining biological state during driving, the device determining a biological state of a driver in a driving environment by using a biosignal sampled from a back of the driver by a biosignal measuring device provided in a driver's seat, to execute an analyzing and calculating procedure performing a predetermined calculation by using a time series waveform of the biosignal, and a determining and detecting procedure determining or detecting the biological state by using a calculation result of the analyzing and calculating means, and to execute, as the determining and detecting procedure a hypnagogic symptom phenomenon detecting procedure detecting a hypnagogic symptom phenomenon which is a physical condition change phenomenon before falling asleep, an imminent sleep phenomenon detecting procedure detecting an imminent sleep phenomenon which is a physical condition change phenomenon before falling asleep occurring after the hypnagogic symptom phenomenon occurs, a subjective sleepiness/low consciousness traveling state detecting procedure detecting a subjective sleepiness which is being conscious of a sleepiness by oneself or a low consciousness traveling state due to a decrease in consciousness level, and a homeostasis function level determining procedure determining a level of adaptation ability of a homeostasis function, wherein the hypnagogic symptom phenomenon detecting procedure, the imminent sleep phenomenon detecting procedure, the subjective sleepiness/low consciousness traveling state detecting procedure and the homeostasis function level determining procedure are executed in parallel.

Effects of the Invention

The present invention has a hypnagogic symptom phenomenon detecting means, an imminent sleep phenomenon detecting means, a subjective sleepiness/low consciousness traveling state detecting means, and a homeostasis function level determining means, which are configured to function in parallel, as a determining and detecting means. Therefore, detection of a hypnagogic symptom phenomenon or an imminent sleep phenomenon, or detection of a period resisting a light sleepiness (mild sleepiness) or a strong sleepiness which occurs consciously, or the case where a low consciousness traveling state due to a decrease in consciousness level momentarily occurs or the case where it occurs longer continuously, or the like, can be determined/detected by the respective means, and a driver's biological state can be determined more accurately than conventional ones. Further, by a structure in which a change in adaptation ability level is determined by a homeostasis function level determining means, and an initial fatigue determining means is provided, in a driving initial stage, presence of an initial fatigue state in the driving initial stage when shifting from a different environment to a new environment as a driving environment can be determined. A biological state in this driving initial stage affects the state after several hours by the circadian rhythm or the like, and thus a caution or the like prompting to take a rest after several hours can be given to the driver in the driving initial stage.

In this manner, according to the present invention, the biological state of the driver can thus be grasped from multiple aspects, and appropriate driving and a rest at appropriate timing can be prompted easily, and it is preferred as a device for grasping a biological state during driving.

BRIEF DESCRIPTION OF DRAWINGS

FIGS. 6A to 6F illustrate an example of sleep experiment results, in which FIG. 6A illustrates distribution rate time series waveforms of brain waves, FIG. 6B illustrates gradient time series waveforms of a finger plethysmogram, FIG. 6C illustrates a frequency gradient time series waveform by using a zero cross detection method of APW, FIG. 6D illustrates a frequency gradient time series waveform by using a peak detection method of the APW, FIG. 6E illustrates distribution rates by using the zero cross detection method, and FIG. 6F illustrates a degree of change of a distribution rate.

FIG. 11 is a flowchart for explaining a determination step of a light sleepiness, or the like.

FIG. 12 is a flowchart for explaining a determination step of the light sleepiness, or the like.

FIG. 13 is a diagram for explaining a determination step of a strong sleepiness, or the like.

FIG. 14 is a flowchart for explaining a determination step of the strong sleepiness, or the like.

FIG. 15A is a diagram for explaining a method of detecting a subjective sleepiness or the like in a frequency gradient time series waveform. FIG. 15B is a diagram illustrating a result of a chi-squared test of a dynamic experiment of Experimental Example 1. FIG. 15C is a graph illustrating a difference in number of detections by presence of combined use of a detection method of a subjective sleepiness or the like by using the frequency gradient time series waveform.

FIG. 19A illustrates an example of detecting a subjective sleepiness or the like by using a frequency gradient time series waveform in 89 examples of a dynamic experiment of Experimental Example 1, and FIG. 19B illustrates results of a chi-squared test evaluating a detection result of the subjective sleepiness by the distribution rates together.

FIGS. 24A-24D illustrate a result of a sleep experiment of a subject in Experimental Example 3, in which FIG. 24A is a diagram illustrating distribution rates of brain waves, FIG. 24B is a diagram illustrating activity levels of a sympathetic nervous system (LF/HF) and a parasympathetic nervous system (HF) obtained from the finger photoplethysmogram, FIG. 24C is a diagram illustrating gradient time series waveforms of the finger photoplethysmogram, and FIG. 24D is a diagram illustrating a frequency gradient time series waveform and a frequency fluctuation time series waveform by the zero cross detection method of the APW.

FIG. 29 is a diagram illustrating an example of a physical condition management by using results of the demonstration experiment during long distance traveling of Experimental Example 4.

FIG. 31 is a diagram illustrating evaluation results of accuracy of a degree of separation of a peak point and a zero cross point of the APW in the Experimental Example 5.

FIGS. 32A to 32H are diagrams illustrating sleep experiment results of Experimental Example 6.

BEST MODE FOR CARRYING OUT THE INVENTION

Figure 1:
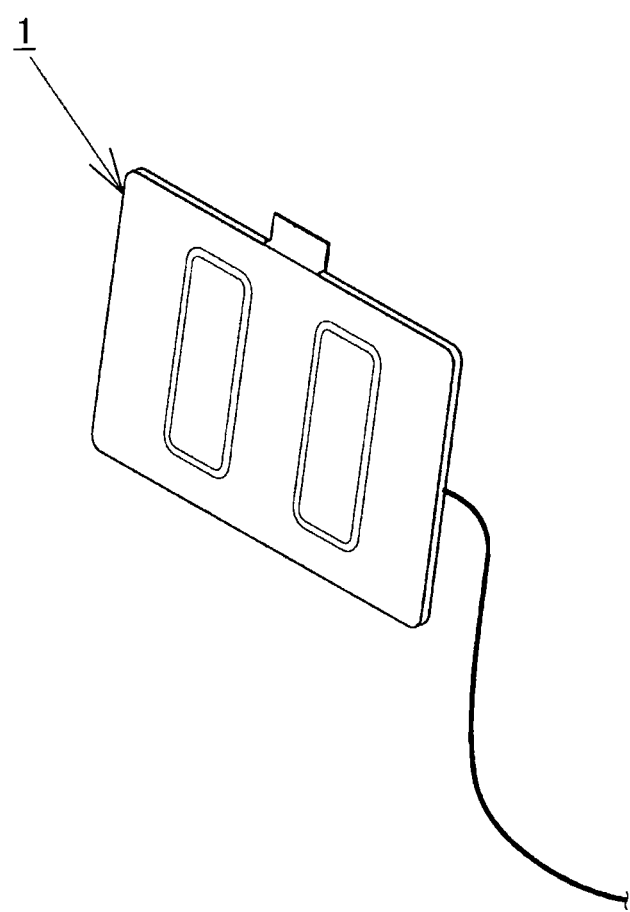
FIG. 1 is a perspective view illustrating an example of a biosignal measuring device for trunk used in one embodiment of the present invention.
Figure 2:
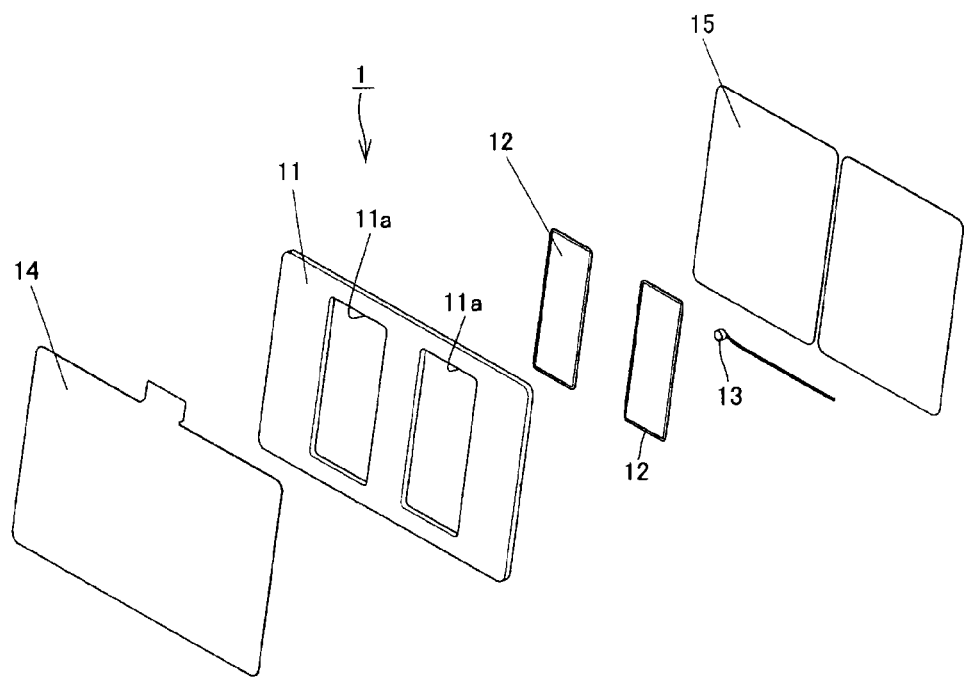
FIG. 2 is an exploded perspective view of the biosignal measuring device for trunk illustrated in FIG. 1.
Figure 3:
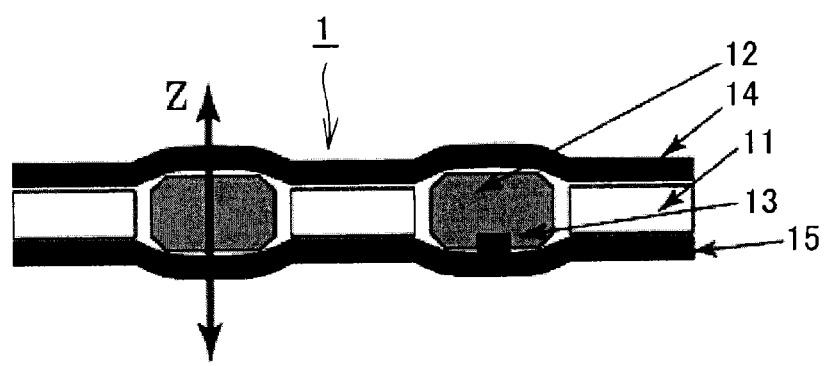
FIG. 3 is a cross-sectional view of a substantial part of the biosignal measuring device for trunk illustrated in FIG. 1.

Hereinafter, the present invention will be described in further detail based on embodiments of the present invention illustrated in drawings. FIG. 1 to FIG. 3 are views illustrating a biosignal measuring device 1 which samples a biological signal sampled from the back of a driver, namely, aortic pulse wave (APW), which is an analysis target of a device for determining biological state during driving 60 according to one embodiment of the present invention. The aortic pulse wave is pressure vibration generated from motions of the heart and aortas, which are detected from the back of the upper body of a person, and include information of systoles and diastoles of ventricles. Further, an increase in internal pressure of arterial tubes to be an auxiliary pump of circulation is propagated as waves to the periphery along blood vessels, and accompanying this propagation blood vessel walls are expanded. Therefore, the aortic pulse wave (APW) includes elasticity information of blood vessel walls and elasticity information by blood pressure. That is, the aortic pulse wave (APW) is information including both information at a location close to the center which is obtained from cardiac sound and an electrocardiogram and information of an output wave in which influences of internal pressure fluctuation and elasticity of blood vessel walls of arterial tubes are superposed on an input wave originated in the heart (that is, information in which a cyclic characteristic is changed by information of the periphery obtained from a finger plethysmogram which originally becomes the same cycle and the same fluctuation). Then, a signal waveform accompanying a heartbeat fluctuation includes nerve activity information of a sympathetic nervous system and a parasympathetic nervous system (activity information of the parasympathetic nervous system including compensation for sympathetic nerves), and a signal waveform accompanying pulsations of aortas includes information of sympathetic nerve activity.

The biosignal measuring device 1 used in this embodiment is structured to have, as illustrated in FIG. 2 and FIG. 3, a core pad 11, spacer pads 12, a sensor 13, a front film 14, and a rear film 15.

The core pad 11 is, for example, formed in a plate shape, in which two vertically long through holes 11a, 11a are formed at symmetrical positions across a portion corresponding to a spine. The core pad 11 is preferred to be formed from a bead foam of polypropylene formed in a plate shape. When the core pad 11 is formed from the bead foam, it is preferred to be formed with a foaming ratio in the range of 25 to 50 times and the thickness is formed to be equal to or less than an average diameter of beads. For example, when the average diameter of beads foamed by 30 times is about 4 to 6 mm, it is slice-cut with the thickness of the core pad 11 being about 3 to 5 mm.

The spacer pads 12 are fitted in the through holes 11a, 11a of the core pad 11. The spacer pads 12 are preferably formed of a three-dimensional knitted fabric. The three-dimensional knitted fabric is, for example, as disclosed in Japanese Patent Application Laid-open No. 2002-331603, Japanese Patent Application Laid-open No. 2003-182427, or the like, a knitted fabric made as a three-dimensional structure having a pair of ground knitted fabrics disposed separately from each other and numerous connecting yarns which reciprocate between the pair of ground knitted fabrics to couple them. When the three-dimensional knitted fabric is pressurized by the back of a person, the connecting yarns of the three-dimensional knitted fabric are compressed, a tension occurs in the connecting yarns, and vibrations of a body surface via muscles of the person accompanying a biosignal are propagated. Further, it is preferred to use thicker one for the spacer pads 12 formed of the three-dimensional knitted fabric than that for the core pad 11. Thus, when peripheral edges of the front film 14 and the rear film 15 are adhered to peripheral edges of the through holes 11a, 11a, the spacer pads 12 formed of the three-dimensional knitted fabric are pressed in a thickness direction. Thus, a tension due to stress of the front film 14 and the rear film 15 occurs, and it becomes easy for a solid vibration (film vibration) to occur in the front film 14 and the rear film 15. On the other hand, a pre-compression occurs also in the spacer pads 12 formed of the three-dimensional knitted fabric and a tension due to stress also occurs in the connecting yarns retaining the form in the thickness direction of the three-dimensional knitted fabric, and it becomes easy for a string vibration to occur.

The sensor 13 is disposed fixedly to one of the spacer pads 12 before the above-described front film 14 and rear film 15 are stacked. The three-dimensional knitted fabric forming the spacer pads 12 is formed of the pair of ground knitted fabrics and the connecting yarns as described above. String vibrations of the connecting yarns are transmitted to the front film 14 and the rear film 15 via nodal points to the ground knitted fabrics, and thus the sensor 13 is preferred to be fixed to a surface of the spacer pad 12 (surface of the ground knitted fabrics). As the sensor 13, a microphone sensor, among others, a condenser microphone sensor is preferably used.

The above-described biosignal measuring device 1 is, for example, disposed in a position of a seatback of a driver's seat of a transportation apparatus such as an automobile. For example, it is provided by disposing inside a surface layer of the seatback or disposing in a rear surface of a cushion member used by stacking on the seatback.

Figure 4:
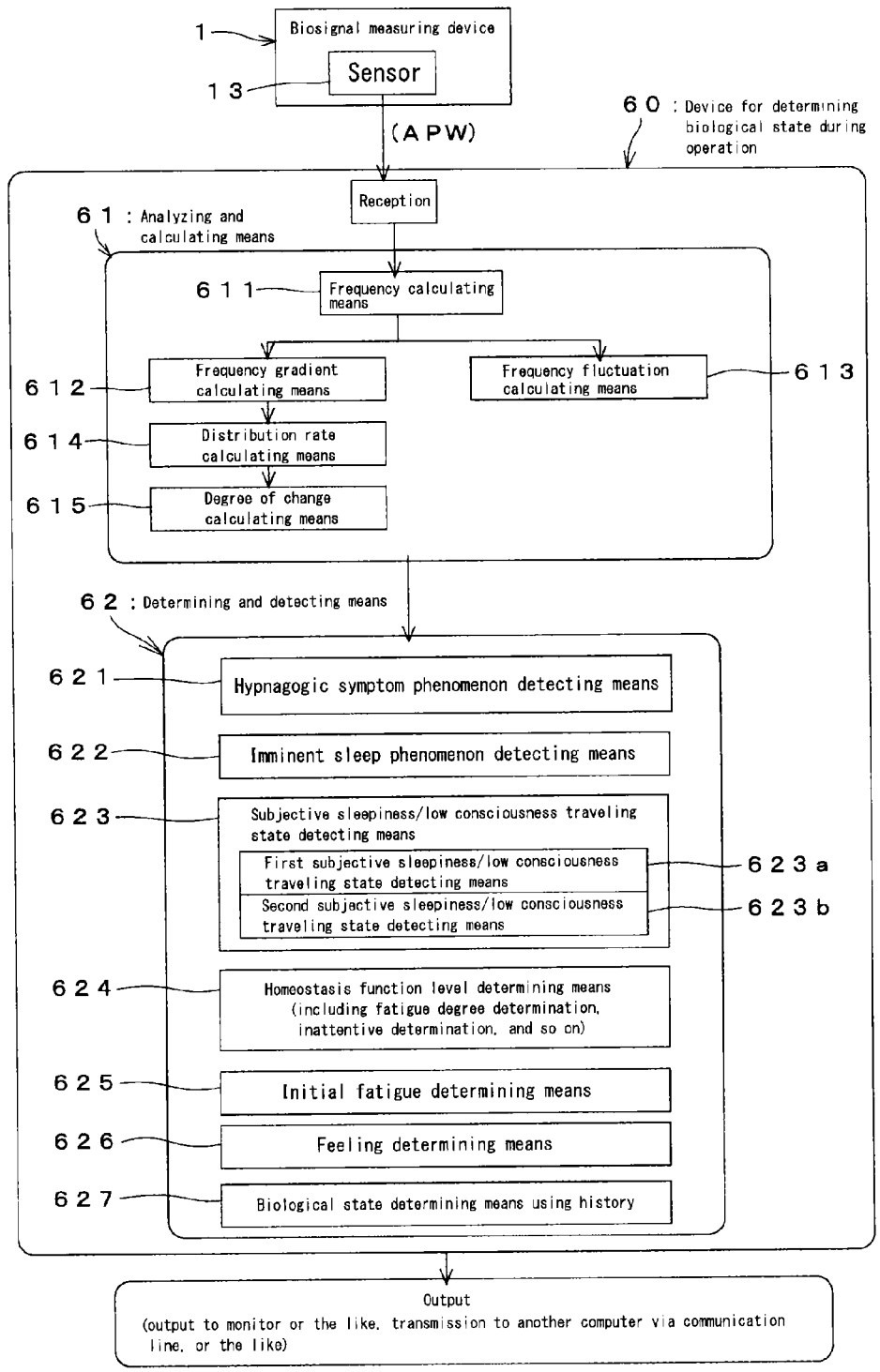
FIG. 4 is a diagram schematically illustrating a structure of a biological state analyzing device according to one embodiment of the present invention.

Next, a structure of the device for determining biological state during driving 60 of this embodiment will be described based on FIG. 4. The device for determining biological state during driving 60 is structured to have an analyzing and calculating means 61, a determining and detecting means 62, and so on. The device for determining biological state during driving 60 is constituted of a computer, and a computer program is introduced therein which causes the computer to execute an analyzing and calculating procedure to function as the analyzing and calculating means 61, and execute a determining and detecting procedure to function as the determining and detecting means 62. Note that the computer program can be provided by storing in a recording medium such as a flexible disk, a hard disk, a CD-ROM, a MO (magneto-optical disk), a DVD-ROM, or a memory card, or can be transmitted through a communication line.

The analyzing and calculating means 61 analyzes and calculates an APW which is a biosignal obtained from the biosignal measuring device 1 to process it into a predetermined form. Specifically, the means is structured to have a frequency calculating means 611, a frequency gradient calculating means 612, a frequency fluctuation calculating means 613, a distribution rate calculating means 614, and a degree of change calculating means 615, and these means function by executing a frequency calculating procedure, a frequency gradient calculating procedure, a frequency fluctuation calculating procedure, a distribution rate calculating procedure, and a degree of change calculating procedure, which are computer programs, respectively.

The frequency calculating means 611 obtains a time series waveform of a frequency in time series data of an output signal (APW) obtained from the sensor 13 of the biosignal measuring device 1, preferably, time series data of a predetermined frequency region which is subjected to a filtering process (for example, a filtering process removing frequency components of body movement, or the like).

Figure 5:
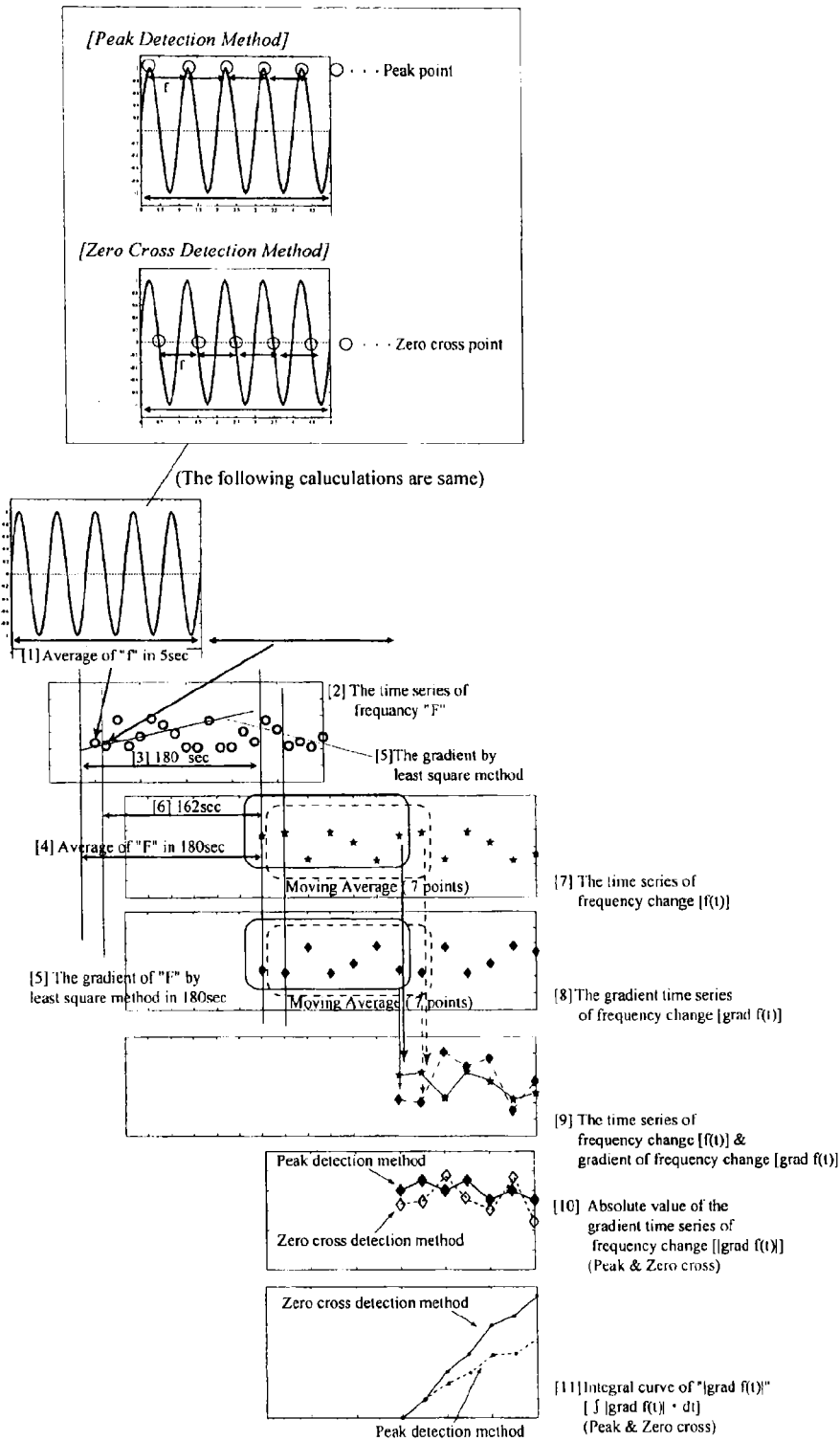
FIG. 5 is a diagram for explaining a frequency calculating means and a frequency gradient calculating means in an analyzing and calculating means.

The frequency calculating means 611 is a method obtaining a time series waveform of a frequency by using a point of switching from positive to negative (hereinafter referred to as a "zero cross point") in a time series waveform of the output signal (APW) obtained from the sensor of the biosignal measuring device 1 (hereinafter referred to as a "zero cross detection method"). This zero cross detection method is to grasp basic components of the frequency of a biosignal, and indicates the intensity level of expression of LF/HF used as an index of sympathetic function. In this method, first, once the zero cross point is obtained, it is divided by every five seconds for example, a reciprocal of a time interval between zero cross points of the time series waveform included in the five seconds is obtained as an individual frequency f, and an average value of the individual frequencies f in the five seconds is employed as a value of a frequency F of the five seconds (step of [1] of FIG. 5). Then, frequencies F obtained in every five seconds are plotted, thereby obtaining the time series waveform of the frequency (step of [2] of FIG. 5).

As the frequency calculating means 611, it is also possible to employ a method for obtaining a time series waveform by using a maximum value (peak) by smooth differentiation of the time series waveform of the output signal (APW) obtained from the sensor of the biosignal measuring device 1 (hereinafter referred to as a "peak detection method"). The peak detection method basically obtains a time series waveform corresponding to the function of HF used as an index of parasympathetic function. For example, the maximum value is obtained by the smooth differentiation by Savitzky and Golay. Next, for example, the maximum value is divided by every five seconds, a reciprocal of a time interval between maximum values of the time series waveform (apexes of mountain sides of the waveform) included in the five seconds is obtained as an individual frequency f, and an average value of the individual frequencies f in the five seconds is employed as a value of a frequency F of the five seconds (step of [1] of FIG. 5). Then, frequencies F obtained in every five seconds are plotted, thereby obtaining the time series waveform of the frequency (step of [2] of FIG. 5).

Here, the APW is a biosignal including information of both the condition of control of a peripheral system and the condition of control of a heart similarly to the finger plethysmogram, that is, a biosignal including the condition of sympathetic predominant state of artery, as well as appearance information of the sympathetic nervous system and the parasympathetic nervous system of an autonomic nervous system. A waveform obtained by absolute value processing of a gradient time series waveform by this zero cross detection method of the biosignal is more associated with the state of control of a heart, and reflects an appearance state of the sympathetic nervous system. A waveform by the peak detection method is more associated with heartbeat fluctuation and grasps a dynamic state of the parasympathetic nervous system to which compensation by the sympathetic nervous system is added. Note that a waveform obtained by absolute value processing of a gradient time series waveform by the peak detection method is relatively approximate to a dynamic state of the parasympathetic nervous system (this dynamic state of the parasympathetic nervous system is one to which sympathetic compensation is added) by wavelet analysis of the finger plethysmogram. Thus, it is conceivable that the zero cross detection method can be used for an index representing a physical condition which is a result of adaptation to stress addressed by control of the autonomic nervous system. Because it is highly associated with the state of control of the heart, the zero cross detection method also includes information of incisure of heartbeat fluctuation, and a frequency component of phase delay occurring in the vicinity of 0.5 Hz or the vicinity of 1 to 2 Hz due to a time phase difference of the APW and occurrence of fluctuation can be obtained as information, which cannot be obtained by the finger plethysmogram. Therefore, upon determining the biological state using the APW, it is preferred to mainly use data obtained by the zero cross detection method.

The frequency gradient calculating means 612 is configured to set a time window with a predetermined overlap time and a predetermined time width from the time series waveform of the frequency of the output signal of the sensor of the biosignal measuring device 1 obtained by the frequency calculating means 611, obtain a gradient of the frequency of the output signal of the sensor by a least square method in every time window, and output the time series waveform thereof. Specifically, first, a gradient of a frequency in a certain window Tw1 is obtained by the least square method and plotted (steps of [3], [5] of FIG. 5). Next, a next time window Tw2 is set in an overlap time T1 (step of [6] of FIG. 5), and a gradient of a frequency in this time window Tw2 is similarly obtained by the least square method and plotted. This calculation (movement calculation) is repeated sequentially, and a time series change of gradient of an air pack signal is outputted as a frequency gradient time series waveform (step of [8] of FIG. 5). Note that the time width of the time window Tw is preferably set to 180 seconds, and the overlap time T1 is preferably set to 162 seconds. As described in above Patent Document 3 (WO2005/09219A1 publication) by the present applicant, they were chosen as values by which characteristic signal waveforms appear most sensitively from a sleep experiment performed by variously changing the time width and the overlap time T1 of the time window Tw.

Further, as described above, a characteristic of fluctuation of atrial fibrillation switches at 0.0033 Hz, and it is said that a fluctuation for adjusting the fluctuation of 0.0033 Hz exists in the vicinity of 0.0033 Hz or lower. Therefore, when the state of fluctuation around 0.0017 Hz which is intermediate between 0 Hz and 0.0033 Hz is seen, it is conceivable that an overview of state of fluctuation appears, which occurs in the vicinity of 0.0033 Hz or lower even if dispersion occurs. The time corresponding to a ¼ period of the waveform of 0.0017 Hz is 147 seconds. Assuming that the waveform is smoothed in a 90% lap state, when a preceding and subsequent time of 10% is added, 147/0.8=approximately 180 seconds. Also from this point, it can be said that 180 seconds is preferred. Here, a condition of progressive change, a tendency of change, a derivative coefficient, and a gradient during 180 seconds, three minutes, are grasped as a time series waveform. Then, a gradient which is an average value for 180 seconds, on which 90% of the time of 180 seconds is lapped for smoothing, is plotted every 18 seconds to create a time series waveform, and the time series waveform of this gradient is used for performing an analysis. The time series waveform of this gradient grasps fluctuations of homeostasis, and is for evaluating in a large sense the degree of control of heartbeat fluctuation as a time series waveform.

The frequency fluctuation calculating means 613 performs a movement calculation to obtain an average value of a frequency in every predetermined time window set in a predetermined overlap time in the time series waveform obtained in the frequency calculating means 611, and outputs a time series change of the average value of the frequency obtained in every time window as a frequency fluctuation time series waveform. As described above, the time series waveform of a frequency obtained by the peak detection method grasps information of both the sympathetic nerve activity and the parasympathetic nerve activity, and the time series waveform of a frequency obtained by the zero cross detection method grasps information of the sympathetic nerve activity. Assuming that the frequency fluctuation time series waveform by the zero cross detection method grasps the sympathetic nerve activity, in a sleep state it is affected by a decrease in sympathetic nerve activity and thus the frequency decreases. Assuming that the frequency fluctuation time series waveform by the peak detection method grasps both the sympathetic nerve activity and the parasympathetic nerve activity, in a sleep state it is affected by both a decrease in the sympathetic nerve activity and a rise in the parasympathetic nerve activity, and thus the frequency further decreases than in the case of the zero cross detection method. Therefore, when the two frequency fluctuation time series waveforms are compared by wakeful state and sleep state, a change occurs in degree of separation of the both. That is, the degree of separation of the both becomes smaller in a sleep state than in a wakeful state (see FIG. 30C).

Therefore, utilizing this, by obtaining plural pieces of data of the degree of separation between the wakeful state and the sleep state in advance and setting thresholds therefrom, whether it is the wakeful state or the sleep state can be determined automatically. Although normally the driver would not fall asleep during driving, if a degree of separation determining means using the frequency fluctuation time series waveform is set as the determining and detecting means 62 of the device for determining biological state during driving 60 of this embodiment, it can be configured to issue a predetermined warning in case that shift to the sleep state is detected. However, although the driver would not fall asleep during driving, it is of course possible that the driver has a sleep in a break time. Therefore, it is also possible to activate the degree of separation determining means after driving is finished, and objectively know what time the driver took a break and had a sleep. In this case, one that executes the degree of separation determining means which is a computer program for determination may be an onboard device for determining biological state during driving 60, or data accumulated in the onboard device for determining biological state during driving 60 may be used, analyzed by a management computer for manager in which the degree of separation determining means is set, and used for managing states during driving of every driver. Of course, it may be set such that data obtained by the onboard device for determining biological state during driving 60 are transmitted to the management computer constantly or periodically via a communication line, and in this case, the management computer can determine the degree of separation based on the received data.

The distribution rate calculating means 614 has a means frequency-analyzing the frequency gradient time series waveform obtained from the frequency gradient calculating means 612 and obtaining power spectra of respective frequencies corresponding to the function adjusting signal, the fatigue reception signal and the activity adjusting signal described above, and extracts frequency components corresponding to the function adjusting signal, the fatigue reception signal and the activity adjusting signal described above which are predefined from the time series change of the obtained power spectra, calculates ratios of the three frequency components in time series when the total of values of power spectra of these three frequency components is 100, and obtains a time series fluctuation waveform thereof as a distribution rate waveform. Here, in this embodiment, as described above, 0.0017 Hz is the function adjusting signal, 0.0035 Hz is the fatigue reception signal, and 0.0053 Hz is the activity adjusting signal. Note that the function adjusting signal is in the range of 0.0027 Hz or lower, the fatigue reception signal is in the range of 0.002 to 0.0052 Hz, and the frequency of the activity adjusting signal can be adjusted in the range of 0.004 to 0.007 Hz.

The degree of change calculating means 615 applies smoothing differentiation to the time series distribution rates obtained by the distribution rate calculating means, and obtains a degree of change of the distribution rate of at least one frequency component from among the three frequency components, the function adjusting signal, the fatigue reception signal and the activity adjusting signal described above, between arbitrary time points on a time axis. At this time, the arbitrary time points on a time axis where the smoothing differentiation is applied can be appropriately chosen from two or more points on the time axis employed as calculation points. In this case, for example, it is preferred to obtain degrees of change by several types of calculation methods, such as the case where smoothing differentiation at two points is applied and the case where smoothing differentiation at 11 points is applied. By setting determination criterion with a different threshold for the degrees of change obtained respectively, more accurate determination becomes possible.

The determining and detecting means 62 is a means determining or detecting the biological state by using a calculation result of the analyzing and calculating means of the analyzing and calculating means 61, and is structured to have a hypnagogic symptom phenomenon detecting means 621, an imminent sleep phenomenon detecting means 622, a subjective sleepiness/low consciousness traveling state detecting means 623, a homeostasis function level determining means 624, an initial fatigue determining means 625, and so on, and these means function by executing a hypnagogic symptom phenomenon detecting procedure, an imminent sleep phenomenon detecting procedure, a subjective sleepiness/low consciousness traveling state detecting procedure, a homeostasis function level determining procedure, an initial fatigue determining procedure, and so on, which are computer programs, respectively.

The hypnagogic symptom phenomenon detecting means 621 detects a hypnagogic symptom phenomenon. The hypnagogic symptom phenomenon is a physical condition change phenomenon which occurs 5 to 30 minutes before falling asleep, but does not accompany a subjective sleepiness. Thus, it is grasped by a signal that is a rise in sympathetic function.

Figure 6:
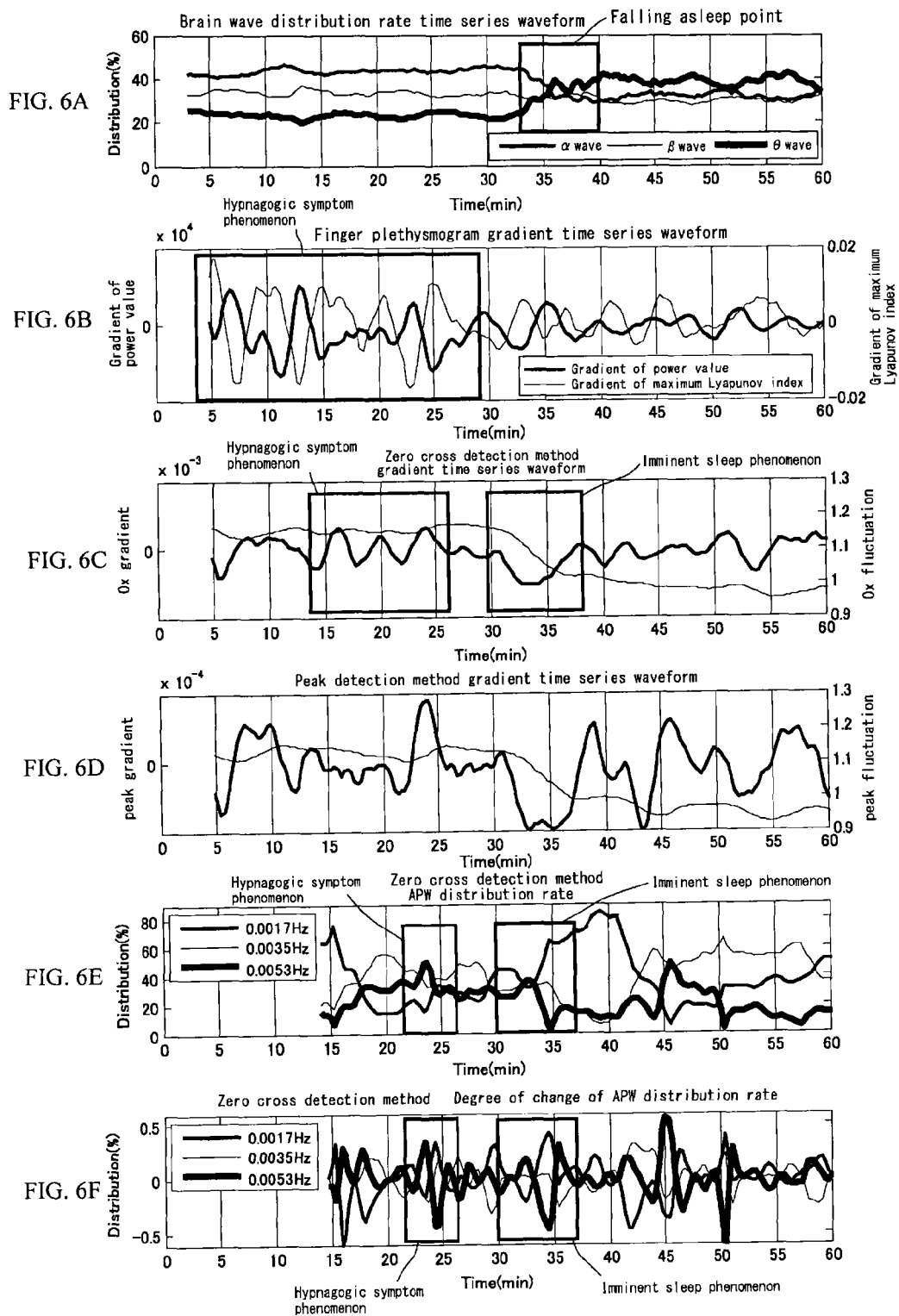

The hypnagogic symptom phenomenon detecting means 621 performs determination by using an index related to autonomic nerve control among calculation results of the above-described analyzing and calculating means 61. In this embodiment, the frequency gradient time series waveform by the frequency gradient calculating means 612 using the zero cross detection method is used to perform determination. FIGS. 6A-6F illustrate an example of sleep experiment results, in which FIG. 6C illustrates an example of the frequency gradient time series waveform by using the zero cross detection method. The hypnagogic symptom phenomenon is basically determined by that waves with large amplitude appear several times sequentially in the frequency gradient time series waveform. As illustrated in FIG. 6A, from the relation of α wave, β wave, θ wave of brain waves, the vicinity of 33 to 40 minutes can be determined as a point of falling asleep (falling asleep point). On the other hand, in the frequency gradient time series waveform of FIG. 6C, waves with large amplitude sequentially appear in the vicinity of 14 to 26 minutes, that is, 7 to 26 minutes before the falling asleep point, and this waveform can be identified as the hypnagogic symptom phenomenon accompanying a rise in the sympathetic function. The hypnagogic symptom phenomenon can be identified in real time by performing determination based on criteria obtained by statistically studying what difference this waveform with large amplitude appears with from previous waveforms from examination results performed on a large number of subjects.

Figure 7:
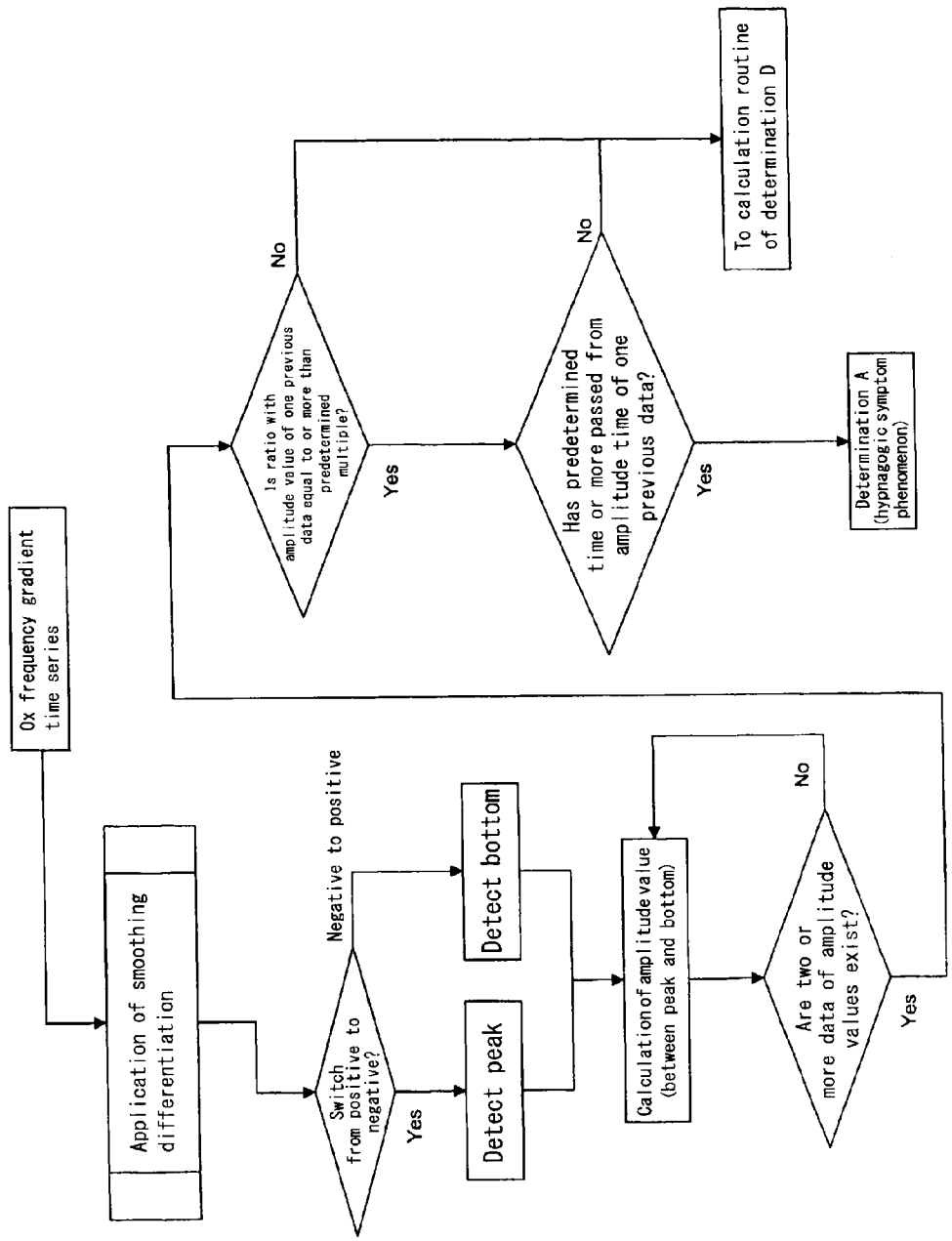
FIG. 7 is a flowchart for explaining a determination step of a hypnagogic symptom phenomenon.

In this embodiment, as illustrated in FIG. 7, first, the frequency gradient time series waveform using the zero cross detection method is subjected to smoothing differentiation, a point of switching from positive gradient to negative gradient is detected as a peak, a point of switching from negative gradient to positive gradient is detected as a bottom, and an amplitude value between the both is calculated. Next, whether a plurality of such amplitude values exist or not is obtained, and if a plurality of them exist, a comparison of magnitude with the amplitude value of one previous data piece is made. If the ratio of magnitude is equal to or more than a predetermined multiple and a predetermined time or longer has passed from the time when the amplitude value of one previous data piece is obtained, it is determined as the hypnagogic symptom phenomenon.

From the above fact, when a diversion tendency of frequency gradient time series waveform appears such that appearance of a waveform with large amplitude occurs with respect to a predetermined criterion, it can be determined as the hypnagogic symptom phenomenon. Further, as illustrated in FIG. 20, its cycle also becomes a long cycle at timing when such an increase tendency of amplitude occurs, and thus it is preferred to be structured to determine the hypnagogic symptom phenomenon when the cycle becomes a long cycle according to the increase tendency.

The imminent sleep phenomenon detecting means 622 detects an imminent sleep phenomenon. The imminent sleep phenomenon is a phenomenon which occurs after the hypnagogic symptom phenomenon appears and 1 to 5 minutes before the driver falls asleep in a state that the parasympathetic function accompanying a decrease in the sympathetic function is predominant, and thus is grasped by signals as a decrease in the sympathetic function and a rise in the parasympathetic function. The imminent sleep phenomenon is, in many cases, a non-subjective physical condition change phenomenon similarly to the hypnagogic symptom phenomenon, but may accompany a subjective strong sleepiness depending on the person or the physical condition and/or the surrounding environment at the moment.

The imminent sleep phenomenon is a point on the frequency gradient time series waveform using the zero cross detection method where, after the above-described waveform indicating the hypnagogic symptom phenomenon appears, the waveform shows a convergence tendency and thereafter shows a variation fluctuation with a longer cycle.

Figure 8:
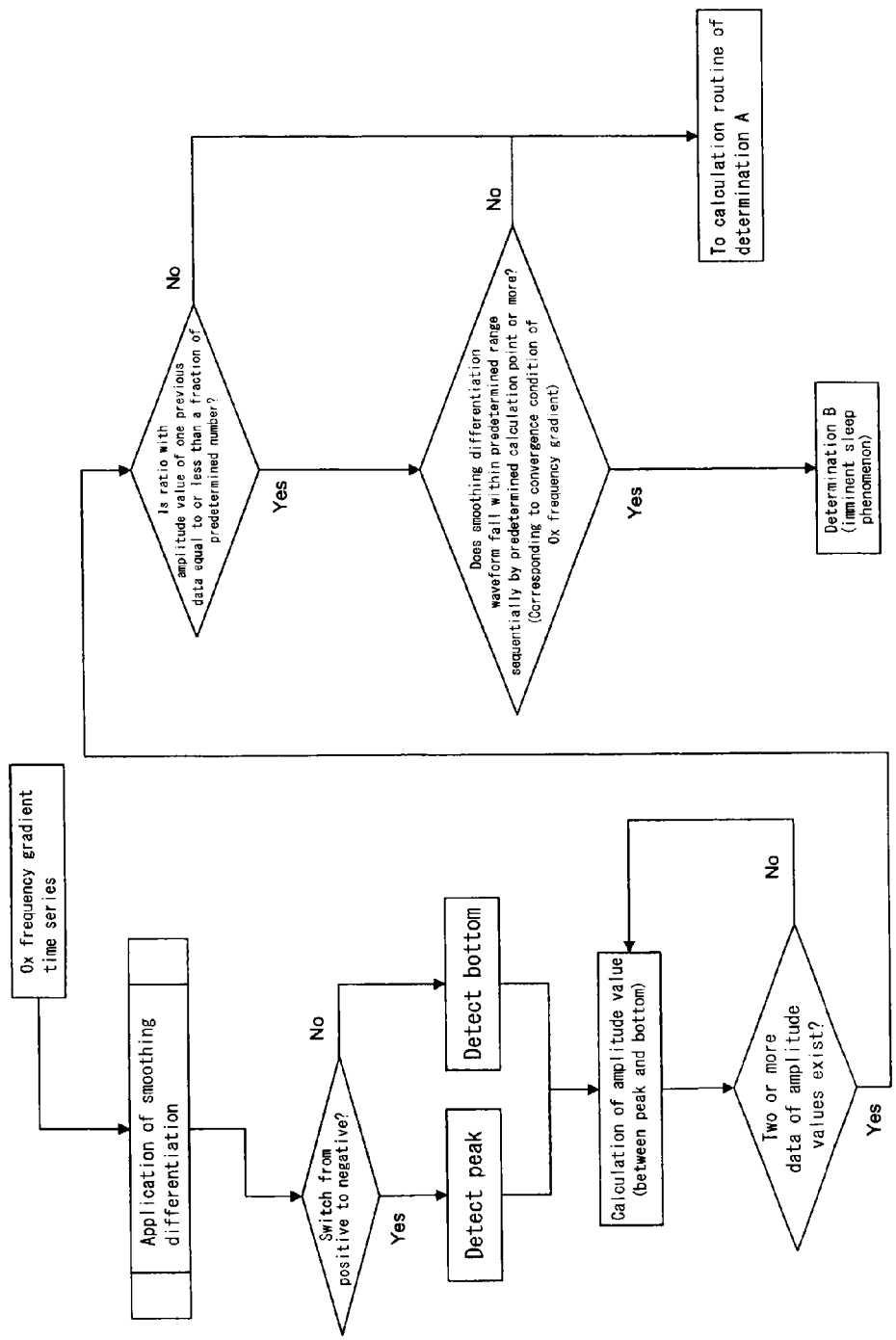
FIG. 8 is a flowchart for explaining a determination step of an imminent sleep phenomenon.

In FIG. 6C, the imminent sleep phenomenon is identified from 29 to 38 minutes and occurs several minutes before determination of the falling asleep point by brain wave. Upon identifying the imminent sleep phenomenon in real time, in this embodiment, determination as described in FIG. 8 is performed. Specifically, the frequency gradient time series waveform using the zero cross detection method is subjected to smoothing differentiation, a point of switching from positive gradient to negative gradient is detected as a peak, a point of switching from negative gradient to positive gradient is detected as a bottom, and an amplitude value between the both is calculated. Next, whether a plurality of such amplitude values exist or not is obtained, and if a plurality of them exist, a comparison of magnitude with the amplitude value of one previous data piece is made. If the ratio of the magnitude is equal to or less than a fraction of a predetermined number, and a value of smoothing differentiation waveform falls within a predetermined range sequentially by a predetermined calculation point or more and indicates a tendency of convergence and thereafter accompanies a variation fluctuation with a longer cycle, it is determined as the imminent sleep phenomenon.

The hypnagogic symptom phenomenon detecting means 621 and the imminent sleep phenomenon detecting means 622 of this embodiment also have a means determining a biological state of the driver, which is difficult to recognize, including the hypnagogic symptom phenomenon or the imminent sleep phenomenon by a predetermined determination criterion, by using at least one of respective distribution rates at arbitrary points on the time axis of three frequency components corresponding to the function adjusting signal, the fatigue reception signal and the activity adjusting signal obtained by the distribution rate calculating means 614 and the degree of change of one of the frequency components obtained by the degree of change calculating means 615. The function adjusting signal, the fatigue reception signal and the activity adjusting signal are frequency components lower than 0.01 Hz belonging in the ULF band to the VLF band, and they are associated with the state of body temperature control. This body temperature control reflects a result of autonomic nerve control, and thus the hypnagogic symptom phenomenon and the imminent sleep phenomenon can be grasped by determining the distribution rates and the degrees of change of frequency components of the ultralow frequency/very low frequency by predetermined determination criteria.

Figure 9:
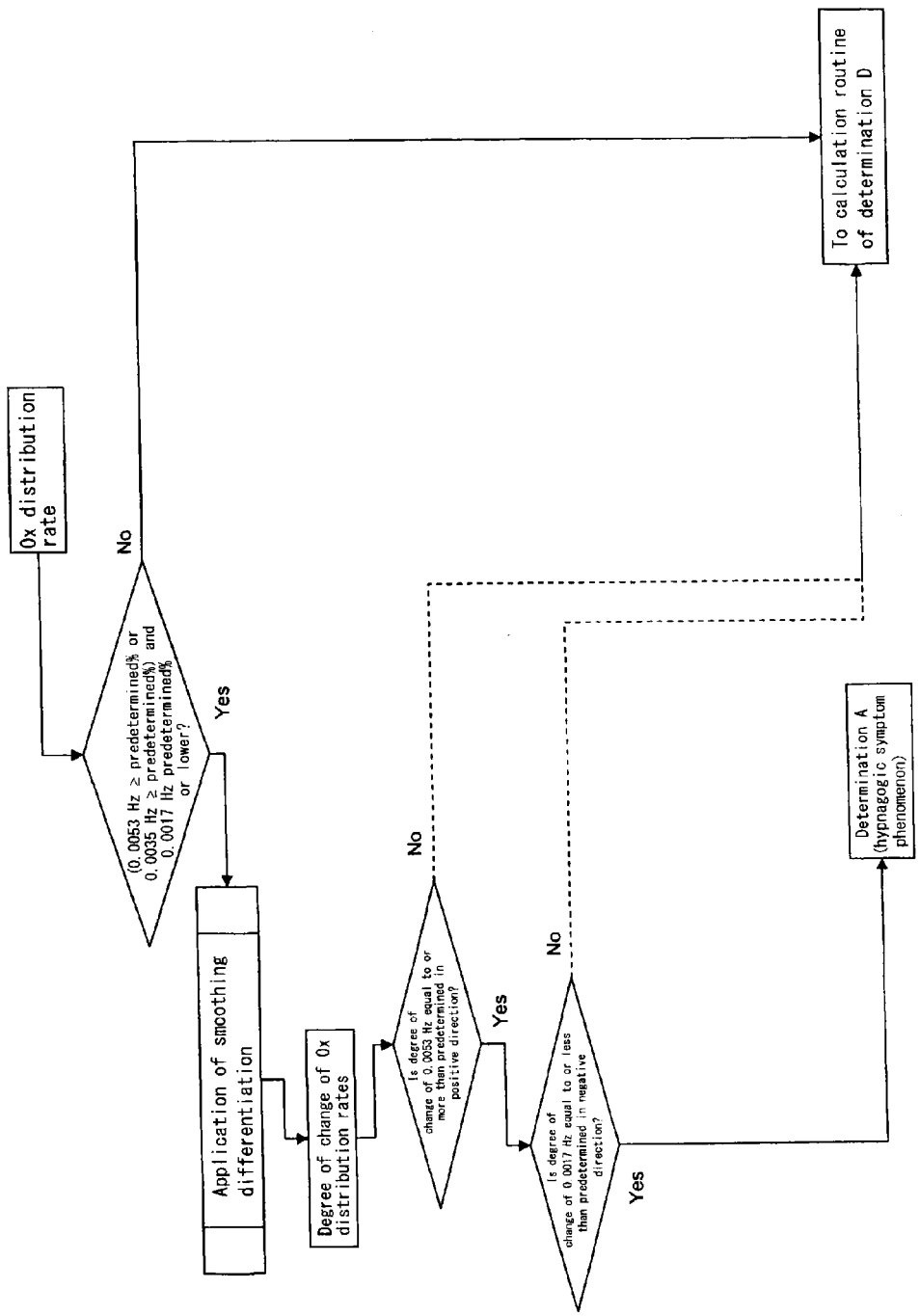
FIG. 9 is a flowchart for explaining a determination step of the hypnagogic symptom phenomenon.

First, regarding the hypnagogic symptom phenomenon, as illustrated in FIG. 9, whether or not the activity adjusting signal (0.0053 Hz) or the fatigue reception signal (0.0035 Hz) is equal to or higher than a predetermined value and the function adjusting signal (0.0017 Hz) is lower than them is determined from among time series waveforms of distribution rates using the zero cross detection method. This is determination focusing on that the hypnagogic symptom phenomenon is such that fatigue has been accumulated and then temporary increase in the sympathetic function occurs, and thus increase in distribution rates of the activity adjusting signal and the fatigue reception signal related to them occurs. In order to grasp such a change more accurately, in this embodiment, the degree of change obtained by the degree of change calculating means 615 is considered to perform determination. That is, when it is determined that the time series changes of distribution rates satisfy the above conditions, it is determined whether or not the degree of change of the activity adjusting signal (0.0053 Hz) is equal to or more than a predetermined value in the positive direction and whether or not the function adjusting signal (0.0017 Hz) is equal to or less than a predetermined value in the negative direction, that is, whether or not the manner of changing is larger than a predetermined value and is simultaneously changing in a positive-negative reverse direction.

Also regarding the imminent sleep phenomenon, it likewise occurs as a result of accumulation of fatigue, and there occurs an increase in the parasympathetic function before reaching the falling asleep point, leading the person to a more relaxed state. In the case of the imminent sleep phenomenon, after the hypnagogic symptom phenomenon appears, it becomes a state that the parasympathetic function is predominant. Thus, a fluctuation controlling the heartbeat fluctuation changes, which appears in the zero cross detection method, and the heartbeat fluctuation itself changes (frequency of heartbeat tends to be low) appearing in the peak detection method and occurring due to the predominance of the parasympathetic nerve system. Therefore, both the distribution rate using the zero cross detection method and the distribution rate using the peak detection method are used to detect whether a change of the activity adjusting signal (0.0053 Hz) in particular appears significantly or not. Further, in order to further increase determination accuracy, being the imminent sleep phenomenon is determined in both the distribution rate using the zero cross detection method and the distribution rate using the peak detection method, and only when determination of the both is within a defined time, it is finally determined and outputted as the imminent sleep phenomenon.

Figure 10:
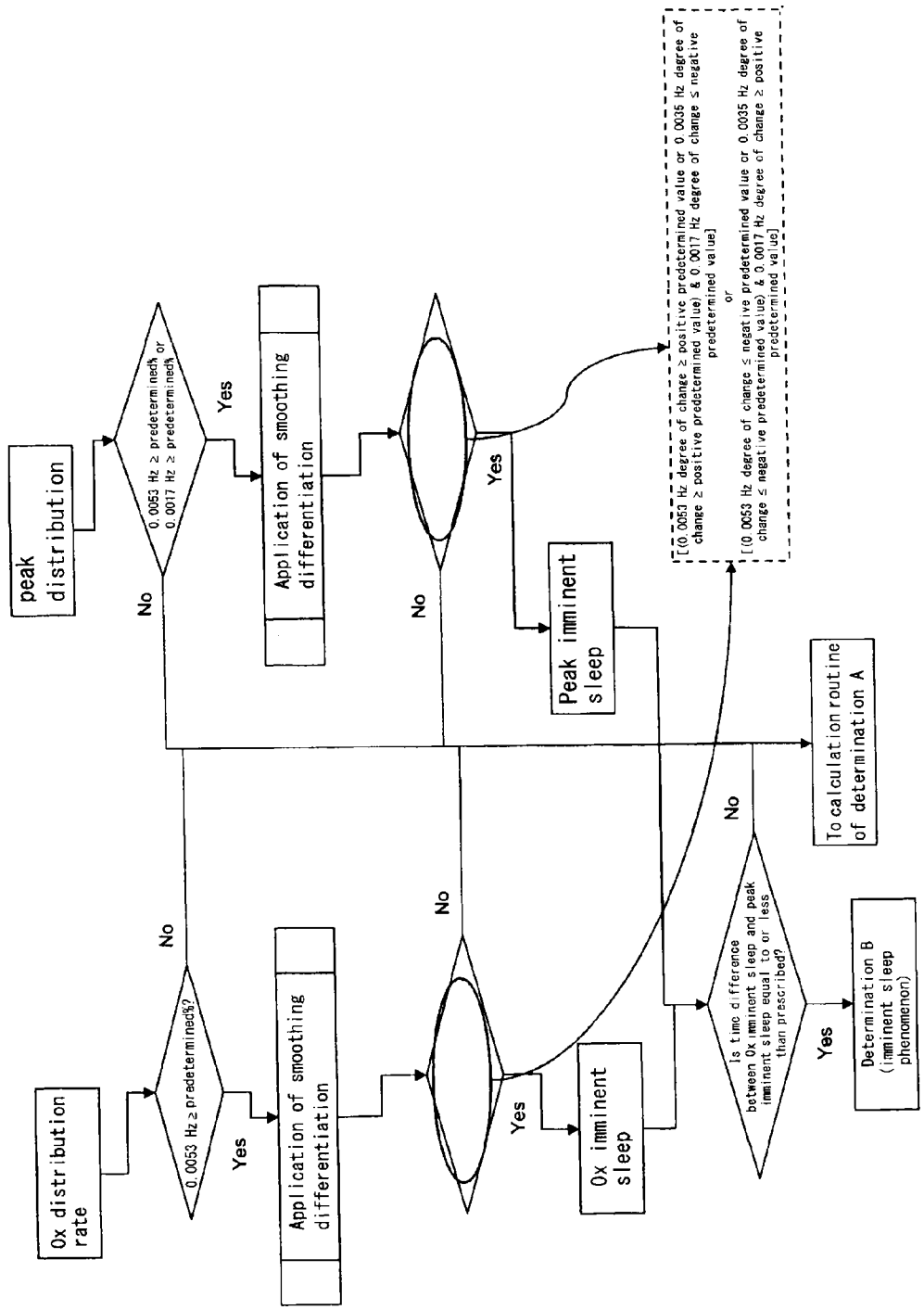
FIG. 10 is a flowchart for explaining a determination step of the imminent sleep phenomenon.

Specifically, it is as described in FIG. 10, first, by the zero cross detection method, in the distribution rate, the case where the activity adjusting signal (0.0053 Hz) is equal to or higher than a predetermined value, the degree of change of the activity adjusting signal (0.0053 Hz) or the fatigue reception signal (0.0035 Hz) is larger than a predetermined value in the positive or negative direction, and the degree of change of the function adjusting signal (0.0017 Hz) is larger than a predetermined value in the positive-negative reverse direction of them, is determined as the imminent sleep. By the peak detection method, in the distribution rate, the case where the activity adjusting signal (0.0053 Hz) or the function adjusting signal (0.0017 Hz) is equal to or higher than a predetermined value, the degree of change of the activity adjusting signal (0.0053 Hz) or the fatigue reception signal (0.0035 Hz) is larger than a predetermined value in the positive or negative direction, and the degree of change of the function adjusting signal (0.0017 Hz) is larger than a predetermined value in the positive-negative reverse direction of them, is determined as the imminent sleep. Then, when the imminent sleep is determined in the determination result using the distribution rate by the zero cross detection method, the imminent sleep is determined in the determination result using the distribution rate by the peak detection method, and these determinations are within a defined time, that is, when similar changes occur in the zero cross detection method and the peak detection method around the same time, it is finally determined and outputted as the imminent sleep phenomenon.

As described above, the hypnagogic symptom phenomenon detecting means 621 and the imminent sleep phenomenon detecting means 622 have two determination methods, a method of determining the hypnagogic symptom phenomenon as a biological state which is difficult to be aware of, and the imminent sleep phenomenon as a biological state which is basically difficult to be aware of but can be recognized in some cases, with predetermined criteria by using the frequency gradient time series waveform, and a method of determining them with predetermined criteria by using the distribution rates of the function adjusting signal (0.0017 Hz), the fatigue reception signal (0.0035 Hz) and the activity adjusting signal (0.0053 Hz), and detect the hypnagogic symptom phenomenon and the imminent sleep phenomenon by them. Therefore, it can be said that they can securely detect these biological states, are highly reliable, and are suitable as determination methods of biological state during driving. Note that when the hypnagogic symptom phenomenon and the imminent sleep phenomenon are detected, the hypnagogic symptom phenomenon detecting means 621 and the imminent sleep phenomenon detecting means 622 have a control function to perform output notifying the driver of this (display on a monitor, generation of warning, vibration of the driver's seat, and so on). In this case, the hypnagogic symptom phenomenon detecting means 621 and the imminent sleep phenomenon detecting means 622 may be set to transmit the detection result constantly or periodically to a management computer via a communication line. Of course, after the operation is finished, these data may be analyzed by a management computer. Note that when it is set thus, the management computer consequently forms a part of the device for determining biological state during driving of the present invention.

The subjective sleepiness/low consciousness traveling state detecting means 623 is a means detecting a subjective sleepiness which is a physical condition change phenomenon before falling asleep accompanying a subjective sleepiness of the driver, and a low consciousness traveling state which occurs due to a decrease in consciousness level, by using a calculation result of the analyzing and calculating means 61. The "subjective sleepiness" mentioned here refers to a symptom which can be subjectively conscious of among symptoms indicating a physical condition change, and refers to a light sleepiness (mild sleepiness) felt during driving, an unbearably strong sleepiness which occurs as the driving time becomes long, or a strong sleepiness which occurs due to rebound from a state of excessive tension, or the like. Further, the "low consciousness traveling state" refers to a traveling state in which, as described above, despite being in neither a sleep deprivation state nor an overfatigue state and in a good mental and physical condition, the driver keeps traveling in a state of being unable to read or judge information even though the sleepiness is not subjective and eyes are open due to a significant decrease in consciousness level during driving, and the driver falls in such state momentarily for two to three seconds. This state is in common to the light sleepiness in that it momentarily indicates a significant decrease in attention, and is conceivable to indicate a biological reaction similar to when a light subjective sleepiness is felt. Further, when such a momentary "low consciousness traveling state" occurs sequentially ("sequentially" mentioned here includes the case where it occurs intermittently within a predetermined time, or the case of falling in the low consciousness traveling state for a long time of three seconds or more, and the like, besides the case where the momentary low consciousness traveling state continues), it is conceivable to indicate a biological reaction similar to when being aware of an unbearable strong sleepiness. Further, a period of being aware of sleepiness and a period of being fallen in the low consciousness traveling state are conceivably a period in which the homeostasis function of the driver himself or herself is such that an intention to return from this state to a wakeful state potentially operates, and moreover are in common in that, because a responding ratio to sound until reaching a sleep stage 1 is 0.9 to 1, it is possible to return easily to a state of high consciousness level, a state that an attention can be called, or even the wakeful state if any kind of warning is provided. On the other hand, the hypnagogic symptom and imminent sleep phenomenon can be distinguished from the subjective sleepiness and the low consciousness traveling state in that they can be said as a biological reaction as, so to speak, a preliminary stage to sleep.

Accordingly, in this embodiment, the "subjective sleepiness" and the "low consciousness traveling state" are detected without being distinguished. The "subjective sleepiness" and the "low consciousness traveling state" are closely associated with changes in frequency components less than 0.01 Hz belonging in the ULF band to the VLF band reflecting the body temperature adjusting function, particularly the function adjusting signal around 0.0017 Hz, the fatigue reception signal around 0.0035 Hz and the activity adjusting signal around 0.0053 Hz. Therefore, the subjective sleepiness/low consciousness traveling state detecting means 623 determines by using the distribution rates of the respective frequency components obtained by the distribution rate calculating means 614 and a calculation result of at least one of the degrees of change of the respective frequency components by the degree of change calculating means 615.

The subjective sleepiness/low consciousness traveling state detecting means 623 includes a means determining an occurrence of the light sleepiness (mild sleepiness) which disappears by yawning or the momentary low consciousness traveling state for two to three seconds or less (first subjective sleepiness/low consciousness traveling state detecting means 623a) and a means determining whether or not the driver has gone beyond the range of mild sleepiness and is in a strong sleepiness state which occurs by long-time driving or rebound to a state of excessive tension as described above, or whether or not the momentary low consciousness traveling state occurs continuously or intermittently within a predetermined time or the driver has fallen into the low consciousness traveling state for a longer time (second subjective sleepiness/low consciousness traveling state detecting means 623b).

The first subjective sleepiness/low consciousness traveling state detecting means 623a determines appearance of the mild sleepiness or the momentary low consciousness traveling state on a condition that, among the three frequency components obtained by the distribution rate calculating means 614, the distribution rate of the frequency component corresponding to the activity adjusting signal indicates a change to be equal to or lower than the distribution rate of the frequency component corresponding to the function adjusting signal. As described above, the hypnagogic symptom phenomenon and the imminent sleep phenomenon are based on detection of an emergent rise in the sympathetic function in the course of change to be parasympathetic nerve predominant, but the mild sleepiness or the momentary low consciousness traveling state appears in a timing of decrease in consciousness level without the person being aware of it, such that accompanying fatigue, the distribution rate of the function adjusting signal (0.0017 Hz) controlling modulation or functional decrease of a body relatively increases, and conversely the distribution rate of the activity adjusting signal (0.0053 Hz) relatively decreases.

When such a relative increase in distribution rate of the function adjusting signal (0.0017 Hz) and a relative decrease in distribution rate of the activity adjusting signal (0.0053 Hz) are replaced with degrees of change, it is a timing when the distribution rates of the function adjusting signal and the activity adjusting signal indicate relatively large changes. Thus, at this point, the degrees of change of both the frequency components are each equal to or larger than a predetermined value in absolute value.

That is, it is determined that a physical condition change accompanying the mild sleepiness or the momentary low consciousness traveling state is included in timings satisfying these conditions. However, in this embodiment, in addition to this logical condition, conditions obtained statistically based on numerous experimental results are combined to set the determination condition of the first subjective sleepiness/low consciousness traveling state detecting means 623a, thereby enabling more accurate determination of the mild sleepiness or the momentary low consciousness traveling state.

On the other hand, while setting statistic conditions of the mild sleepiness or the momentary low consciousness traveling state, it is found that when the determination criteria of whether or not it is the mild sleepiness or the momentary low consciousness traveling state are divided roughly in two, the determination accuracy increases further. This is such that the determination criteria are largely separated depending on whether the basic state of the driver as a determination target is a relaxed state or a state of tension (including an excited state). The relaxed state is, for example, the case where the sympathetic nervous system and the parasympathetic nervous system are well balanced, such as the case where a person is relaxed while driving on a familiar road alone, the case of a professional driver accustomed to long-distance driving and skilled in relaxing while driving, or the like. The state of tension (including an excited state) is the case where the sympathetic function is rising when, for example, there is a passenger and driving is performed while having a conversation, or the like.

Figure 11:
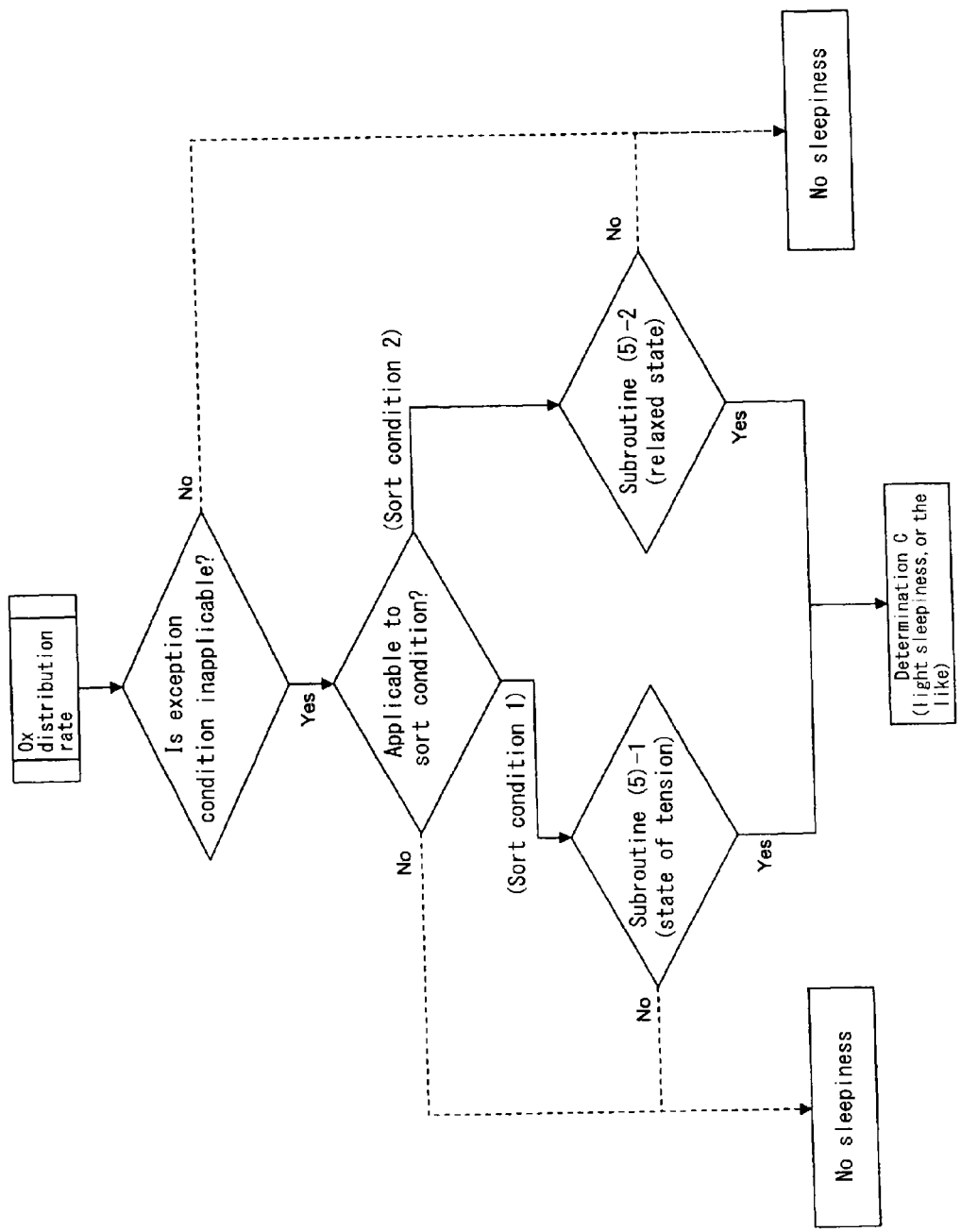

Further, whether the relaxed state or the state of tension (including an excited state) changes due to road conditions, timing of break, music in the vehicle, getting on or off of passenger, or the like in a long-time driving environment. Therefore, the first subjective sleepiness/low consciousness traveling state detecting means 623a determines whether the driver is constantly in a relaxed state or not and thereby changes thresholds of determination criteria for the mild sleepiness or the momentary low consciousness traveling state for performing determination. Determination of whether the basic state is the relaxed state or the state of tension (including an excited state) is performed by using the distribution rates obtained from the distribution rate calculating means 614 and the degrees of change obtained from the degree of change calculating means 615. Specifically, as illustrated in FIG. 11, numerous experimental results are statistically processed, the distribution rates and the degrees of change of the function adjusting signal (0.0017 Hz), the fatigue reception signal (0.0035 Hz) and the activity adjusting signal (0.0053 Hz) and a timing when there is conceivably a possibility that the mild sleepiness or the momentary low consciousness traveling state occurred in the driver are compared (self-declaration or observation by a passenger), a condition that the mild sleepiness or the momentary low consciousness traveling state has not occur (exception condition) is set, and sort conditions are set to, at a timing when there is a possibility that the mild sleepiness or the momentary low consciousness traveling state occurred, distinguish it as the state of tension (including an excited state) (sort condition 1) or the relaxed state (sort condition 2) from the driving environment at this time of the driver (presence of passenger, presence of in-vehicle music, condition of traffic jam, or the like). Note that when the exception condition is applicable or when it is not applicable to the sort conditions, it is determined as no sleepiness.

Figure 12:
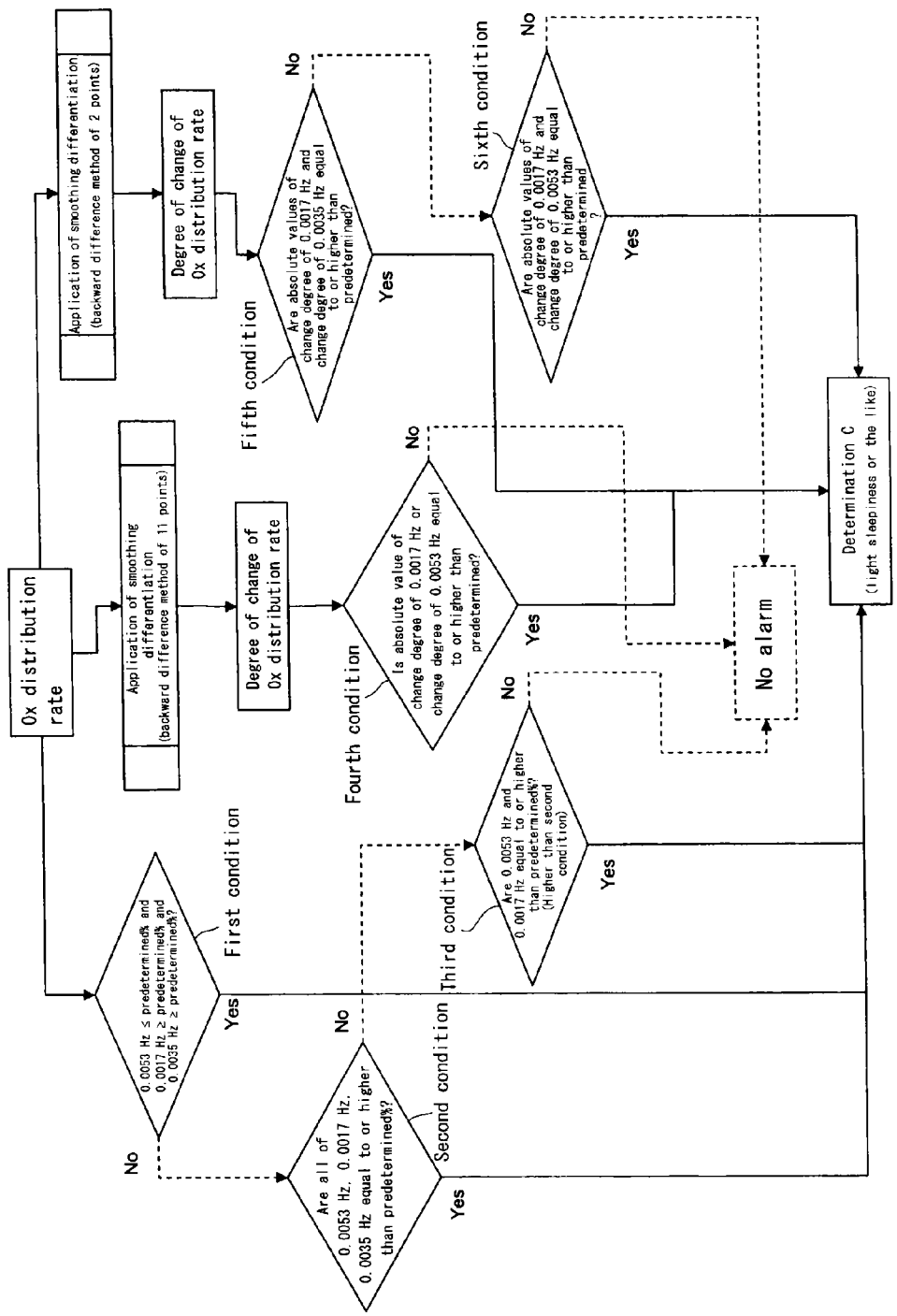

From these facts, the first subjective sleepiness/low consciousness traveling state detecting means 623a of this embodiment first performs classification into one for which the determination criterion of the relaxed state is used or one for which the determination criterion of the state of tension (including an excited state) is used according to the above-described sort conditions, in the case of not falling under the above-described exception condition, by using the distribution rates obtained from the distribution rate calculating means 614 using the zero cross detection method. After classification, it is determined whether or not the distribution rate of the function adjusting signal (0.0017 Hz) in the time zone of this determination target is equal to or higher than a predetermined value and the distribution rate of the activity adjusting signal (0.0053 Hz) is equal to or lower than the predetermined value. FIG. 12 illustrates one example of a determination flow.

First, it is determined as the mild sleepiness when the distribution rate of the activity adjusting signal (0.0053 Hz) is equal to or lower than a predetermined value and the function adjusting signal (0.0017 Hz) is equal to or higher than a predetermined value exceeding this value in the time series waveforms of distribution rates (first condition). Even when the first condition is not satisfied, it is determined as the mild sleepiness when all the distribution rates of the function adjusting signal (0.0017 Hz), the fatigue reception signal (0.0035 Hz) and the activity adjusting signal (0.0053 Hz) are equal to or higher than a predetermined value (second condition), and moreover, even when the first condition and the second condition are not satisfied, it is determined as the mild sleepiness or the momentary low consciousness traveling state when the distribution rates of the function adjusting signal (0.0017 Hz) and the activity adjusting signal (0.0053 Hz) are values higher than the set value of the second condition (third condition).

Next, when the degrees of change are used, the degrees of change are obtained respectively in the case where smoothing differentiation is applied at a different number of calculation points, for example 11 points, and the case where smoothing differentiation at two points is applied, and an appropriate threshold is set in each of the cases, so as to perform determination. For example, when the smoothing differentiation at 11 points is applied, it is determined as the mild sleepiness or the momentary low consciousness traveling state when absolute values of the degrees of change of the function adjusting signal (0.0017 Hz) and the activity adjusting signal (0.0053 Hz) are equal to or larger than a predetermined value (fourth condition). In the case where the smoothing differentiation at two points is used, it is determined as the mild sleepiness or the momentary low consciousness traveling state when the absolute values of the degrees of change of the function adjusting signal (0.0017 Hz) and the fatigue reception signal (0.0035 Hz) are equal to or larger than a predetermined value (fifth condition), or if the fifth condition is not satisfied, it is determined as the mild sleepiness or the momentary low consciousness traveling state when the absolute values of the degrees of change of the function adjusting signal (0.0017 Hz) and the activity adjusting signal (0.0053 Hz) are equal to or larger than a predetermined value (sixth condition).

The first subjective sleepiness/low consciousness traveling state detecting means 623a is, because it thus determines by using the distribution rates and the degrees of change of the function adjusting signal (0.0017 Hz), the fatigue reception signal (0.0035 Hz) and the activity adjusting signal (0.0053 Hz) related to body temperature control, able to accurately determine the mild sleepiness or the momentary low consciousness traveling state which are recognizable physical condition changes, and is suitable for biological state determination during driving.

The second subjective sleepiness/low consciousness traveling state detecting means 623b is a means determining, as described above, whether or not it exceeds the range of the mild sleepiness and has fallen in the strong sleep state occurring due to long-time driving or rebound from the state of excessive tension, or whether or not the momentary low consciousness traveling state has occurred continuously within a predetermined time (including the case of occurring intermittently and the case of falling in the low consciousness traveling state for a longer time).

Figure 13:
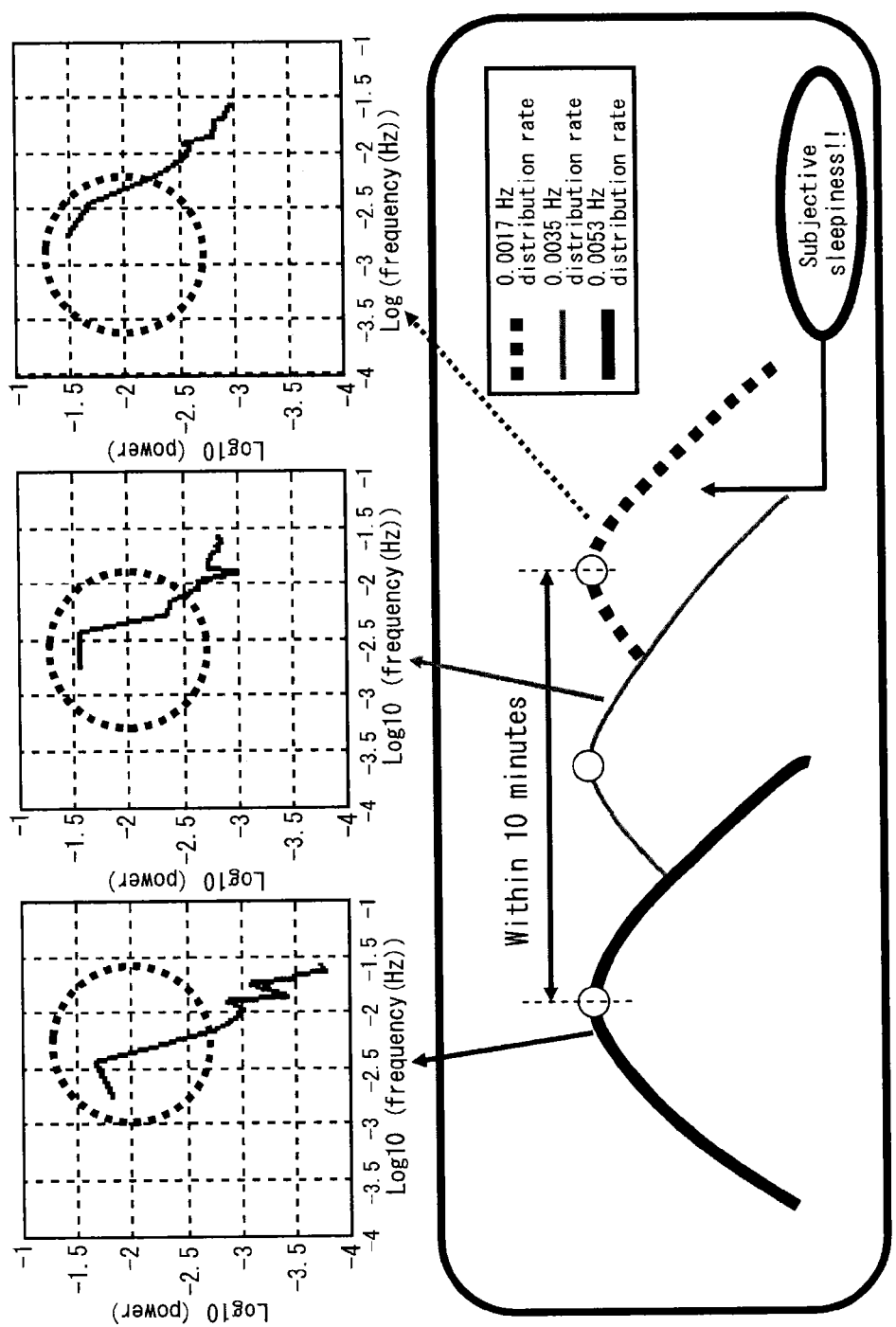

The driving involves physical labor such as maintaining a predetermined seating posture, steering or pedal operation and mental labor such as repetitively collecting various information and making a decision instantly while traveling. Accordingly, in the long time driving, not only fatigue accumulates but also either of physical activity and mental activity decrease in activity frequency because traveling is at a constant speed in the long time driving on an express way or the like, and a strong sleepiness can occur, the low consciousness traveling state occurs repetitively within a predetermined time or the time of one low consciousness traveling state becomes longer (three seconds or more for example). More specifically, when sleepiness such as desiring to sleep occurs, the body prepares to resist the sleepiness by making the sympathetic nerve activity rise. As a result, the distribution rate of the activity adjusting signal (0.0053 Hz) increases. Next, the sleepiness induces a tension and an attempt to be in a concentrated state is made, the distribution rate of the function adjusting signal (0.0017 Hz) increases, and moreover, if it becomes difficult to resist the sleepiness the parasympathetic nerve activity is activated and attempts to guide the body to rest. Thus, the distribution rate of the fatigue reception signal (0.0035 Hz) reflecting the parasympathetic nerve activity changes to increase. Through such processes, a non-subjective desire to sleep which occurred in the body (non-subjective sleepiness) switches to a subjective sleepiness, which is a subjective desire to sleep which occurred in the body. FIG. 13 is a diagram schematically illustrating this change, and many subjects exhibited such a transition of change such as when a strong sleepiness actually occurs from many experimental results.

Accordingly, the second subjective sleepiness/low consciousness traveling state detecting means 623b is set to determine that it has become the state of resisting the strong sleepiness or the continuous (including the case of occurring intermittently within a predetermined time or the case of continuing for a longer time) low consciousness traveling state when respective peak values of the time series waveforms of the distribution rates of the above three frequency components obtained by the distribution rate calculating means 614 are values which appear in a predetermined order within a range of difference in predetermined appearance time, and satisfy a predetermined distribution rate condition.

Figure 14:
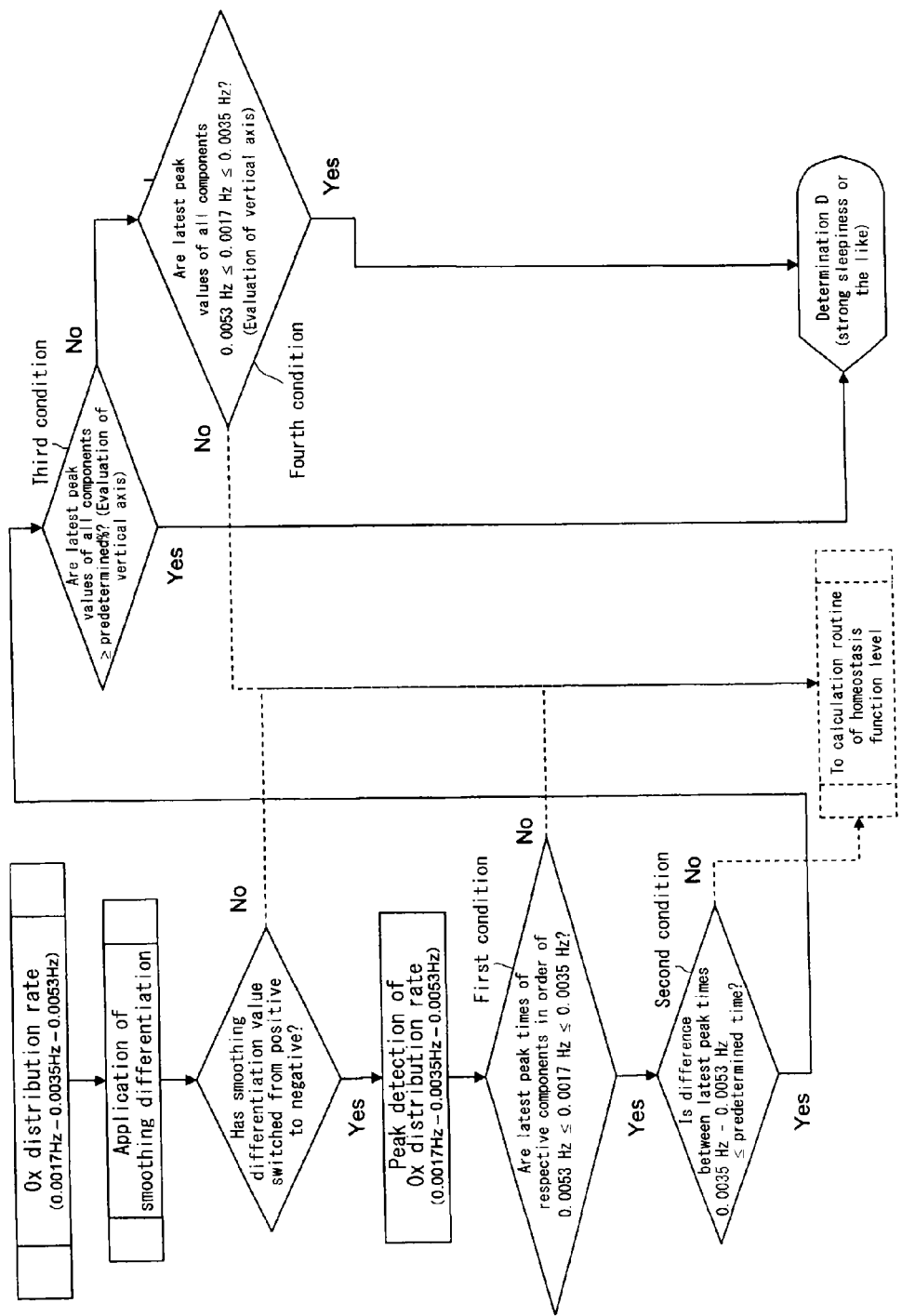

Specifically, as illustrated in FIG. 14, it is determined that it has become the state of resisting the strong sleepiness or the continuous (including the case of occurring intermittently within a predetermined time or the case of continuing for a longer time) low consciousness traveling state when appearance times of the peak values of distribution rates of the function adjusting signal (0.0017 Hz), the fatigue reception signal (0.0035 Hz) and the activity adjusting signal (0.0053 Hz) satisfy the following relation: activity adjusting signal≤function adjusting signal≤fatigue reception signal (first condition), a difference in the appearance times of peak values of the activity adjusting signal and the fatigue reception signal is within a predetermined time (second condition), and moreover a condition that all the frequency components are equal to or higher than a predetermined distribution rate is satisfied (third condition). Further, if none of the frequency components satisfies the condition that all the frequency components are equal to or higher than a predetermined distribution rate, that is, the first condition and the second condition are satisfied but the third condition is not satisfied, a preferred structure is to determine that it has become the state of resisting the strong sleepiness or the continuous (including the case of occurring intermittently within a predetermined time or the case of continuing for a longer time) low consciousness traveling state when the peak values of the respective distribution rates satisfy a condition, activity adjusting signal ≤function adjusting signal≤fatigue reception signal (fourth condition).

On the other hand, it is conceivable that the mechanism for the subjective sleepiness to occur, as described above, passes through a rise in the sympathetic nerve activity (increase in the distribution rate of the activity adjusting signal (0.0053 Hz)), shift to a state of tension/concentration (increase in the distribution rate of the function adjusting signal (0.0017 Hz)), and activation of the parasympathetic nerve activity (increase in the fatigue reception signal (0.0035 Hz)), but as a result of experiment, occasionally there are cases where a strong subjective sleepiness occurs without passing through this process. Then, the frequency gradient time series waveform in this case was considered, and as illustrated in FIG. 15A, it was found that a convergence tendency of amplitude is detected with respect to a predetermined criterion, and the cycle becomes a short cycle. Specifically, the amplitude decreases and the cycle becomes a short cycle from about 300 seconds to about 200 seconds. This corresponds to the frequency components of 0.0035 Hz, 0.0053 Hz, and it is conceivably difficult for 0.0017 Hz to be predominant. That is, it is conceivable that after the sympathetic nerve activity rises for resisting sleepiness, the state becomes like giving up and the parasympathetic nerve activity is activated, and subsequently the sympathetic nerve activity decreases and a strong sleepiness is felt.

FIG. 15B is a diagram illustrating results of a chi-squared test when only the distribution rates of the three frequency components by the distribution rate calculating means 614 are used for detecting the subjective sleepiness (data of dynamic experiment 89 examples of experimental example 1, which will be described later), where there were 23 non-detection cases and a correct answer rate was 77%. Accordingly, when the case where the amplitude value is in a predetermined set range in the frequency gradient time series waveform and the cycle becomes a short cycle in a predetermined set range is also detected as the strong subjective sleepiness, as illustrated in FIG. 15C, there were four non-detection cases and the detection accuracy increased. Therefore, it can be said that, upon detecting the strong sleepiness, the second subjective sleepiness/low consciousness traveling state detecting means 623b is preferred to use determination by the frequency gradient time series waveform in addition to the above determination by the distribution rates.

When the subjective sleepiness or the low consciousness traveling state is detected, similarly to the hypnagogic symptom phenomenon detecting means 621 and the imminent sleep phenomenon detecting means 622, the subjective sleepiness/low consciousness traveling state detecting means 623 has a control function to give a warning to inform the driver of it (display on the monitor, generation of warning sound, vibration of the driver's seat, or the like). In particular, the subjective sleepiness and the low consciousness traveling state are a state of decreased attention due to a sleepiness or a decrease in consciousness level as described above, and by reliably giving a warning of them, returning to the wakeful state is easily prompted. Further, as described above, the subjective sleepiness and the low consciousness traveling state are a stage before reaching the sleep stage 1 and the responding ratio to sound is 0.9 to 1, and thus particularly a warning with sound is preferred. The subjective sleepiness/low consciousness traveling state detecting means 623 may be set to transmit, similarly to the hypnagogic symptom phenomenon detecting means 621 and the imminent sleep phenomenon detecting means 622, its detection result constantly or periodically to a management computer via a communication line, and these data may be analyzed by the management computer after the operation is finished.

According to this embodiment, the subjective sleepiness/low consciousness traveling state detecting means 623 is included in addition to the hypnagogic symptom phenomenon detecting means 621 and the imminent sleep phenomenon detecting means 622. That is, in addition to that a biological state which is difficult to recognize, such as the hypnagogic symptom phenomenon and the imminent sleep phenomenon (including, of course besides the case of being non-subjective at all, a state that recovery to wakefulness has become impossible when it becomes subjective) can be detected, a recognizable biological state which is a state of resisting the mild sleepiness or the strong sleepiness and can be said as unqualified for driving can be detected, and the momentary low consciousness traveling state or the continuous low consciousness traveling state can be detected. Specifically, in general, the subjective sleepiness easily occurs when driving under overfatigue or sleep deprivation, and thereafter, the hypnagogic symptom phenomenon is detected, the imminent sleep to phenomenon is further detected, and in these states if a warning is issued but it is not possible to return to the wakeful state, the driver enters a drive dozing. On the other hand, when driving in good mental and physical conditions, it is easier to fall into the low consciousness traveling state than the subjective sleepiness, the low consciousness traveling state becomes continuous one from momentary one by a long-time constant traveling on an expressway or the like. As this is repeated, a negative feedback is applied in this state, that is, control in a different dimension of the endocrine system takes place to thereby cause the hypnagogic symptom phenomenon to emerge, and the imminent sleep phenomenon as a state of end period thereof is detected, entering the drive dozing similarly to the above. Further, there are also cases where the subjective sleepiness and the low consciousness traveling state are combined and repeated, and soon the hypnagogic symptom phenomenon or the imminent sleep phenomenon is detected. Of course, depending on the physical condition of the driver, or the like, the hypnagogic symptom phenomenon or the imminent sleep phenomenon is not always detected after a detection timing of the subjective sleepiness or the low consciousness traveling state, and can also emerge earlier.

That is, according to this embodiment, having the subjective sleepiness/low consciousness traveling state detecting means 623 in addition to the hypnagogic symptom phenomenon detecting means 621 and the imminent sleep phenomenon detecting means 622, a biological state change to be undergone before falling into a doze can be grasped in any pattern, making it suitable as a device for grasping a biological state during driving.

Next, the homeostasis function level determining means 624 will be described. The homeostasis function level determining means 624 is such that, when information of the time series waveform of the APW is obtained for a predetermined time or longer by the biosignal measuring device 1 after the device for determining biological state during driving 60 of this embodiment is activated, it is outputted by displaying on an onboard monitor, or the like. The homeostasis function level determining means 624 determines the level of the homeostasis function. The level of the homeostasis function is, for example, divided in five to seven stages, and determines from the case where the homeostasis function is excellent (when the physical condition is good or the degree of concentration is high, or the like) to the case where the homeostasis function is inferior (when the physical condition is bad, when in the state of excessive tension, a decrease in concentration by inattentive driving, or the like) (see FIG. 27A and FIG. 28A). Upon displaying on the monitor, if the levels in five to seven stages are displayed by texts, they are difficult to be comprehended by the driver. Accordingly, for example, when the cases of intermediate level (the physical condition is in a normal state) or higher are collectively determined as the case where the homeostasis function is excellent (the case where the physical condition is good, or the like), the cases lower than them are collectively determined as the case where the homeostasis function is inferior (the case where the physical condition is bad, or the like), and they are displayed on the monitor by different color display, they can be easily comprehended by the driver.

Normally, when the homeostasis function is excellent, on the other side of the physical condition being good, there is a tendency to push oneself too hard to the driving and fall into the low consciousness traveling state, and thus it is important not to be careless. When the homeostasis function is inferior, a caution can be given to the driver of that the subjective sleepiness can easily occur, in addition to the low consciousness traveling state.

The homeostasis function level determining means 624 is based on the technology disclosed in the document WO2011/046178 previously proposed by the applicant, and performs determination by using at least one or more of positive/negative of derivative waveforms of the frequency gradient time series waveform using the zero cross detection method obtained by the frequency gradient calculating means 612 of the analyzing and calculating means 61, positive/negative of derivative waveforms from differentiation of the frequency gradient time series waveforms, absolute values or the like of the respective frequency gradient time series waveforms obtained by absolute value processing of each of the frequency gradient time series waveform using the zero cross detection method and the frequency gradient time series waveform using the peak detection method. By a combination of them, which of them the level of the homeostasis function corresponds to is obtained. For example, the device can be set so that frequency gradients and derivative values are used and when they are equal to or larger than a predetermined value it is determined as "homeostasis function level 1 ", or when the derivative values are equal to or less than predetermined positions and the "peak predominant" among the two absolute values it is determined as "homeostasis function level 4 ". The combination of them and thresholds or the like for determination, and so on are not limited but are determined in this embodiment by statistically processing data of numerous subjects.

Note that setting can also be made by every person. Further, in the homeostasis function level determining means 624, a means calculating a derivative value by absolute value processing of the frequency gradient time series waveform and obtaining this derivative value as a degree of fatigue is also set, as disclosed in the document Japanese Patent Application Laid-open No. 2009-22610 by the present applicant, to thereby output the degree of fatigue of the driver during traveling. For example, it is displayed by changing the color of an image in a predetermined position on the monitor according to the degree of fatigue.

Determination results of the level of the homeostasis function are displayed sequentially on the onboard monitor, or the like, and respective determinations of the hypnagogic symptom phenomenon detecting means 621, the imminent sleep phenomenon detecting means 622, and the subjective sleepiness/low consciousness traveling state detecting means 623 described above are processed in parallel with this and performed sequentially. Therefore, on the monitor, while determination results of the level of the homeostasis function are displayed sequentially, when determination of the hypnagogic symptom phenomenon and the imminent sleep phenomenon, determination of the subjective sleepiness and the low consciousness traveling state are performed, a display indicating them also appears on the monitor. Alternatively, a warning sound is generated, or vibration of the driver's seat or some kind of other warning means operates. Note that it may be set such that the determination results of the level of the homeostasis function by the homeostasis function level determining means 624 are also constantly or periodically transmitted to a management computer via a communication line, and these data may be analyzed by the management computer after the operation is finished.

Figure 27A:
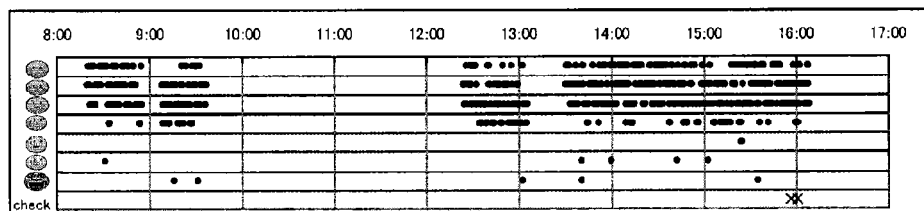
FIGS. 27A to 27D are diagrams illustrating results of a male subject in his thirties in a demonstration experiment during long distance traveling of Experimental Example 4.

The initial fatigue determining means 625 determines presence of initial fatigue of the driver at the start of driving. For determination of the initial fatigue, the determination results in the homeostasis function level determining means 624 are used. The homeostasis function level determining means 624 sequentially determines, as described above, the homeostasis function level (general determination of good/bad of physical condition) of the driver. Accordingly, this determination result is used for determining whether or not the driver is in a state that fatigue is already accumulated at the start of driving. When fatigue is already accumulated at the start of driving, in order to prompt to be particularly cautious of sleepiness of 24-hour cycle by the circadian rhythm, sleepiness of 12-hour cycle by the circasemidian rhythm, and two-hour cycle by the ultradian rhythm, a message or warning to take a rest is outputted at these timings. The presence of initial fatigue is determined as follows. The homeostasis function level in the homeostasis function level determining means 624, and normally the homeostasis function level accompanying a biological fluctuation also, proceed while fluctuating up and down with passage of time. However, when being in a fatigue state, this biological fluctuation also becomes small. Therefore, the homeostasis function level proceeds at any one of the levels, for example, in the state of homeostasis function level 1, the state of homeostasis function level 4, or the like, without change for a predetermined time. Accordingly, when such a state that there is no biological fluctuation continues for a predetermined time, that is, when the same determination level is continuing for a predetermined time or longer, it is determined as the initial fatigue "present". FIG. 27A illustrates an example of this, and the duration of the same homeostasis function level is long since immediately after the start of driving. Therefore, in the case of this subject, when this duration is equal to or more than a set duration, it is determined as the initial fatigue "present".

Note that the initial fatigue determining means 625 is used for determining the presence of initial fatigue of the driver at the start of driving, and determine whether or not it is a state that break after a few hours is particularly needed, and is operated in a driving initial stage (however, in several minutes to ten minutes after the homeostasis function level determining means 624 is activated since it uses the determination results of the homeostasis function level determining means 624).

The determining and detecting means 62 is preferred to further have a feeling determining means 626 and a biological state determining means using history 627, and they function by executing a feeling determining procedure and a biological state determining procedure using history, which are computer programs.

The feeling determining means 626 is a means obtaining an appearance balance of the sympathetic nervous system and the parasympathetic nervous system from an index related to the autonomic nervous system control obtained from the analyzing and calculating means 61 in the driving initial stage until a predetermined time passes after the start of driving, and determining this appearance balance with a predetermined criterion, so as to obtain a biological state of the driver in the driving initial stage.

Figure 16:
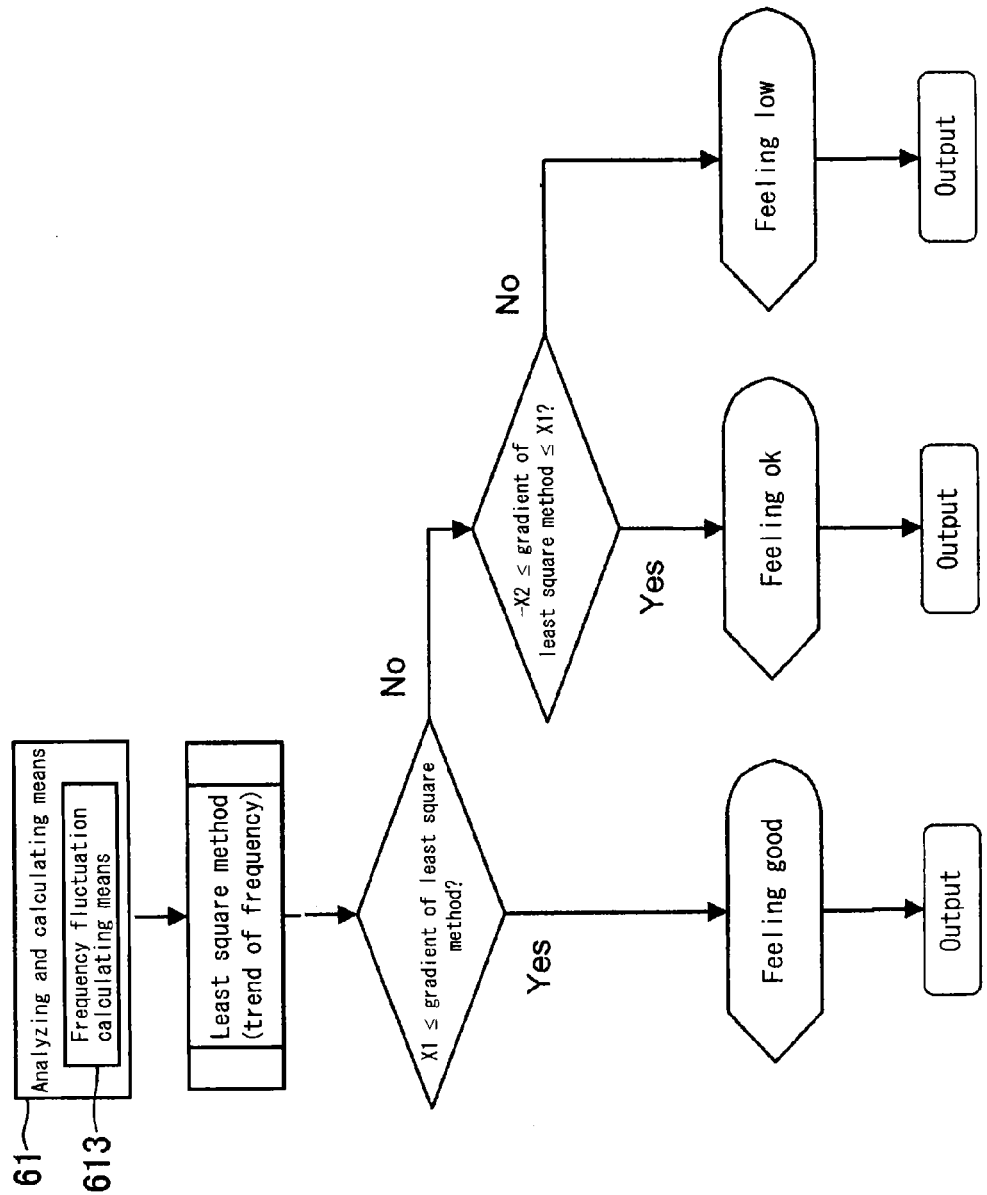
FIG. 16 is a flowchart for explaining a determination step by a feeling determining means.

The hypnagogic symptom phenomenon detecting means 621, the imminent sleep phenomenon detecting means 622, the subjective sleepiness/low consciousness traveling state detecting means 623 and the homeostasis function level determining means 624 described above use the frequency gradient time series waveform, the distribution rates, and so on by the analyzing and calculating means 61, but in order to obtain the frequency gradient time series waveform, the distribution rates, and so on, raw waveform data of the APW for a predetermined time or longer are necessary, and they cannot be obtained unless about several minutes passes after getting in the vehicle. Accordingly, the feeling determining means 626 obtains, as illustrated in FIG. 16, the gradient of a frequency by processing by a least square method the frequency fluctuation time series waveform which is a calculation result of the frequency fluctuation calculating means 613 using the above peak detection method of the analyzing and calculating means 61, and determines with it the appearance balance of the sympathetic function and the parasympathetic function. Specifically, the case where the gradient obtained by the least square method is equal to or larger than a predetermined value (X1) in the positive direction is determined as a state that the sympathetic function has risen (for example, "feeling good"), the case where it is equal to or smaller than a predetermined value (−X2) in the negative direction is determined as a state that the balance between the sympathetic function and the parasympathetic function is bad (for example, "feeling low"), and the case where it is in middle of the both (between −X2 and X1) is determined as a state that the appearance balance between the sympathetic function and the parasympathetic function is achieved (for example, "feeling ok").

The feeling determining means 626 has a function to notify the driver of this "feeling up", "feeling low" or "feeling ok" by outputting it to the monitor, or the like. The driving initial stage accompanies a status change from a non-driving state to being newly placed in a driving environment, and an ability to respond to this driving environment varies from person to person, or even in a same person it varies depending on the physical condition of the present day or the sleeping time of the previous day, or the like and the degree of progress of subsequent fatigue also varies depending on the ability to respond. However, when the driver becomes aware of his or her state at the present time still in a state of tension in the driving initial stage, subsequent improvement in degree of concentration on the driving can be expected. Note that the initial fatigue determining means 625 determines the biological state of the driver at the start of driving by a simple method, and thus operates only in an initial period until a predetermined time passes after the start of driving. Thereafter, changes of the biological sate of the driver are detected sequentially by the hypnagogic symptom phenomenon detecting means 621, the imminent sleep phenomenon detecting means 622, the subjective sleepiness/low consciousness traveling state detecting means 623 and the homeostasis function level determining means 624 described above.

The biological state determining means using history 627 determines the biological state of the driver by using history information as determination results of the hypnagogic symptom phenomenon detecting means 621, the imminent sleep phenomenon detecting means 622, the subjective sleepiness/low consciousness traveling state detecting means 623 and the homeostasis function level determining means 624 described above. Determination results of them are sequentially stored in a storage unit (may be any of a storage unit of an onboard computer and a storage unit of a remote management computer) of the device for determining biological state during driving 60 of this embodiment constituted of a computer, and the biological state determining means using history 627 is structured to sequentially read their information. The biological state determining means using history 627, for example, displays the homeostasis function level in six stages, and among them, when levels 1 to 3 are determined as a normal to a good state, and levels 4 to 6 as a state that requires attention, a history point A (caution point) is added in time series according to the duration of the levels 4 to 6. The homeostasis function level, for example when set to be plotted with one point per several seconds, can be measured by counting the point number at this level. Further, when the hypnagogic symptom phenomenon or the imminent sleep phenomenon is detected by the hypnagogic symptom phenomenon detecting means 622 or the imminent sleep phenomenon detecting means 623, a history point B (cheering point) is added in time series. Moreover, when the subjective sleepiness or the low consciousness traveling state is detected by the subjective sleepiness/low consciousness traveling state detecting means 623, a history point C (warning point) is added in time series (see FIG. 17).

Figure 17:
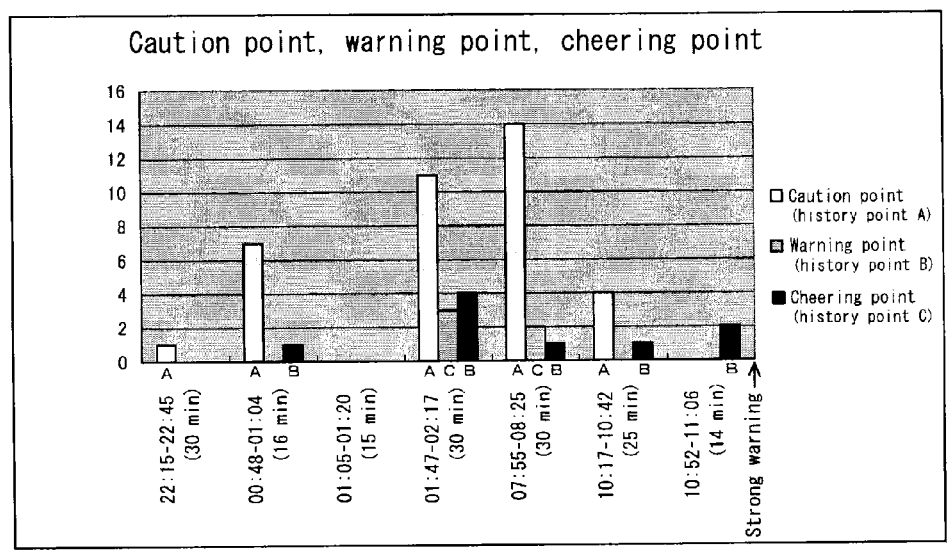
FIG. 17 is a diagram for explaining a detection method of a biological state determining means using history.

Then, when the change in the time series of the history points A to C is in a predetermined state, a warning is outputted separately from the above-described warning when the hypnagogic symptom phenomenon, the imminent sleep phenomenon, the subjective sleepiness or the low consciousness traveling state described above is detected or the warning by a level determination result of the homeostasis function. In what state the warning should be outputted can be set arbitrarily, but for example, as illustrated in FIG. 17, when the history point C based on the determination result of the subjective sleepiness/low consciousness traveling state detecting means 623 increases by a predetermined value or more and moreover the history point B based on the determination results of the hypnagogic symptom phenomenon detecting means 621 and the imminent sleep phenomenon detecting means 622 increases by a predetermined value or more from a state that the history point A at the level of the homeostasis function is many, generally substantial fatigue has accumulated by long time driving and it is conceivable to require a break immediately, and thus it is set to output a strong warning.

As described above, according to this embodiment, the biological state of the driver and a change of the biological state until coming to drive dozing are grasped from multiple aspects (the hypnagogic symptom phenomenon, the imminent sleep phenomenon, the subjective sleepiness, and the low consciousness traveling state). Further, they are constantly checked and the means checking the homeostasis function level implemented conventionally by the present applicant is used together, and information thereof is obtained as history information and the biological state of the driver is determined by using this history information. Therefore, the biological state of the driver can be grasped with higher accuracy than conventional ones, which is preferred for determination of the biological state during driving.

Note that it is possible to make a setting to output the determination result to an onboard device, but it can also be structured to transmit the determination result to a computer of an operation manager via an appropriate communication network, as described above. In this case, the operation manager can grasp the biological state of the driver even when being at a remote location, which helps a more appropriate operation management. Further, in an operation company of trucks, buses, taxis, or the like, after a predetermined operation is completed, the determination results of the driver can further be analyzed. For example, by daily accumulating the above-described determination results, on what conditions this driver reaches the subjective sleepiness, the low consciousness traveling state, the hypnagogic symptom phenomenon, or the imminent sleep phenomenon can be determined, and this can be made aware of by the driver or used for physical condition management of the driver.

Experimental Example 1

(Detection Of The Subjective Sleepiness During Driving By The Subjective Sleepiness/Low Consciousness Traveling State Detecting Means 623 (Second Subjective Sleepiness/Low Consciousness Traveling State Detecting Means 623b))

A biological evaluation (static experiment) until the subjective sleepiness occurs from wakefulness in an actual vehicle idling state and a biological evaluation (dynamic experiment) when the subjective sleepiness occurs during actual vehicle traveling were performed.

The static experiment was for 60 minutes, and measurement indexes were the APW and a subjective evaluation with respect to the subjective sleepiness. The APW was measured continuously during the experiment, and the subjective evaluation was evaluated before the start of experiment and every passage of five minutes after the start of experiment. A visual analog scale was used for the subjective evaluation. Further, subjects were instructed not to sleep during the experiment. The subjects were eight males in their twenties and thirties who are healthy, agreed in advance upon explanation of the experiment and sufficient understanding of the experiment. In the dynamic experiment, an evaluation was performed targeting at 89 examples of data for a measurement time of 30 minutes or more on calculations of distribution rates. An evaluation of the subjective sleepiness was performed by pressing a monitor of a measurement device at a timing it occurs. Note that the measurement device was based on visual field standards for a driver of an automobile or the like, which are defined by the Ministry of Land, Infrastructure, Transport and Tourism and placed within arm's reach. An analysis of the APW was performed by calculating the distribution rates of the above-described three frequency components by frequency-analyzing the frequency gradient time series waveform by the second subjective sleepiness/low consciousness traveling state detecting means 623b. Note that for detection of the peak points of the distribution rates, smoothing differentiation at 12 points was used.

Static Experiment Results

Figure 18A:
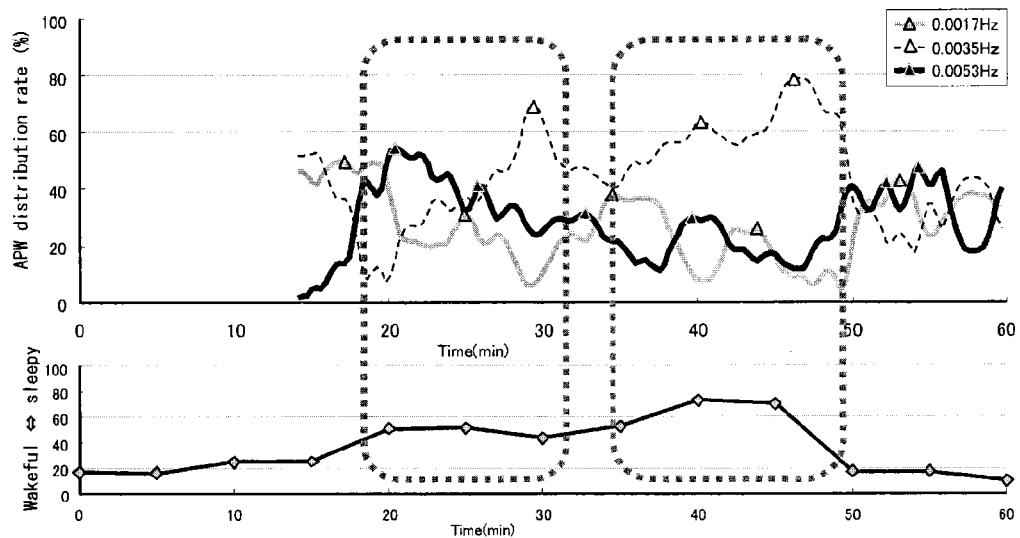
FIG. 18A is a diagram illustrating results of time series waveforms of distribution rates of the APW measured by a static experiment of Experimental Example 1.

FIG. 18A illustrates results of time series waveforms of distribution rates of the APW measured by the static experiment. In seven examples among the eight subjects, the fatigue reception signal (0.0035 Hz) outstood in the vicinity of occurrence of sleepiness, but in none of them, appearance of peak values of the distribution rates of the function adjusting signal (0.0017 Hz), the fatigue reception signal (0.0035 Hz) and the activity adjusting signal (0.0053 Hz) satisfied the following relation: activity adjusting signal≤function adjusting signal≤fatigue reception signal (see FIG. 13 and FIG. 14).

Dynamic Experiment Results

Figure 18B:
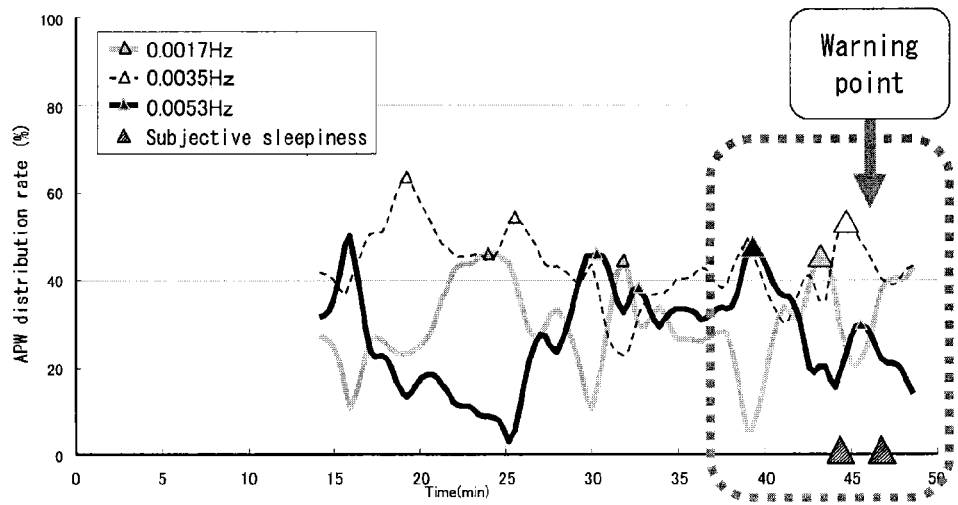
FIG. 18B is a diagram illustrating results of time series waveforms of distribution rates of the APW measured in the dynamic experiment.

FIG. 18B illustrates results of time series waveforms of distribution rates of the APW measured in the dynamic experiment. Immediately before occurrence of subjective sleepiness, appearance of peak values of the distribution rates of the function adjusting signal (0.0017 Hz), the fatigue reception signal (0.0035 Hz) and the activity adjusting signal (0.0053 Hz) satisfies the following relation: activity adjusting signal≤function adjusting signal≤fatigue reception signal (see FIG. 13 and FIG. 14).

Note that results of a chi-squared test when the subjective sleepiness by the APW distribution rate was detected at points where the subjective sleepiness occurred in 89 examples as analysis targets and in the vicinity thereof are as illustrated in FIG. 15(b) as described above, in which a correct answer rate was 77% and $p=2.09 \times 10^{31\ 9}$.

From results of FIGS. 18A, 18B and FIG. 15B, it can be seen that detection of the subjective sleepiness during driving is associated with peak predominance of the distribution rate of very low frequency component of the APW and the order of appearance thereof. However, in the static experiment, it did not become a predetermined order of appearance as in the dynamic experiment, and thus reaction of a living body differs in a static state and a dynamic state. This is conceivably because the situation of driving is in an environment different from a static state, in which it is necessary to strongly resist sleepiness, there are many external stimuli, and it is an environment where concentration is easy, and it can be seen that the method of the present invention is suitable for determination of the biological state during driving.

Further, regarding the frequency gradient time series waveforms in 89 examples of the above-described dynamic experiment, as illustrated in FIG. 19A, the cases where the amplitude value comes within a predetermined set range and the cycle becomes a short cycle in a predetermined set range were further detected by the subjective sleepiness/low consciousness traveling state detecting means 623. Many of them were data for which comments are left, such as "I was absentminded", "my consciousness was gone far away", or the like as comments of the subjects after traveling (data with a possibility of the low consciousness traveling state). Results of the chi-squared test evaluating the detection result of the subjective sleepiness or the low consciousness traveling state by this frequency gradient time series waveform and the detection result of the subjective sleepiness by the above-described distribution rates together are FIG. 19B, where the number of non-detections of the subjective sleepiness and the low consciousness traveling state was 4 (see FIG. 15C). From this, it can be seen that, in addition to grasping the order of appearance of the predetermined frequency components in the distribution rates of the APW, grasping the low amplitude of the frequency gradient time series waveform and its cycle becoming short are effective for detecting the subjective sleepiness and the low consciousness traveling state.

Experimental Example 2

(Detection of the Hypnagogic Symptom Phenomenon by the Hypnagogic Symptom Phenomenon Detecting Means 621 by Using the Frequency Gradient Time Series Waveform)

A verification experiment for the relation between the timing when a diversion tendency in the frequency gradient time series waveform appears and the hypnagogic symptom phenomenon was performed. The experiment was performed for both analysis of a finger plethysmogram sampled by using a finger photoplethysmograph and analysis of the APW in the present invention. Note that a camera for observing the condition of a subject was used together.

The experimental condition was a static state, the experiment time was 60 minutes, and a premise was made that the wakeful state should be maintained until the end of experiment. Subjects were nine males and one female in their twenties and thirties who are healthy and non-disabled.

Figure 20A:
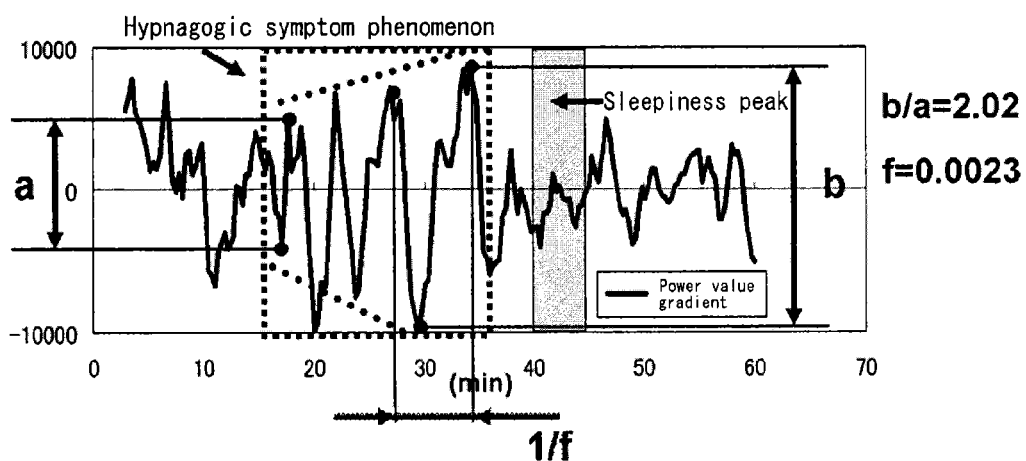
FIGS. 20A, 20B are diagrams for explaining a method of determining a hypnagogic symptom phenomenon from the frequency gradient time series waveform.

FIG. 20A illustrates a power value gradient time series waveform of a fingertip pulse wave of one subject. In the diagram, 40 to 45 minutes indicate the time zone in which the sleepiness is increased most based on a sensory evaluation. Further, it was suggested that a dashed-line part is the hypnagogic symptom from that the amplitude increases (increases from a to b) before the time zone in which the sleepiness increases and the cycle becomes long (f becomes a long cycle).

Figure 20B:
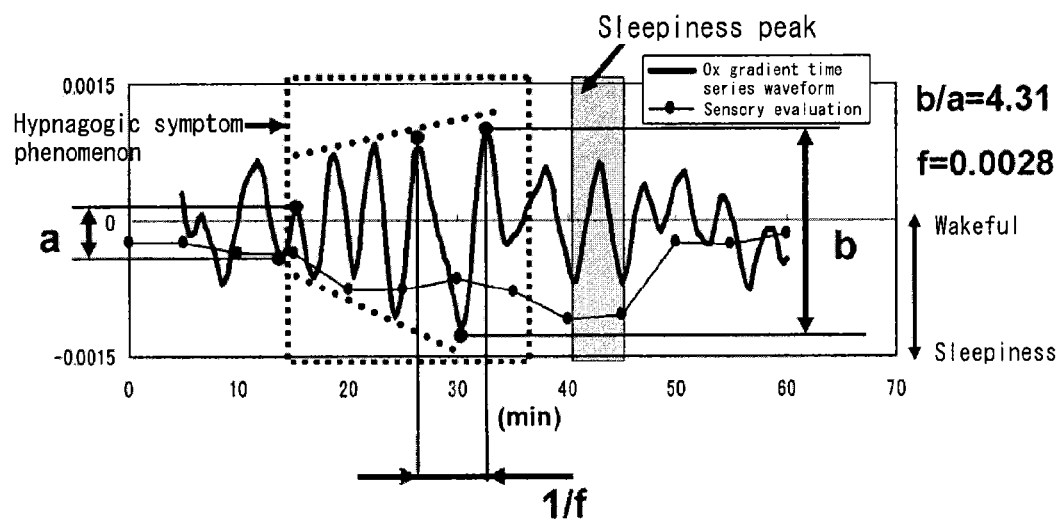

FIG. 20B illustrates a frequency gradient time series waveform of the APW. In the region of a dashed-line part in the diagram, a tendency to diverge appears before sleepiness increases, and temporal timing matches with the dashed line part of FIG. 2, suggesting that it is the hypnagogic symptom. The power value gradient time series waveform of the fingertip pulse wave and the frequency gradient time series waveform of the APW are related with the sympathetic nerve activity, and thus it is conceivable that a rise in the sympathetic nerve activity is occurring while the amplitude of the waveform is diverging. It is conceivable that this rise in the sympathetic nerve activity occurs as resistance to sleepiness.

Figure 21A:
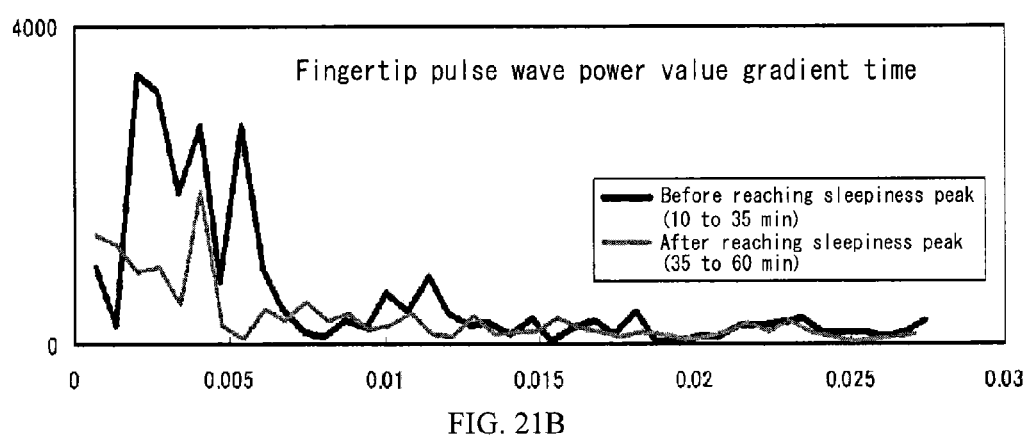
FIGS. 21A, 21B are diagrams illustrating results of performing a frequency analysis for each of 25 minutes before reaching and 25 minutes after reaching a sleepiness peak in FIGS. 20A, 20B.
Figure 21B:
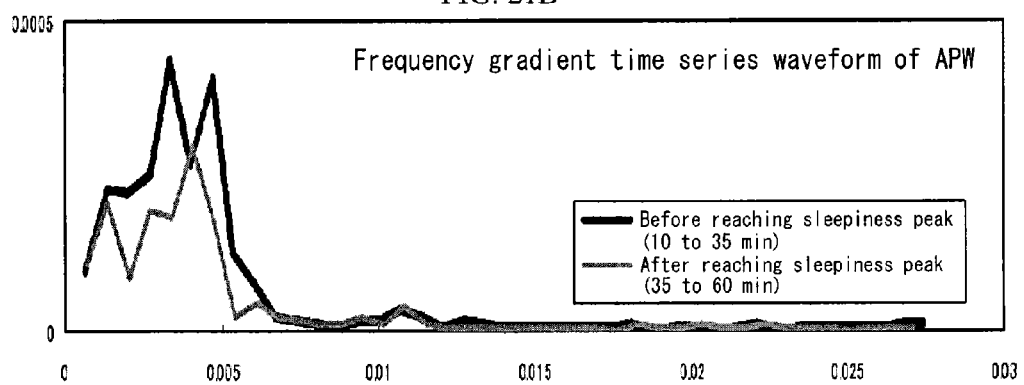

FIGS. 21A, 21B illustrate results of performing a frequency analysis for each of 25 minutes before reaching and 25 minutes after reaching a sleepiness peak in FIGS. 20A, 20B. FIG. 21A is a frequency analysis result of a fingertip pulse wave power value gradient time series waveform, and illustrates a comparison before and after sleepiness reaches its peak. After the sleepiness reaches its peak, a decreasing tendency of the spectrum was obtained. FIG. 21B is a frequency analysis result of the frequency gradient time series waveform of the APW, and illustrates a comparison before and after sleepiness reaches its peak. Similarly to the finger plethysmogram, a decreasing tendency of the amplitude of the spectrum was obtained. Further, a peak occurs in the vicinity of 0.0033 Hz in the frequency analysis before the sleepiness peak including a diversion waveform, it is conceivable that the divergence waveform includes the component in the vicinity of 0.0033 Hz, suggesting a relation with the hypnagogic symptom.

Figures 22, 23:
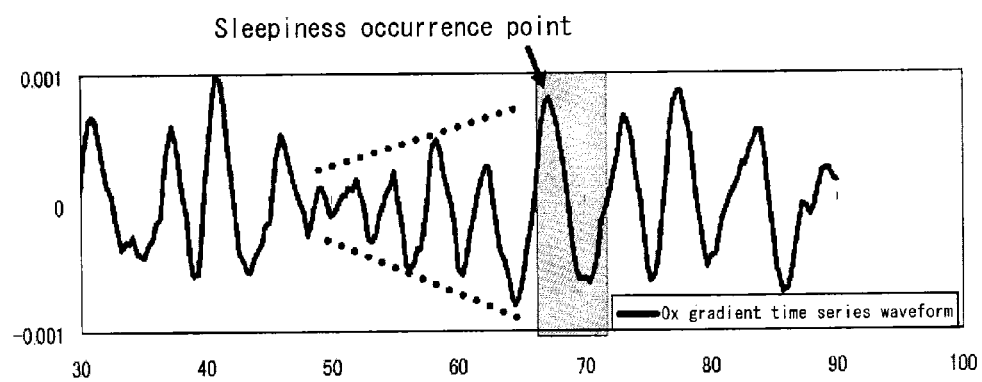
FIG. 22 is a diagram illustrating a 2×2 cross table regarding wakefulness and hypnagogic symptom in finger plethysmograms and APW of ten subjects of Experimental Example 2.
FIG. 23 illustrates an example of data indicating a correlation of the frequency gradient time series waveform of the APW sampled during actual vehicle traveling and the presence of sleepiness.

FIG. 22 illustrates a 2×2 cross table regarding the finger plethysmograms of ten subjects, and wakefulness and hypnagogic symptom in the APW.

As a result of the chi-squared test, it is statistically significant because the P value is 0.05 or less, suggesting a possibility that there is a relation between the finger plethysmogram and the APW. From them, it is conceivable that the divergence tendency in the frequency gradient time series waveform of the APW indicates the hypnagogic symptom phenomenon. FIG. 23 is an example of data indicating a correlation of the frequency gradient time series waveform of the APW sampled during actual vehicle traveling and the presence of sleepiness. A divergence tendency in FIG. 23 indicates a similar tendency to the records of performing in the static state, and thus it can be seen that the hypnagogic symptom phenomenon can be identified by detecting a divergence phenomenon of the frequency gradient time series waveform of the APW during actual vehicle traveling.

Experimental Example 3

(Detection of the Imminent Sleep Phenomenon by the Imminent Sleep Phenomenon Detecting Means 622 by Using the Frequency Gradient Time Series Waveform)

A verification experiment for the relation of timing when a diversion tendency in the frequency gradient time series waveform appears and the imminent sleep phenomenon was performed.

As the experiment, a sleep experiment was performed in two postures, a sitting posture and a lying posture, from a state of resisting sleep until accepting sleep and entering sleep equivalent to a nap. Subjects are 56 males in their twenties to fifties (31.8±8.2 years old) who are healthy and non-disabled. As comparison indexes, there were used brain waves, electrocardiograms, and finger plethysmograms, and they were compared with the APW which is a measurement index in the present invention. For 30 minutes after the start of experiment, the subjects were obliged to maintain the wakeful state, and thereafter, this obligation was released and it was left on the free will of them.

FIGS. 24A-24D illustrate results of the sleep experiment of a 24-year-old male subject. The subject remarked, "I was kept my wakeful state for 10 minutes in the beginning, but after that I barely kept the wakeful state while resisting sleepiness. After 30 minutes when I was released from the obligation of maintaining the wakeful state, I quitted resisting sleepiness and soon shifted to sleep in an early stage."

Figure 24A:
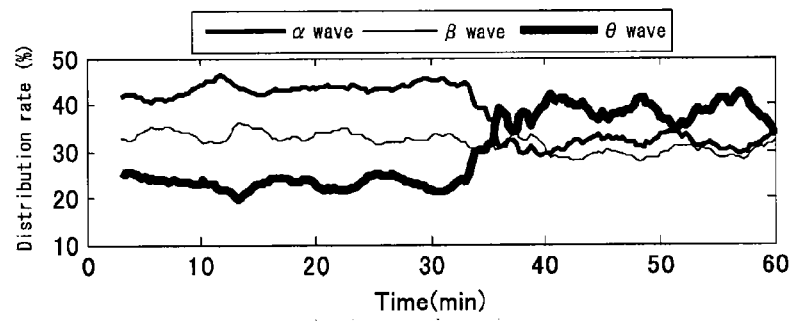
Figure 24B:
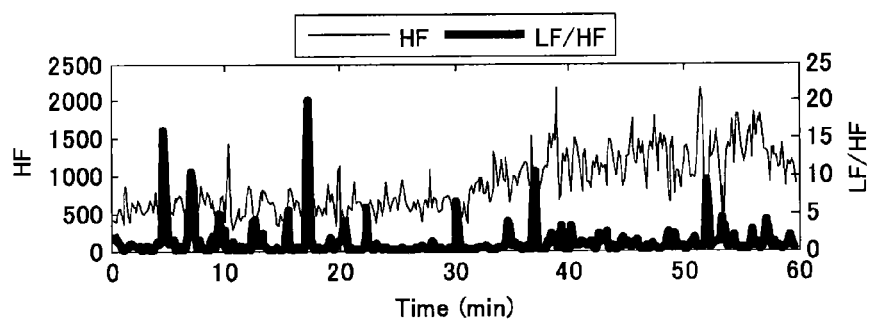
Figure 24C:
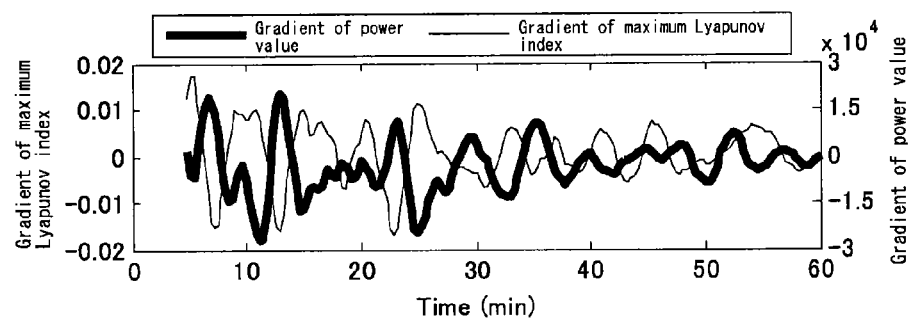
Figure 24D:
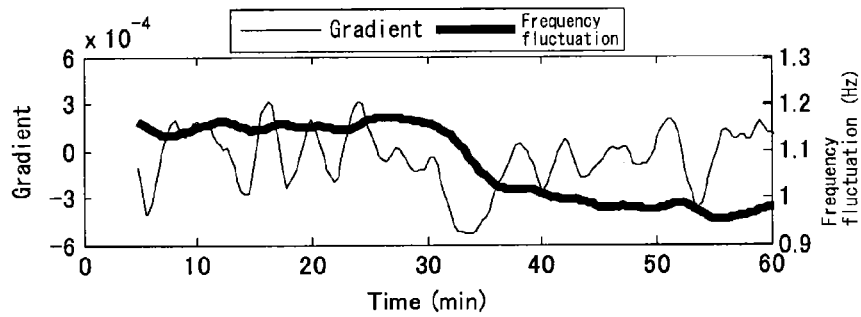

FIG. 24A illustrates distribution rates of $\theta$ wave, $\alpha$ wave, $\beta$ wave of brain waves. The 40-minute point when the $\theta$ wave increases, the $\beta$ wave decreases, and both the waves begin to stably change was taken as a fallen asleep point. FIG. 24B illustrates activity levels of the sympathetic nervous system (LF/HF) and the parasympathetic nervous system (HF) obtained by wavelet-analyzing the finger plethysmogram. The HF stably maintains a high state after 40 minutes, the LF/HF stably indicates a low numeric value, and it is conceivable that the fallen asleep point is around 40 minutes after the start of experiment. FIG. 24C illustrates a gradient time series waveform of power value and a gradient time series waveform of a maximum Lyapunov index which are obtained by performing a gradient time series analysis on the finger plethysmogram. Until 30 minutes, a hypnagogic symptom phenomenon with low frequency and large amplitude is shown, and after 30 minutes, it tends to converge with low amplitude to be a long cycle. Here, it is also conceivable that the subject shifted to the sleep state around 40 minutes. FIG. 24D illustrates the frequency gradient time series waveform and the frequency fluctuation time series waveform by the zero cross detection method of the APW. From the frequency fluctuation time series waveform, it can be seen that the frequency of the APW largely changes largely from 1.15 Hz to 1 Hz in 10 minutes from 30 minutes to 40 minutes. Therefore, it is conceivable that the subject was in the wakeful state for 30 minutes from the start of experiment, and then shifted to the sleep state at 30 minutes to 35 minutes after the start of experiment. In the frequency gradient time series waveform, after 30 minutes, similarly to the gradient time series waveform of the power value of the finger plethysmogram, it tends to converge with low amplitude and a long cycle. Therefore, it can be seen that the imminent sleep phenomenon immediately before the fallen asleep point can be detected by detecting the timing of the convergence tendency of the frequency gradient time series waveform.

The above result matches the subject's remark.

Figure 25A:
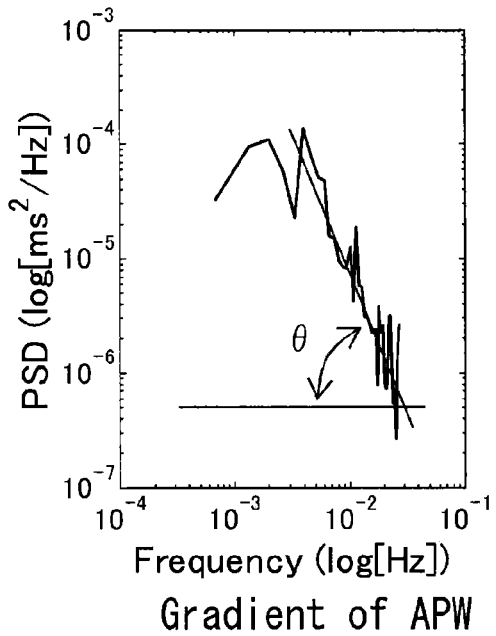
FIGS. 25A, 25B are diagrams illustrating frequency analysis results of a sleep resisting state in Experimental Example 3.
Figure 25B:
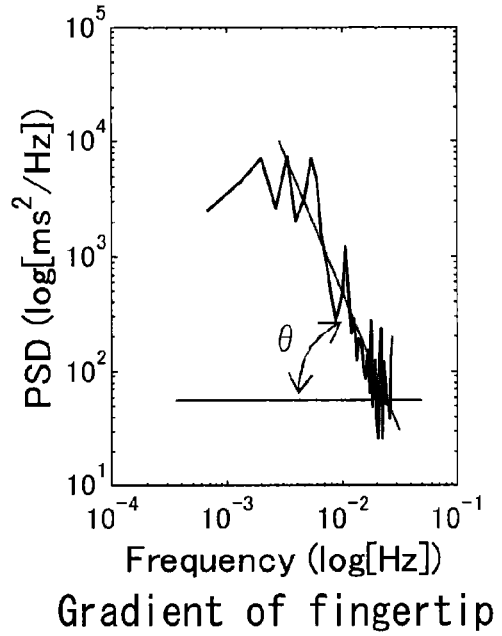
Figure 26A:
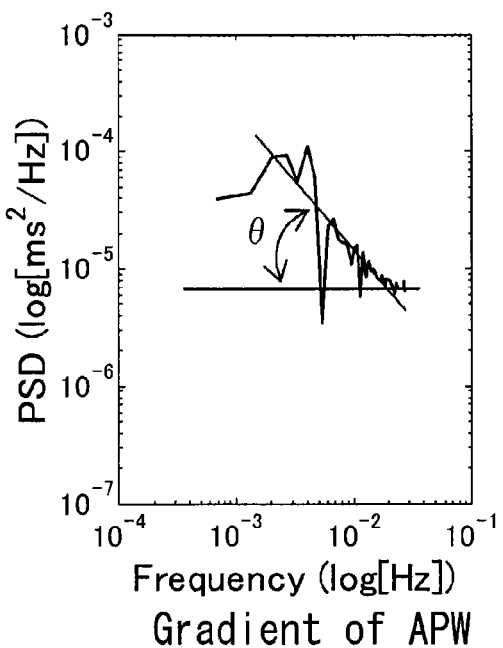
FIGS. 26A, 26B are diagrams illustrating frequency analysis results of a sleep state.
Figure 26B:
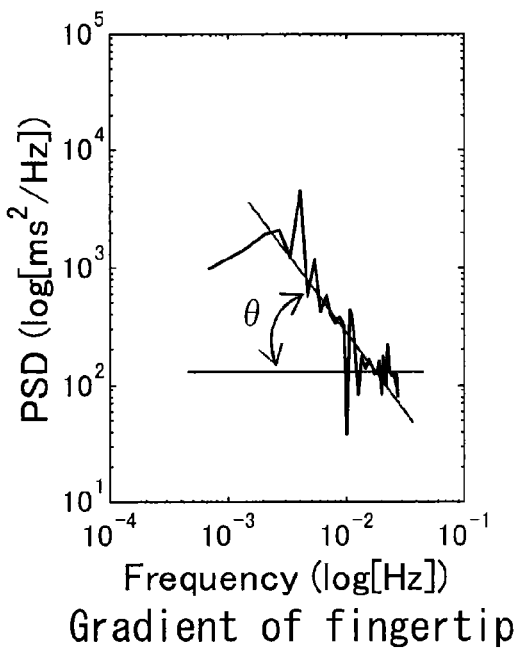

Here, the difference in state of the both was verified assuming the 30 minutes from the start of experiment as a state of resisting sleepiness and maintaining to be wakeful (sleep resisting state), and 30 minutes of the latter half as a state of accepting sleepiness and entering sleep (sleep state). FIGS. 25A, 25B illustrate frequency analysis results of the sleep resisting state, and FIGS. 26A, 26B illustrate frequency analysis results of the sleep state. The frequency analysis results of the respective gradient time series waveforms of the finger plethysmogram and the APW indicate the same tendency in both the sleepiness resisting state and the sleep state. The gradient of the spectrum of the sleep state is close to 1/f, and can be considered as a relaxed state of parasympathetic nerve predominance. On the other hand, the gradient of the spectrum of the sleep resisting state is close to 1/f2, indicating an angle different from the gradient of the spectrum of the sleep state. It is conceivable that this is because of the rise in the sympathetic nerve activity due to resisting sleepiness.

Next, states of the 56 subjects were determined by using the gradients of spectra of the respective gradient time series waveforms of the finger plethysmogram and the APW. For determination of the states by the gradients of spectra of the finger plethysmogram and the APW, angles θ of gradients of spectra illustrated in FIGS. 25A, 25B and FIGS. 26A, 26B were used. As the gradients of spectra, by adding a tendency in cases of mechanical processing, 54 degrees resulted from correcting +9 degrees to 45 degrees as a gradient angle of 1/f was set as a reference value. Specifically, less than 54 degrees is assumed as the sleep state, and equal to or more than 54 degrees is assumed as the sleep resisting state. Whether a determination result is a pass or not was determined by comparing with the brain waves, the activity level of the autonomic nervous system, and the subject's comment.

State determination results by using the gradients of spectra of the APW both indicated high correct answer rates, the sleep resisting state being 82% and the sleep state being 79%. State determination results by using the gradients of spectra of the finger plethysmogram are the sleep resisting state being 74% and the sleep state being 62%, which are somewhat low correct answer rates as compared to the determination results by the APW. The finger plethysmogram grasping the dynamic state of the peripheral circulation system is easily affected by external stimuli, but since the APW grasps the dynamic state of the central system, it is not easily affected by external stimuli. That is, the APW can stably grasp fluctuation of the heart-circulatory system, and it is conceivable that the correct answer rate is high as compared to the finger plethysmogram.

From these facts, it can be seen that whether or not the amplitude and cycle of the frequency gradient time series waveform of the APW indicates a tendency to diverge with respect to a predetermined reference value and thereafter converge indicates the sleep resisting state (the hypnagogic symptom phenomenon and the imminent sleep phenomenon) before reaching the sleep state. Therefore, it can be said that it is effective to detect the hypnagogic symptom phenomenon from the diversion tendency as described in Experimental Example 2 and to detect the imminent sleep phenomenon from the conversion tendency as in this Experimental Example 3 by using the frequency gradient time series waveform of the APW.

Experimental Example 4

(Demonstration Experiment During Long Distance Traveling)

Figure 27B:
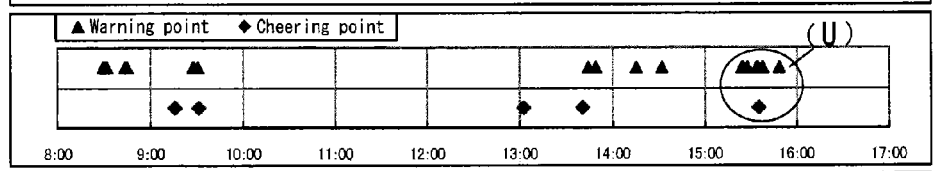
Figure 27C:
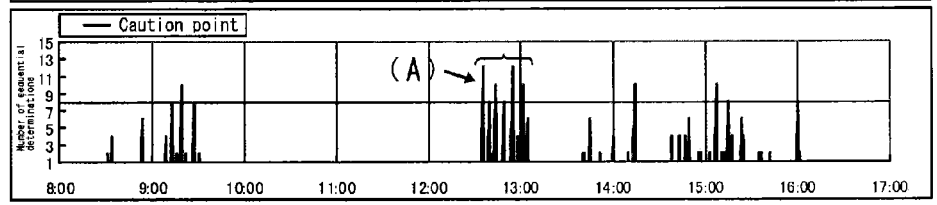
Figure 27D:
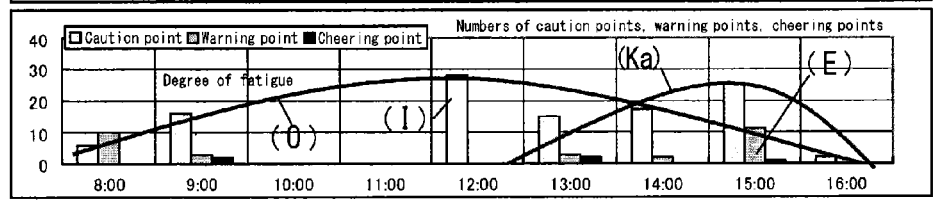
Figure 28A:
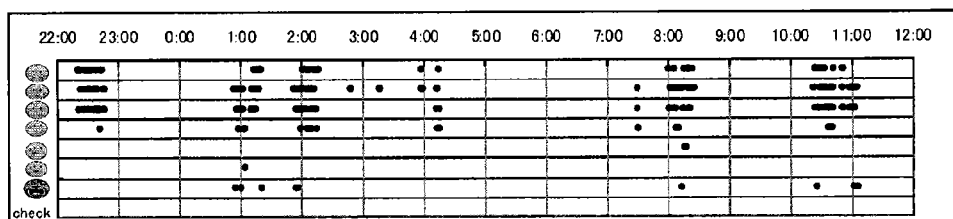
FIGS. 28A to 28D are diagrams illustrating results of a male subject in his forties in a demonstration experiment during long distance traveling of Experimental Example 4.
Figure 28B:
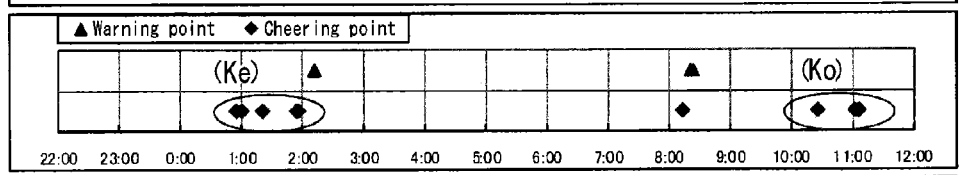
Figure 28C:
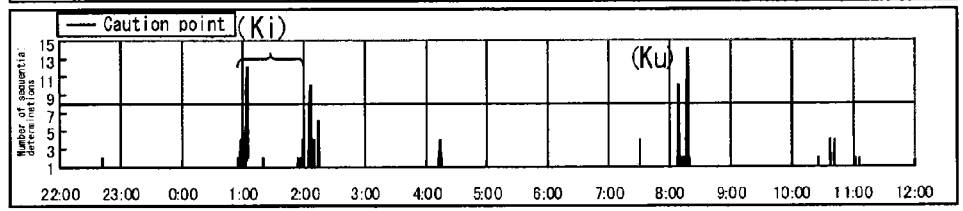
Figure 28D:
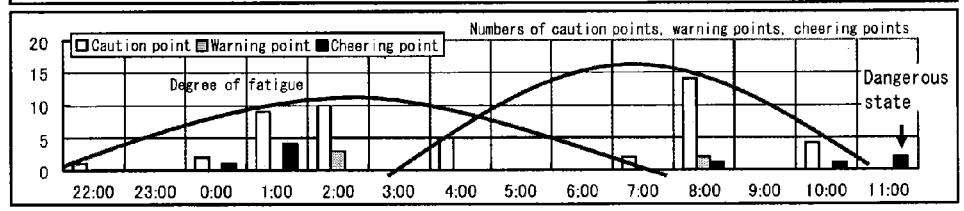

The biosignal measuring device 1 of the embodiment was attached to a seat back of a track, and a demonstration experiment during long distance traveling by a truck driver was performed. After operation, a questionnaire on his own physical condition at the time of operation was carried out. Subjects were professional drivers (9 males) in their twenties to fifties employed in transportation industries, and the total operation number of all the subjects was 91 times. FIGS. 27A to 27D illustrate a determination result of the male subject in his thirties, and FIGS. 28A to 28D illustrate a determination result of a male subject B in his forties. FIGS. 27A, 28A each illustrate the homeostasis function level as a determination result of the homeostasis function level determining means 624, and FIGS. 27B, 28D to 27D, 28D illustrate determination results of the biological state determining means using history 627. FIGS. 27B, 28B illustrate a history point B (cheering point) where the hypnagogic symptom phenomenon or the imminent sleep phenomenon is detected by the hypnagogic symptom phenomenon detecting means 622 and the imminent sleep phenomenon detecting means 623 and a history of a history point C (warning point) where the subjective sleepiness or the low consciousness traveling state is detected by the subjective sleepiness/low consciousness traveling state detecting means 623. FIGS. 27C, 28C illustrate the number of cases that the homeostasis function level is sequentially determined by the homeostasis function level determining means 624 as a state requiring a caution as a history point A (caution point) depending on the time. FIGS. 27D, 28D illustrate the numbers of caution points, warning points and cheering points taken on the vertical axis by bar graphs over time, and a change tendency with a curve.

In the case of the male subject A illustrated in FIGS. 27A to 27D, he departed an office at 8:00, performed desk work in another office and outdoor work from 10:00 to 12:00, and started operation again from 12:20. A lunch break was taken in middle for 30 minutes from 13:00. There were an increase in tiredness by sequential caution points from 12:30 to 13:00 indicated by (A) and (I) in the operation result graphs, sequential warning points from 15:00 to 16:00 illustrated by (U), (E) in the diagram, and appearance of a cheering point. This matched the contents of a hearing from the male subject A after operation. Further, curves (O) and (Ka) in FIGS. 27A to 27D indicate a degree of fatigue, and the male subject A is possibly in a dangerous state around 15:00 when his work finishes.

In the case of the male subject B illustrated in FIG. 28, a time zone in which an increase in tiredness is captured at (Ki) and (Ku) in the diagram, and a time zone in which a dangerous state due to fatigue appears is captured at (Ke) and (Ko) in the diagram. By thus indexing the appearance of sleepiness and the degree of progress of fatigue, a time zone to be in a dangerous state could be estimated from the degree of fatigue.

Therefore, by analyzing such a determination result by a computer of a manager, the degree of fatigue of each driver and the timing when shifting to a dangerous state can be grasped, which is suitable for operation management.

Note that when various calculation results of the analyzing and calculating means 61 and various determination results of the determining and detecting means 62 are further analyzed by a computer on the manager side for performing operation management, for example, management can be performed by allowing displaying data as illustrated in FIGS. 27A to 27D and FIGS. 28A to 28D by driver. In this case, as illustrated in FIG. 29, by displaying a more detailed physical condition map together, the states of drivers can be managed in more detail.

FIG. 29 is obtained from the time series waveform of the APW of a male subject C in his thirties, and represents the states of physical conditions during operation as a physical condition map and a sensation response map by a quantization method proposed by the present applicant as Japanese Patent Application No. 2011-108909, and the like. In this diagram, the sampled APW is frequency-analyzed, an analysis waveform is represented by displaying on log-log axes, the analysis waveform is separated into low frequency band, medium frequency band, and high frequency band regarding a target analysis section, scoring of the analysis waveforms is performed based on a constant reference from gradients of separated analysis waveforms and the shape of the whole analysis waveform, and it is plotted on coordinate axes. The physical condition map is seeing the condition of control of the autonomic nervous system as a balance between the sympathetic nervous system and the parasympathetic nervous system, and the sensation response map is such that the condition of change of a heartbeat fluctuation is superposed on the physical condition map. Amounts of 13 operations are summarized by week and physical condition (based on answers of the questionnaire). The lower part illustrates questionnaire results related to physical conditions after operation, and this subject felt that his physical condition tended to worsen in the first half of the implementation period and then tended to recover in the second half.

In the graphs by week, the physical condition map changes from a distribution (Sa) rising to the right centering on vigor (concentration/uplifted/irritated) and exhausted (feel heavy, depressed) on the first week, to a distribution (Shi) of falling to the right centering on calm (relaxed) on the third week. Categorizing this by physical condition, the group of answers "good" and "ordinary" falls to the right and its distribution spreads toward the calm, relaxed (Su, Se). This suggests that both the mind and body tend to be relaxed, being able to perform the driving easily. On the other hand, the group of answers "bad" and "very bad" rises to the right on the physical condition map, centering on vigor and exhausted but having a small distribution of calm (So), the sensation map has a large distribution of uplifted and a spread in a relaxed direction is small as compared to the group of "good" and "ordinary", in which its rapid drop from exited to calm can be seen (Ta). Note that the other drivers resulted similarly.

By performing the operation management in this manner, a contribution to appropriate operation management can be made. Of course, this is merely an example, and the contents of operation management are not limited thereto. For example, the conditions of the wakeful state and the sleep state of Experimental Example 5, which will be described later, can be managed together, or moreover, not limited to by person, it can be separated by road, by period, by season, or the like, so as to perform analysis from various aspects.

Experimental Example 5

(Detection of the Wakeful State and the Sleep State by Using the Frequency Fluctuation Time Series Waveform)

The degree of separation of the frequency fluctuation time series waveform by the peak detection method and the frequency fluctuation time series waveform by the zero cross detection method obtained by the frequency fluctuation calculating means 613 was compared, and a verification experiment on whether the wakeful state and the sleep state can be determined or not was performed.

To measure biosignals of the wakeful state and the sleep state, a sleep introduction experiment was performed in a supine position. Subjects are 11 males in their twenties and thirties who are healthy and non-disabled. At the same time as the APW, there were measured a finger plethysmogram, brain waves, and a mentalis muscle electromyogram. The biosignal measuring device 1 for measuring the APW was disposed between the back of the subject and the bed. The measurement time was 60 minutes, the subject was instructed not to sleep during 30 minutes from the start of measurement, and the degree of sleepiness was evaluated in every passage of five minutes. Sleep after 30 minutes pass was on the free will of the subjects.

Figure 30A:
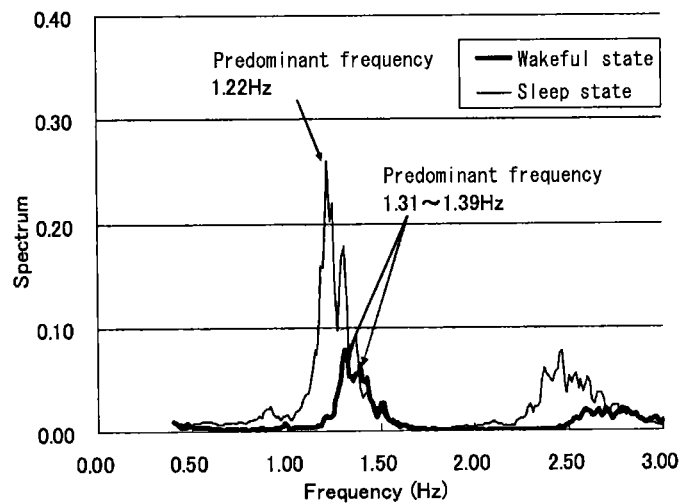
FIGS. 30A to 30C are diagrams illustrating analysis results of Experimental Example 5.

The determination of the awaken state and the sleep state were performed from observation, the brain waves, and the mentalis muscle electromyogram of the subject. FIG. 30A illustrates frequency spectra of the finger plethysmogram for six minutes each in the wakeful state and the sleep state. In the sleep state, it can be seen that the predominant frequency is low as compared to the wakeful state. Similar results were obtained from 11 subjects among the 11 subjects.

Figure 30B:
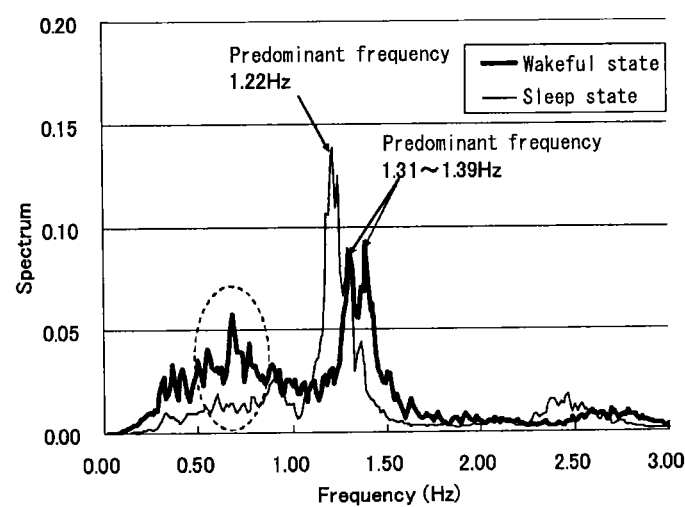

FIG. 30B illustrates the frequency spectra of the APW for six minutes each in the wakeful state and the sleep state. In the sleep state, it can be seen that the predominant frequency is low as compared to the wakeful state. Similar results were obtained from 11 subjects among the 11 subjects. From the above, it can be seen that the predominant frequencies of respective frequency spectra of the finger plethysmogram and the APW match.

Figure 30C:
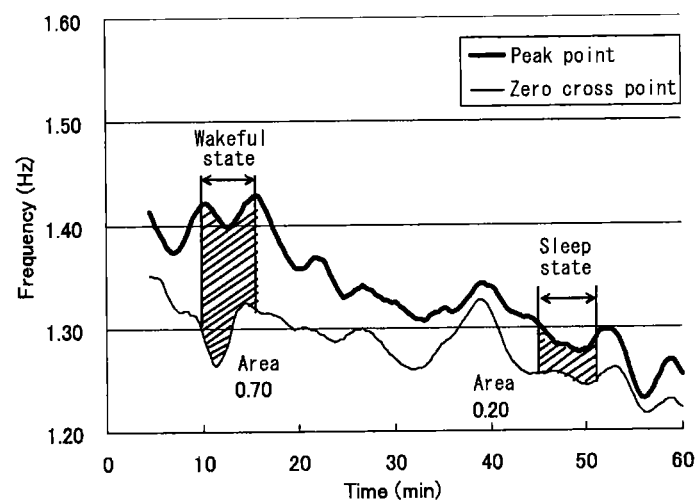

FIG. 30C illustrates the frequency fluctuation time series waveforms of peak point and zero cross point of the APW. In six minutes each of the wakeful state and the sleep state, a difference in areas of waveforms between the peak point and the zero cross point was calculated and was evaluated as the degree of separation of waveforms. In the sleep state, it can be seen that the degree of separation is low as compared to the wakeful state. Similar results were obtained from 11 subjects among the 11 subjects.

The predominant frequencies of frequency spectra of the finger plethysmogram and the APW match, and thus similarly to the finger plethysmogram, it is suggested that the heartbeat fluctuation can be grasped also by the APW. Further, the predominant frequencies of frequency spectra of the both and frequency fluctuation of the APW are lower in the sleepiness state than in the wakeful state, and this matches that the heart rate decreases in the sleep state, suggesting that measurements of the finger plethysmogram and the APW of this experiment were performed correctly.

It was found that the degree of separation of the frequency fluctuation time series waveforms of the peak point and the zero cross point decreases in the sleep state as compared to the wakeful state. If a frequency fluctuation of the zero cross point grasps the sympathetic nerve activity, it is conceivable that the frequency was affected by a decrease in the sympathetic nerve activity in the sleep state and decreased. If a frequency fluctuation of the peak point grasps the sympathetic nerve activity and the parasympathetic nerve activity, it is conceivable that it was affected by a decrease in the sympathetic nerve activity and a rise in the parasympathetic nerve activity in the sleep state, and the frequency decreased largely than the zero cross point. As a result, it is conceivable that the degree of separation of the frequency fluctuation time series waveforms of the peak point and the zero cross point decreased.

From this fact, the wakeful and sleep states can be presumed by evaluating the degree of separation of the frequency fluctuation time series waveforms of the peak point and the zero cross point of the APW, that is, setting whether it is separated more than a predetermined reference value or not. Therefore, by using this, by obtaining plural data of the degree of separation of the wakeful state and the sleep state in advance and setting thresholds from them, whether it is the wakeful state or the sleep state or not can be determined automatically as described above. Although normally the driver would not fall asleep during driving, this can help to detect emergency cases, and can be used by the manager for grasping and analyzing when and what degree the driver took a nap after operation.

Note that when the frequency spectra of the finger plethysmogram and the APW are compared, there was a peak of spectrum in the vicinity of 0.6 Hz in the frequency spectrum of the APW, indicating a high spectrum in the wakeful state than in the sleep state. Thus, the APW contains information which is not present in the finger plethysmogram, and it is suggested that it is more effective for estimation of the wakeful state and the sleep state than the finger plethysmogram. From the above, it is conceivable that there is a relation between the degree of separation of the peak point and the zero cross point of the APW and the spectrum in the vicinity of 0.6 Hz. FIG. 31 is a result of checking whether the degree of separation of the peak point and the zero cross point of the APW illustrated in FIG. 30C and increase and decrease tendencies of the spectrum in the vicinity of 0.6 Hz of the APW illustrated in FIG. 30B become the same or not. A result of the chi-squared test is p=0.041(p<0.05) which suggests that the degree of separation of the peak point and the zero cross point of the APW and the spectrum in the vicinity of 0.6 Hz are related, and it can be seen that using data of the APW is effective.

Experimental Example 6

(Consideration on a Rise in the Sympathetic Nerve Activity Which Occurs When Coming to the Processes of the Wakeful Sleepiness (Low Consciousness Traveling State), the Hypnagogic Symptom Phenomenon, the Imminent Sleep Phenomenon)

FIGS. 32A to 32H are diagrams illustrating a result of a sleep experiment of a male subject in his twenties who is healthy and non-disabled. A method of experiment for the sleep test is similar to that of Experimental Example 5.

Sleep stages obtained from data of an electroencephalograph are illustrated in FIG. 32A, and the distribution rates of α wave, β wave, θ wave obtained from the data of the electroencephalograph are illustrated in FIG. 32B. From these results, this subject goes back and forth between wakefulness and sleep stage 1 until about 15 minutes after the start of examination and from 25 minutes to 40 minutes. In self-declaration, he declared sleepiness around 5 minutes, and declared that sleepiness subsided little at 20 minutes by having a conversation. Then, he fell asleep from about 40 minutes.

When comparing this with the gradient time series waveform of the power value of the finger plethysmogram of FIG. 32C, a waveform with large amplitude is seen until about 35 minutes and the hypnagogic symptom phenomenon occurred, and from about 40 minutes, the amplitude became small and the imminent sleep phenomenon occurred.

In an analysis result of the heartbeat fluctuation of FIG. 32D, there is a peak of LF/HF at 374 seconds and 1490 seconds, and it can be seen that there is a rise in the sympathetic nerve activity. Thereafter, there is a peak of HF at 437 seconds and 824 seconds, and it can be seen that the parasympathetic nerve activity is activated. Therefore, also in this graph, it can be seen that the hypnagogic symptom phenomenon and the imminent sleep phenomenon appear in the above time zone.

FIGS. 32E to 32H are analysis results of the APW, and in any of them it can be determined that the subject undergoes the hypnagogic symptom phenomenon and the imminent sleep phenomenon and falls asleep at about 40 minutes. For example, referring to the time series waveform of a zero cross gradient of 32E, a divergence tendency of the waveform can be seen around 5 to 20 minutes and around 25 to 32 minutes and this indicates the hypnagogic symptom phenomenon, and around 35 to 40 minutes, the amplitude of waveform decreases and converges, and the cycle becomes a long cycle thereafter, where it can be seen that the imminent sleep phenomenon occurs. Therefore, the subject fell asleep after 40 minutes.

The trend in the sleep experiment of this subject is as described above, and in the time zone where the subject goes back and forth between wakefulness and sleep stage 1, he feels the subjective sleepiness as can be seen from the self-declaration. Or, his eyes are open but his consciousness level has decreased, being in a state similar to the low consciousness traveling state although not performing driving. Accordingly, in this time zone, a detailed analysis was performed on a predetermined time zone from 374 seconds where the sympathetic nerve activity is rising.

Figures 33A, 33B, 33C, 33D, 33E:
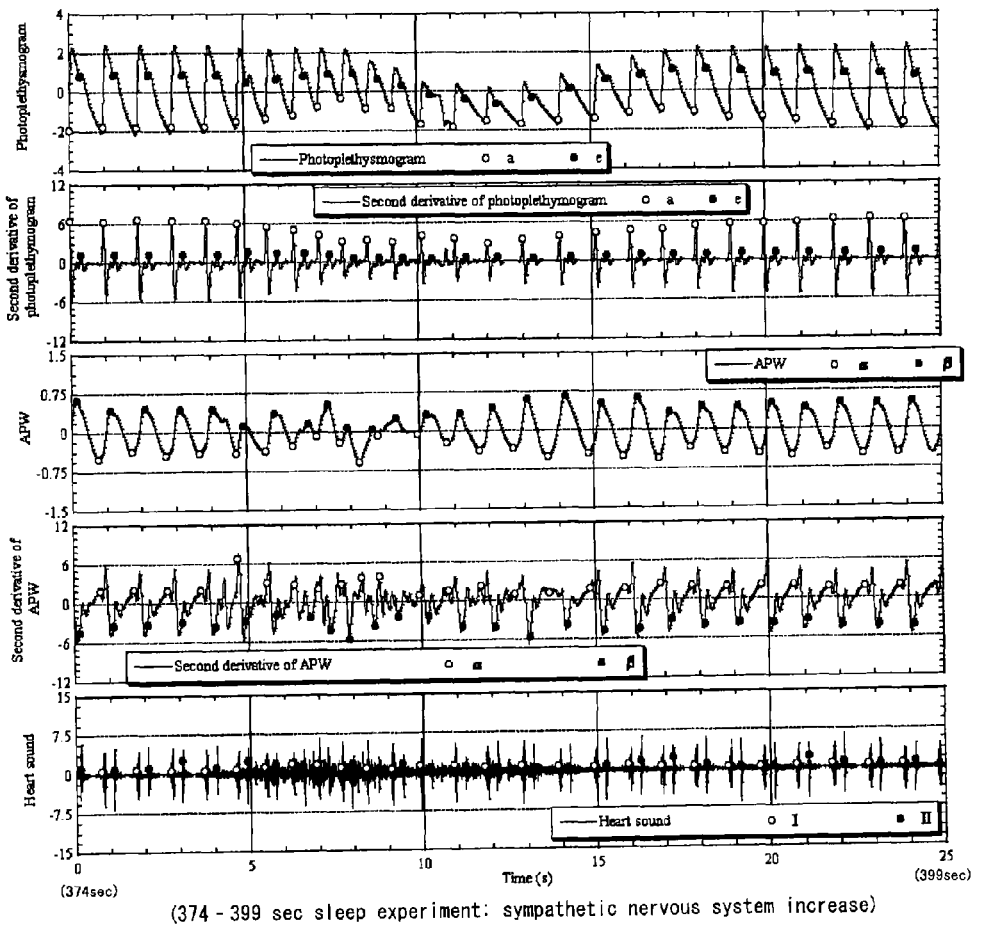
FIGS. 33A to 33E are diagrams illustrating waveforms of various biosignals for 25 seconds from 374 seconds in a sleep state of Experimental Example 6.

FIGS. 33A to 33E illustrate waveforms of the biosignals for 25 seconds from 374 seconds, FIG. 33A is raw waveform of the finger plethysmogram, FIG. 33B is a second order differential waveform of the finger plethysmogram, FIG. 33C is a raw waveform of the APW, FIG. 33D is a second order differential waveform of the APW, and FIG. 33E is a raw waveform of the heart sound. In all the waveforms of the APW, a disturbance can be seen in the waveform before and after 10 seconds from 378 seconds. This is similar to the raw waveform of the heart sound. It can be presumed that, in this period, the subjective sleepiness (equivalent to the low consciousness traveling state) was felt, and the rise in the sympathetic nerve activity occurred. However, in the waveform of the finger plethysmogram, a disturbance occurred several seconds after that.

Figure 34A:
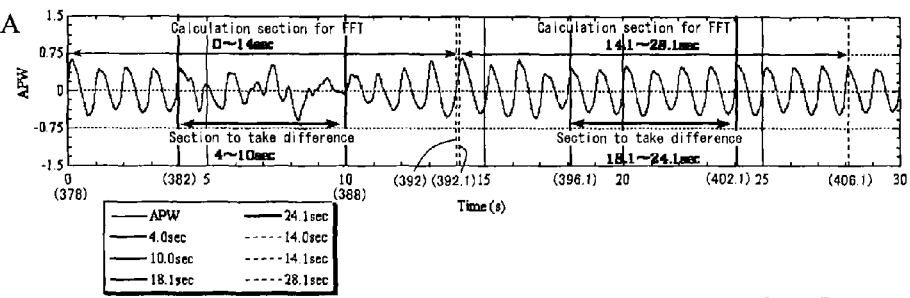
FIGS. 34A to 34E are diagrams illustrating analysis results of the APW in a sleep experiment of Experimental Example 6.

Accordingly, the APW was studied in further detail. FIG. 34A illustrates a raw waveform for 30 seconds from 378 seconds of the APW. Among them, frequency analyses were performed and compared regarding 14 seconds (displayed as "0-14 sec" in the diagram) of 378 to 392 seconds including 6 seconds (displayed as "4-10 sec" in the diagram) of 382 to 388 seconds in which there is a large disturbance of waveform, as well as 14 seconds ("14.1-28.1 sec" in the diagram) from 396.1 to 406.1 seconds including 6 seconds (displayed as "18.1-24.1 sec" in the diagram) of 396.1 to 402.1 seconds in which both the amplitude and the cycle are stable.

Figure 34B:
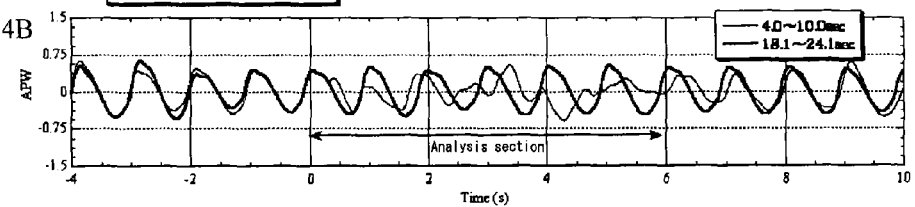
Figure 34C:
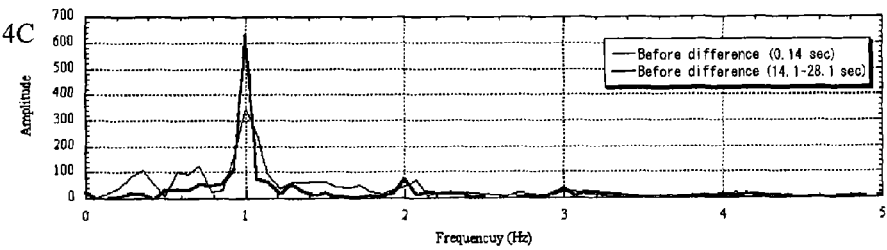

FIG. 34B is a diagram illustrating raw waveforms of two calculation sections for frequency analysis of respective 14 seconds of "0-14 sec" and "14.1-28.1 sec" by overlapping, among which it can be seen that there is a large displacement in phase (difference between the both (time phase difference)) between six seconds of "4-10sec" and six seconds of "18.1-24.1 sec". Therefore, such a displacement in phase indicates the rise in the sympathetic nerve activity. FIG. 34C is a diagram illustrating only real numbers taken by performing Fourier transform in the two calculation sections for frequency analysis of 14 seconds, and it can be seen that there is a difference in the vicinity of 0.4 to 0.6 Hz and the vicinity of 1.2 to 2 Hz excluding the vicinity of 1 Hz. That is, when the rise in the sympathetic nerve activity occurs, the peak becomes relatively small in the vicinity of 1 Hz, but the peak conversely becomes relatively large in the vicinity of 0.4 to 0.6 Hz and in the vicinity of 1.2 to 2 Hz.

Figure 34D:
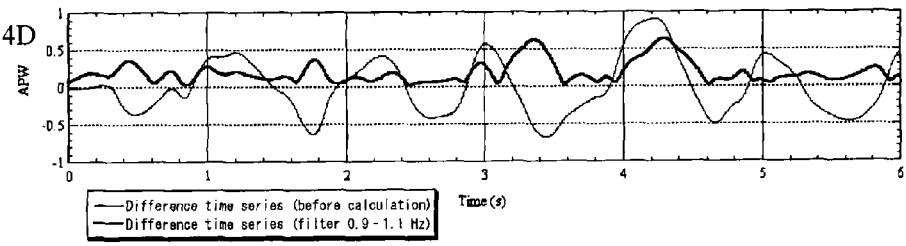
Figure 34E:
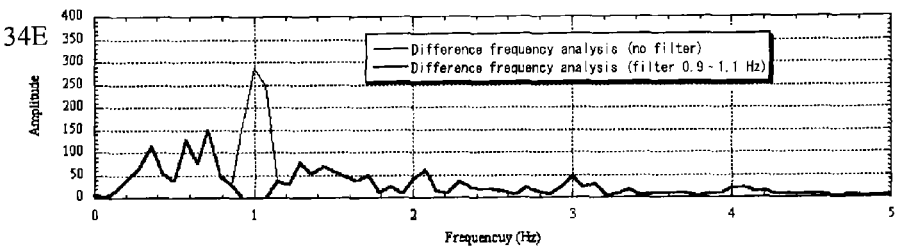

Further, one from a frequency analysis of the waveform of "4-10 sec" and one from a frequency analysis by filtering 0.9 to 1.1 Hz in the vicinity of 1 Hz corresponding to the frequency of the finger plethysmogram were compared. FIG. 34D is a comparison result thereof in time series, and FIG. 34E is a frequency analysis result thereof. It can be seen that, from (d) there is a rising waveform in the vicinities of 3.4 seconds and 4.2 seconds after filtering, in (e) there is a peak in the vicinity of 0.4 to 0.6 Hz and the vicinity of 1.2 to 2 Hz, the rise in the sympathetic nerve activity can be detected by grasping a peak of a frequency component in the APW, and from the timing thereof the subjective sleepiness (equivalent to the low consciousness traveling state) can be detected.

Figure 35A:
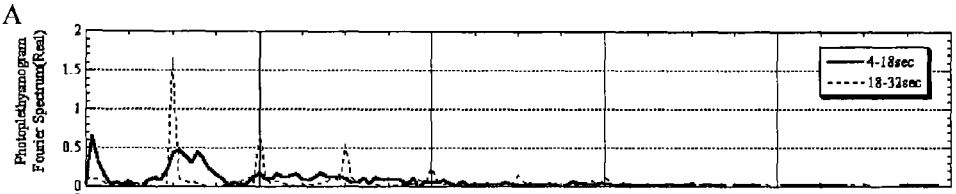
FIGS. 35A to 35E are diagrams illustrating frequency analysis results of various biosignals in the sleep experiment of Experimental Example 6.
Figure 35B:
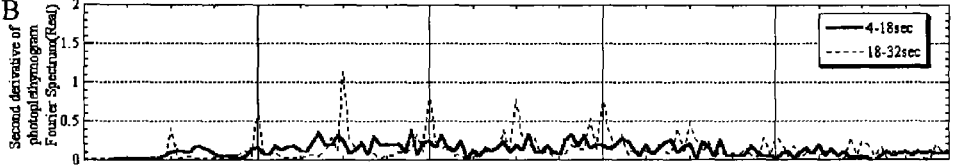
Figure 35C:
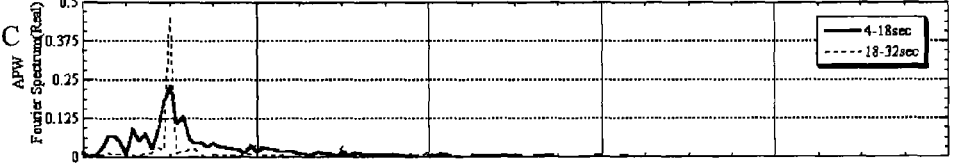
Figure 35D:
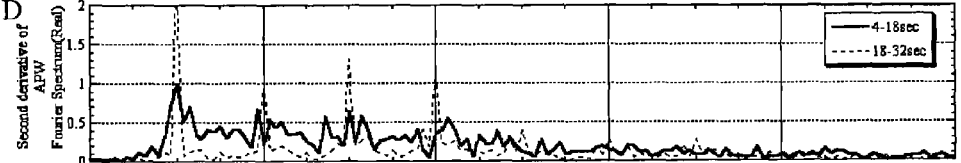
Figure 35E:
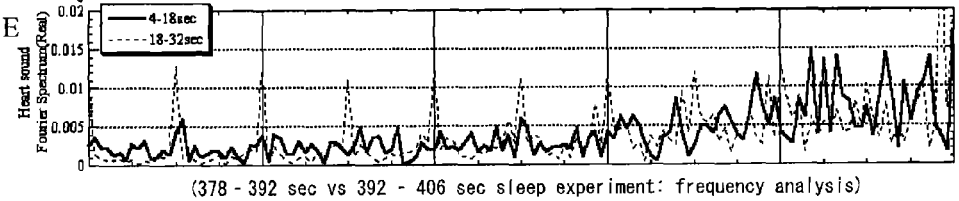

FIGS. 35A to 35E are diagrams comparing frequency analysis results of waveforms one another for 14 seconds (displayed as "4-18 sec" in the diagram) of 378 to 392 seconds and 14 seconds (displayed as "18-32 sec" in the diagram) of 392 to 406 seconds in FIG. 35A raw waveform of the finger plethysmogram, FIG. 35B second order differential waveform of the finger plethysmogram, FIG. 35C raw waveform of the APW, FIG. 35D second order differential waveform of the APW, and FIG. 35E raw waveform of the heart sound. From this diagram, the peaks in the vicinity of 0.4 to 0.6 Hz and the vicinity of 1.2 to 2 Hz indicating the rise in the sympathetic nerve activity can be grasped in FIG. 35C raw waveform of the APW and FIG. 35D second order differential waveform of the APW, but they cannot be grasped in the finger plethysmogram. Therefore, using the APW as a detected waveform is suitable for detecting the subjective sleepiness (equivalent to the low consciousness traveling state) from the rise in the sympathetic nerve activity.

From these facts, effectiveness of using a detection waveform of the APW and processing it as the frequency gradient time series waveform can be understood. Describing this point in detail, first, a change in increase/decrease of the sympathetic nervous system and the parasympathetic nervous system occurs in cycles of about 5 to 10 minutes from FIG. 32D, but the rise in the sympathetic nervous system indicated in this diagram appears as a base line fluctuation or a disturbance in waveform of the finger plethysmogram or the APW which are illustrated in FIGS. 33A to 33E and FIGS. 34A to 34E. On the other hand, absolute value processing waveforms of gradient time series waveforms of zero cross and peak of the APW match the activity state of the autonomic nervous system by wavelet analysis of the finger plethysmogram. However, when it is attempted to grasp only base line fluctuation and increase/decrease of amplitude and cycle of the raw waveform of the APW, it is just microscopically seeing fluctuation of the moment thereof, and it is difficult to determine whether the living body is toward wakefulness or toward sleep as a large tendency. Accordingly, it is appropriate to grasp with not only the raw waveform of the APW but also the frequency gradient time series waveform of the APW which is a waveform obtained by changing it to a long cycle, and by which the activity state of the autonomic nervous system can be accurately determined, which appears as a base line fluctuation or disturbance in waveform of the finger plethysmogram or the APW. That is, by grasping a large waveform with a long cycle as the frequency gradient time series waveform, it also functions as a filter against a negative feedback, which is not so effective, such as only very slightly affecting a physical condition change when a negative feedback is applied. In other words, an activity of the autonomic nervous system changes one by one according to stress, but a response of the living body to stress does not change according to a momentarily change of the autonomic nerve activity. A state change of the living body to stress is brought by accumulation of changes of the autonomic nerve activity. Therefore, it is not possible to accurately predict a state change of the living body by tracing momentary changes of the autonomic nerve activity one by one. The tendency of the living body to respond to stress can be grasped accurately by globally grasping changes of the autonomic nerve activity, and for this purpose, it is suitable to use the frequency gradient time series waveform.

INDUSTRIAL AVAILABILITY

The present invention is not limited to the cases where a biosignal measuring device is disposed in a driver's seat of an automobile to determine a biological state of a driver, and can be applied by disposing the biosignal measuring device on an operator's seat or a cockpit of various transportation apparatus, such as a train, an airplane, a ship, or the like.

EXPLANATION OF REFERENCE SYMBOLS 1 biosignal measuring device
11 core pad
12 spacer pad
13 sensor
14 front film
15 rear film
60 device for determining biological state during driving
61 analyzing and calculating means
611 frequency calculating means
612 frequency gradient calculating means
613 frequency fluctuation calculating means
614 distribution rate calculating means
615 degree of change calculating means
62 determining and detecting means
621 hypnagogic symptom phenomenon detecting means
622 imminent sleep phenomenon detecting means 623 subjective sleepiness/low consciousness traveling state detecting means
624 homeostasis function level determining means
625 initial fatigue determining means
626 feeling determining means
627 biological state determining means using history

The invention claimed is:

1. A device for determining biological state during driving, the device determining a biological state of a driver in a driving environment by using a biosignal sampled from a back of the driver by a biosignal measuring device provided in a driver's seat, the device comprising:

an analyzing and calculating means performing a predetermined calculation by using a time series waveform of the biosignal sampled by the biosignal measuring device; and a determining and detecting means determining or detecting the biological state by using a calculation result of the analyzing and calculating means, wherein the determining and detecting means comprises:

a hypnagogic symptom phenomenon detecting means detecting a hypnagogic symptom phenomenon which is a physical condition change phenomenon before falling asleep;

an imminent sleep phenomenon detecting means detecting an imminent sleep phenomenon which is a physical condition change phenomenon before falling asleep occurring after the hypnagogic symptom phenomenon occurs;

a subjective sleepiness/low consciousness traveling state detecting means detecting a subjective sleepiness which is being conscious of a sleepiness by oneself or a low consciousness traveling state due to a decrease in consciousness level; and a homeostasis function level determining means determining a level of adaptation ability of a homeostasis function, wherein the hypnagogic symptom phenomenon detecting means, the imminent sleep phenomenon detecting means, the subjective sleepiness/low consciousness traveling state detecting means and the homeostasis function level determining means are configured to function in parallel.

2. The device for determining biological state during driving according to claim 1, wherein the analyzing and calculating means comprises:

a frequency calculating means obtaining a time series waveform of a frequency from the time series waveform of the biosignal;

a frequency gradient calculating means performing a movement calculation to obtain a gradient of the frequency in every predetermined time window by using the time series waveform of the frequency obtained by the frequency calculating means, and outputting a time series change of the gradient of the frequency obtained in every time window as a frequency gradient time series waveform;

a frequency fluctuation calculating means performing a movement calculation to obtain an average value of the frequency in every predetermined time window by using the time series waveform of the frequency obtained by the frequency calculating means, and outputting a time series change of the average value of the frequency obtained in every time window as a frequency fluctuation time series waveform; and a means extracting frequency components corresponding to a function adjusting signal, a fatigue reception signal and an activity adjusting signal which are predefined from the frequency gradient time series waveform obtained by the frequency gradient calculating means and obtaining fluctuation of each of the frequency components.

3. The device for determining biological state during driving according to claim 2, wherein the means obtaining a fluctuation of frequency components corresponding to the function adjusting signal, the fatigue reception signal and the activity adjusting signal comprises:

a distribution calculating means obtaining, after the frequency components of less than 0.01 Hz belonging in a ULF band to a VLF band corresponding to the function adjusting signal, the fatigue reception signal and the activity adjusting signal are extracted, distribution rates of the respective frequency components in time series when a total of values of power spectra of the three frequency components is 100; and a degree of change calculating means applying smoothing differentiation to the time series distribution rates obtained by the distribution rate calculating means, and obtaining a degree of change of a distribution rate with respect to at least one frequency component from among the three frequency components between arbitrary time points on a time axis.

4. The device for determining biological state during driving according to claim 2, wherein the hypnagogic symptom phenomenon detecting means comprises a means determining that it is a hypnagogic symptom phenomenon when an increase tendency of amplitude is detected with respect to a predetermined criterion in the frequency gradient time series waveform obtained by the frequency gradient calculating means.

5. The device for determining biological state during driving according to claim 2, wherein the imminent sleep phenomenon detecting means comprises a means determining that it is an imminent sleep phenomenon when a convergence tendency of amplitude is detected with respect to a predetermined criterion in the frequency gradient time series waveform obtained by the frequency gradient calculating means and a cycle thereof becomes a long cycle.

6. The device for determining biological state during driving according to claim 3, wherein the subjective sleepiness/lour consciousness traveling state detecting means comprises a means detecting a light sleepiness or a momentary low consciousness traveling state on a condition that the distribution rate of the frequency component corresponding to the function adjusting signal among the three frequency components obtained by the distribution rate calculating means is equal to or higher than the distribution rate of the frequency component corresponding to the activity adjusting signal.

7. The device for determining biological state during driving according to claim 6, wherein the subjective sleepiness/low consciousness traveling state detecting means comprises a means detecting a light sleepiness or a momentary low consciousness traveling state on a condition that a degree of change of the frequency component corresponding to the function adjusting signal as well as a degree of change of the frequency component corresponding to the activity adjusting signal, among the three frequency components obtained by the degree of change calculating means, are equal to or larger than a predetermined value by absolute value.

8. The device for determining biological state during driving according to claim 6,
wherein the subjective sleepiness/low consciousness traveling state detecting means comprises a means determining whether a basic state of the driver is a relaxed state or a state of tension, and selecting a determination criterion for whether or not to correspond to the light sleepiness or the momentary low consciousness traveling state depending on whether the determined basic state is a relaxed state or a state of tension.

9. The device for determining biological state during driving according to claim 7,
wherein the subjective sleepiness/low consciousness traveling state detecting means further comprises a means detecting a strong sleepiness or a continuous low consciousness traveling state when respective peak values of the time series waveforms of distribution rates of the three frequency components obtained by the distribution rate calculating means are values which appear in a predetermined order within a range of difference in predetermined appearance time, and satisfy a predetermined distribution rate condition.

10. The device for determining biological state during driving according to claim 9,
wherein the means detecting the strong sleepiness or the continuous low consciousness traveling state in the subjective sleepiness/low consciousness traveling state detecting means determines the strong sleepiness or the continuous low consciousness traveling state when appearance times of peak values satisfying the predetermined distribution rate condition of the three frequency components obtained by the distribution rate calculating means satisfy a following relation:
activity adjusting signal≤function adjusting signal≤fatigue reception signal (where a difference in appearance times of the peak values of the activity adjusting signal and the fatigue reception signal is within a predetermined time).

11. The device for determining biological state during driving according to claim 6,
wherein the subjective sleepiness/low consciousness traveling state detecting means comprises a means determining a subjective sleepiness or a low consciousness traveling state when a convergence tendency of amplitude is detected with respect to a predetermined criterion in the frequency gradient time series waveform obtained by the frequency gradient calculating means.

12. The device for determining biological state during driving according to claim 1,
wherein the determining and detecting means further comprises an initial fatigue determining means determining presence of an initial fatigue at a start of driving, and
wherein the initial fatigue determining means determines that the driver has an initial fatigue when a same homeostasis function level continues for a predetermined time or more in the homeostasis function level determining means.

13. The device for determining biological state during driving according to claim 1,
wherein the determining and detecting means further comprises a feeling determining means determining a biological state in an early period of driving until a predetermined time passes after the driving is started.

14. The device for determining biological state during driving according to claim 1, further comprising
a biological state determining means using history determining the biological state of the driver by using history information of determination results obtained by the hypnagogic symptom phenomenon detecting means, the imminent sleep phenomenon detecting means, the subjective sleepiness/low consciousness traveling state detecting means and the homeostasis function level determining means.

15. A non-transitory computer readable medium including executable instructions, which when executed by a computer as a device for determining biological state during driving, the device determining a biological state of a driver in a driving environment by using a biosignal sampled from a back of the driver by a biosignal measuring device provided in a driver's seat, causes the computer to:
execute an analyzing and calculating procedure performing a predetermined calculation by using a time series waveform of the biosignal sampled by the biosignal measuring device;
execute a determining and detecting procedure determining or detecting the biological state by using a calculation result of the predetermined calculation; and
execute, as the determining and detecting procedure:
a hypnagogic symptom phenomenon detecting procedure detecting a hypnagogic symptom phenomenon which is a physical condition change phenomenon before falling asleep;
an imminent sleep phenomenon detecting procedure detecting an imminent sleep phenomenon which is a physical condition change phenomenon before falling asleep occurring after the hypnagogic symptom phenomenon occurs;
a subjective sleepiness/low consciousness traveling state detecting procedure detecting a subjective sleepiness which is being conscious of a sleepiness by oneself or a low consciousness traveling state due to a decrease in consciousness level; and
a homeostasis function level determining procedure determining a level of adaptation ability of a homeostasis function,
wherein the hypnagogic symptom phenomenon detecting procedure, the imminent sleep phenomenon detecting procedure, the subjective sleepiness/low consciousness traveling state detecting procedure and the homeostasis function level determining procedure are executed in parallel.

16. The non-transitory computer readable medium according to claim 15, wherein
the executable instructions, when executed by the computer, cause the computer to execute, as the analyzing and calculating procedure:
a frequency calculating procedure obtaining a time series waveform of a frequency from the time series waveform of the biosignal;
a frequency gradient calculating procedure performing a movement calculation to obtain a gradient of the frequency in every predetermined time window by using the time series waveform of the frequency obtained by the frequency calculating procedure, and outputting a time series change of the gradient of the frequency obtained in every time window as a frequency gradient time series waveform;
a frequency fluctuation calculating procedure performing a movement calculation to obtain an average value of the frequency in every predetermined time window by using the time series waveform of the frequency obtained by the frequency calculating procedure, and outputting a time series change of the average value of the frequency obtained in every time window as a frequency fluctuation time series waveform; and a procedure for extracting frequency components corresponding to a function adjusting signal, a fatigue reception signal and an activity adjusting signal which are predefined from the frequency gradient time series waveform obtained by the frequency gardient calculating procedure and obtaining a fluctuation of each of the frequency components.

17. The non-transitory computer readable medium according to claim 16, wherein
the executable instructions, when executed by the computer, cause the computer to execute, as the procedure for obtaining a fluctuation of frequency components corresponding to the function adjusting signal, the fatigue reception signal and the activity adjusting signal:
a distribution calculating procedure obtaining, after the frequency components of less than 0.01 Hz belonging in a ULF band to a VLF band corresponding to the function adjusting signal, the fatigue reception signal and the activity adjusting signal are extracted, distribution rates of the respective frequency components in time series when a total of values of power spectra of the three frequency components is 100; and
a degree of change calculating procedure applying smoothing differentiation to the time series distribution rates obtained by the distribution rate calculating procedure, and obtaining a degree of change of a distribution rate with respect to at least one frequency component from among the three frequency components between arbitrary time points on a time axis.

18. The non-transitory computer readable medium according to claim 16,
wherein the hypnagogic symptom phenomenon detecting procedure causes the computer to execute a procedure for determining that it is a hypnagogic symptom phenomenon when an increase tendency of amplitude is detected with respect to a predetermined criterion in the frequency gradient time series waveform obtained by the frequency gradient calculating procedure.

19. The computer program non-transitory computer readable medium according to claim 16,
wherein the imminent sleep phenomenon detecting procedure causes the computer to execute a procedure for determining that it is an imminent sleep phenomenon when a convergence tendency of amplitude is detected with respect to a predetermined criterion in the frequency gradient time series waveform obtained by the frequency gradient calculating procedure and a cycle thereof becomes a long cycle.

20. The non-transitory computer readable medium according to claim 17,
wherein the subjective sleepiness/low consciousness traveling state detecting procedure causes the computer to execute a procedure for detecting a light sleepiness or a momentary low consciousness traveling state on a condition that the distribution rate of the frequency component corresponding to the function adjusting signal among the three frequency components obtained by the distribution rate calculating procedure is equal to or higher than the distribution rate of the frequency component corresponding to the activity adjusting signal.

21. A device for determining biological state during driving, the device determining a biological state of a driver in a driving environment by using a biosignal sampled from a back of the driver by a biosignal measuring device provided in a driver's seat, the device comprising:
computer circuitry configured to
perform a predetermined calculation by using a time series waveform of the biosignal sampled by the biosignal measuring device;
determine or detect the biological state by using a calculation result of the predetermined calculation;
detect a hypnagogic symptom phenomenon which is a physical condition change phenomenon before falling asleep;
detect an imminent sleep phenomenon which is a physical condition change phenomenon before falling asleep occurring after the hypnagogic symptom phenomenon occurs;
detect a subjective sleepiness which is being conscious of a sleepiness by oneself or a low consciousness traveling state due to a decrease in consciousness level; and
determine a level of adaptation ability of a homeostasis function,
wherein the detection of the hypnagogic symptom phenomenon, the detection of the imminent sleep phenomenon, the detection of the subjective sleepiness, and the determination of the level of the adaptation ability are executed in parallel.

* * * * *